US010016169B2

(12) United States Patent
Meador et al.

(10) Patent No.: US 10,016,169 B2
(45) Date of Patent: *Jul. 10, 2018

(54) PHYSIOLOGICAL PARAMETER MEASURING PLATFORM DEVICE SUPPORTING MULTIPLE WORKFLOWS

(71) Applicant: Welch Allyn, Inc., Skaneateles Falls, NY (US)

(72) Inventors: Daniel Thomas Meador, Portland, OR (US); Janalee Esler, Portland, OR (US); Michele Marie Donovan, Auburn, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 489 days.

This patent is subject to a terminal disclaimer.

(21) Appl. No.: 14/705,406

(22) Filed: May 6, 2015

(65) Prior Publication Data

US 2015/0335296 A1 Nov. 26, 2015

Related U.S. Application Data

(63) Continuation of application No. 13/440,840, filed on Apr. 5, 2012, now Pat. No. 9,055,870.

(51) Int. Cl.

| | | |
|---|---|---|
| G06G 7/58 | (2006.01) | |
| A61B 5/00 | (2006.01) | |
| A61B 5/1455 | (2006.01) | |
| A61B 5/083 | (2006.01) | |
| A61B 5/145 | (2006.01) | |
| A61B 5/0205 | (2006.01) | |
| A61B 5/08 | (2006.01) | |
| G16H 40/20 | (2018.01) | |
| A61B 5/01 | (2006.01) | |
| A61B 5/021 | (2006.01) | |
| A61B 5/024 | (2006.01) | |

(52) U.S. Cl.
CPC .......... *A61B 5/7425* (2013.01); *A61B 5/0205* (2013.01); *A61B 5/0816* (2013.01); *A61B 5/0836* (2013.01); *A61B 5/14546* (2013.01); *A61B 5/14552* (2013.01); *A61B 5/72* (2013.01); *A61B 5/743* (2013.01); *A61B 5/746* (2013.01); *A61B 5/7435* (2013.01); *G16H 40/20* (2018.01); *A61B 5/0015* (2013.01); *A61B 5/01* (2013.01); *A61B 5/021* (2013.01); *A61B 5/02438* (2013.01); *A61B 5/14551* (2013.01); *A61B 2560/0431* (2013.01)

(58) Field of Classification Search
CPC .................................................. A61B 5/7425
USPC ....................................................... 703/11
See application file for complete search history.

(56) References Cited

U.S. PATENT DOCUMENTS

| | | |
|---|---|---|
| 5,140,519 A | 8/1992 | Friesdorf et al. |
| D366,460 S | 1/1996 | Jorensen |
| 5,701,894 A | 12/1997 | Cherry et al. |
| D427,574 S | 7/2000 | Sawada et al. |
| 6,219,046 B1 | 4/2001 | Thomas et al. |
| D454,139 S | 3/2002 | Feldcamp |
| 6,364,834 B1 | 4/2002 | Reuss et al. |
| 6,398,727 B1 | 6/2002 | Bui et al. |
| 6,416,471 B1 | 7/2002 | Kumar et al. |
| 6,469,717 B1 | 10/2002 | Wineke et al. |
| D465,226 S | 11/2002 | Friedman |
| D468,322 S | 1/2003 | Walker et al. |
| 6,535,714 B2 | 3/2003 | Melker et al. |
| 6,658,276 B2 | 12/2003 | Kiani et al. |
| 6,675,031 B1 | 1/2004 | Porges et al. |
| 6,707,476 B1 | 3/2004 | Hochstedler |
| 6,783,573 B2 | 8/2004 | Richardson |
| 6,828,910 B2 | 12/2004 | VanRyzin et al. |
| D510,582 S | 10/2005 | Hoang et al. |
| D523,440 S | 6/2006 | Hernandez et al. |
| D525,982 S | 8/2006 | Suzuki |
| D527,011 S | 8/2006 | Bixler |
| 7,124,366 B2 | 10/2006 | Foreman et al. |
| 7,134,994 B2 | 11/2006 | Alpert et al. |
| D545,829 S | 7/2007 | Fletcher |
| 7,336,187 B2 | 2/2008 | Hubbard, Jr. et al. |
| 7,360,693 B1 | 4/2008 | Sullivan |
| D575,296 S | 8/2008 | Fairfield et al. |
| 7,409,399 B2 | 8/2008 | Miyamoto |

(Continued)

FOREIGN PATENT DOCUMENTS

| | | |
|---|---|---|
| CN | 1356783 A | 7/2002 |
| CN | 1649538 A | 8/2005 |
| CN | 101069638 A | 11/2007 |
| EP | 0 707 824 A2 | 4/1996 |
| EP | 2 093 683 A2 | 8/2009 |

(Continued)

OTHER PUBLICATIONS

Adams, A.P., Breathing System Disconnections, Br. J. Anaesth, 1994, vol. 73, No. 1, pp. 46-54.
Al-Qutayri et al.; Framework for Secure Wireless Health monitoring and remote Access System, Inderscience Enterprises Ltd. copyright 2010, 19 pages.
Capnography: An Objective Tool for Assessing Respiratory Status, Physio-Control, Inc., 2008, pp. 1-8.

(Continued)

*Primary Examiner* — Jerry Lin
(74) *Attorney, Agent, or Firm* — Merchant & Gould P.C.

(57) ABSTRACT

A device obtains a series of measurements of a physiological parameter of one or more patients. The device displays a monitoring workflow home screen when the device is operating within a monitoring workflow. The device displays a non-monitoring workflow home screen when the device is operating within a non-monitoring workflow. The device displays a continuous workflow home screen when the device is operating within a continuous workflow. The monitoring workflow home screen, the non-monitoring workflow home screen, and the continuous workflow home screen are each different.

19 Claims, 35 Drawing Sheets

(56) References Cited

U.S. PATENT DOCUMENTS

| | | |
|---|---|---|
| D576,634 S | 9/2008 | Clark et al. |
| 7,428,531 B2 | 9/2008 | Barron et al. |
| D579,456 S | 10/2008 | Chen et al. |
| 7,433,827 B2 | 10/2008 | Rosenfeld et al. |
| D586,818 S | 2/2009 | Luck |
| D590,413 S | 4/2009 | Bhat et al. |
| D590,414 S | 4/2009 | Bhat et al. |
| D592,156 S | 5/2009 | Drews et al. |
| D592,675 S | 5/2009 | Bhat et al. |
| 7,565,616 B2 | 7/2009 | Buchmann |
| D598,923 S | 8/2009 | Chen et al. |
| D598,929 S | 8/2009 | Bhat et al. |
| D599,358 S | 9/2009 | Hoefnagels et al. |
| D599,398 S | 9/2009 | Laidlaw et al. |
| D603,416 S | 11/2009 | Poling et al. |
| D607,463 S | 1/2010 | Krieter et al. |
| D608,366 S | 1/2010 | Matas |
| 7,662,106 B2 | 2/2010 | Daniels et al. |
| D612,860 S | 3/2010 | Tarara et al. |
| RE41,236 E | 4/2010 | Seely |
| D614,634 S | 4/2010 | Nilsen |
| 7,765,479 B2 | 7/2010 | Goodwin et al. |
| 7,774,060 B2 | 8/2010 | Westenskow et al. |
| 7,782,302 B2 | 8/2010 | Lee et al. |
| 7,787,946 B2 | 8/2010 | Stahmann et al. |
| 7,810,497 B2 | 10/2010 | Pittman et al. |
| D632,699 S | 2/2011 | Judy et al. |
| 7,895,527 B2 | 2/2011 | Zaleski et al. |
| D635,150 S | 3/2011 | Sykes et al. |
| D637,603 S | 5/2011 | Godgart |
| 7,937,134 B2 | 5/2011 | Uber et al. |
| D640,264 S | 6/2011 | Fujii et al. |
| 7,967,759 B2 | 6/2011 | Couvillon, Jr. |
| D643,043 S | 8/2011 | Loken et al. |
| 8,001,967 B2 | 8/2011 | Wallace et al. |
| 8,020,558 B2 | 9/2011 | Christopher et al. |
| D646,689 S | 10/2011 | Ulliot |
| 8,028,701 B2 | 10/2011 | Al-Ali et al. |
| 8,038,593 B2 | 10/2011 | Friedman et al. |
| 8,046,705 B2 | 10/2011 | Hunleth et al. |
| 8,055,514 B2 | 11/2011 | Elsholz |
| 8,078,983 B2 | 12/2011 | Davis et al. |
| D652,051 S | 1/2012 | Judy et al. |
| D656,153 S | 3/2012 | Imamura et al. |
| D656,157 S | 3/2012 | Khan et al. |
| D656,946 S | 4/2012 | Judy et al. |
| D657,368 S | 4/2012 | Magee et al. |
| D658,196 S | 4/2012 | Wood et al. |
| D658,667 S | 5/2012 | Cho et al. |
| D662,106 S | 6/2012 | Mori et al. |
| D664,971 S | 8/2012 | Lee et al. |
| D664,984 S | 8/2012 | Lee et al. |
| D666,625 S | 9/2012 | Gilmore et al. |
| D667,837 S | 9/2012 | Magee et al. |
| D667,838 S | 9/2012 | Magee et al. |
| D674,401 S | 1/2013 | Trumble et al. |
| D675,218 S | 1/2013 | Arnold et al. |
| D676,863 S | 2/2013 | Ho Kushner et al. |
| D676,864 S | 2/2013 | Velasco et al. |
| D682,292 S | 5/2013 | Mori et al. |
| D688,685 S | 8/2013 | Rhee et al. |
| D689,899 S | 9/2013 | Lee et al. |
| D695,781 S | 12/2013 | Edwards et al. |
| 8,732,604 B2 | 5/2014 | Okamoto et al. |
| D708,210 S | 7/2014 | Capua et al. |
| 8,782,076 B2 | 7/2014 | Rothman et al. |
| D710,879 S | 8/2014 | Elston et al. |
| D711,895 S | 8/2014 | Inose et al. |
| D711,903 S | 8/2014 | Mishra et al. |
| 8,806,366 B2 | 8/2014 | Kim et al. |
| D712,420 S | 9/2014 | Song et al. |
| D714,822 S | 10/2014 | Capua et al. |
| D718,775 S | 12/2014 | Kim et al. |
| D720,772 S | 1/2015 | Cranfill et al. |
| D726,205 S | 4/2015 | Angelides |
| D726,206 S | 4/2015 | Angelides |
| D726,207 S | 4/2015 | Angelides |
| D726,751 S | 4/2015 | Angelides |
| D726,756 S | 4/2015 | Angelides |
| D726,757 S | 4/2015 | Angelides |
| D727,353 S | 4/2015 | Yokota et al. |
| D727,930 S | 4/2015 | Kim et al. |
| D730,376 S | 5/2015 | Ranz et al. |
| D730,927 S | 6/2015 | Lee et al. |
| D732,562 S | 6/2015 | Yan et al. |
| 9,055,870 B2 | 6/2015 | Meador et al. |
| D733,723 S | 7/2015 | Brinda et al. |
| D737,831 S | 9/2015 | Lee et al. |
| 9,131,904 B2 | 9/2015 | Qualey et al. |
| D740,313 S | 10/2015 | Seo et al. |
| 9,173,998 B2 | 11/2015 | Rosinko et al. |
| 9,180,243 B2 | 11/2015 | Michaud |
| 9,223,771 B2 | 12/2015 | Lehrian et al. |
| 9,235,682 B2 | 1/2016 | Vann et al. |
| 9,254,104 B2 | 2/2016 | Judy et al. |
| 9,259,526 B2 | 2/2016 | Barron et al. |
| 9,265,429 B2 | 2/2016 | St. Pierre et al. |
| 9,377,927 B2 | 6/2016 | Sciammarella et al. |
| 2002/0054141 A1 | 5/2002 | Yen et al. |
| 2002/0078097 A1 | 6/2002 | Chen et al. |
| 2002/0126137 A1 | 9/2002 | Kaestner, Jr. |
| 2002/0177758 A1 | 11/2002 | Schoenberg et al. |
| 2003/0060727 A1 | 3/2003 | Kline |
| 2003/0135087 A1 | 7/2003 | Hickle et al. |
| 2004/0002874 A1 | 1/2004 | Shaffer et al. |
| 2004/0088199 A1 | 5/2004 | Childress et al. |
| 2004/0111045 A1 | 6/2004 | Sullivan et al. |
| 2005/0114374 A1 | 5/2005 | Juszkiewicz et al. |
| 2005/0229110 A1 | 10/2005 | Gegner et al. |
| 2005/0288571 A1 | 12/2005 | Perkins |
| 2006/0149597 A1 | 7/2006 | Powell et al. |
| 2006/0200009 A1 | 9/2006 | Wekell et al. |
| 2006/0228096 A1 | 10/2006 | Hoshino et al. |
| 2006/0229557 A1 | 10/2006 | Fathallah et al. |
| 2006/0247948 A1 | 11/2006 | Ellis et al. |
| 2007/0000494 A1 | 1/2007 | Banner et al. |
| 2007/0067005 A1 | 3/2007 | Schatz et al. |
| 2007/0124240 A1 | 5/2007 | Ireland et al. |
| 2007/0130036 A1 | 6/2007 | Ireland et al. |
| 2007/0150810 A1 | 6/2007 | Katz et al. |
| 2007/0156456 A1 | 7/2007 | McGillin et al. |
| 2007/0167173 A1 | 7/2007 | Halcrow et al. |
| 2007/0167694 A1 | 7/2007 | Causevic et al. |
| 2007/0174079 A1 | 7/2007 | Kraus |
| 2007/0185390 A1 | 8/2007 | Perkins et al. |
| 2007/0197878 A1 | 8/2007 | Shklarski |
| 2007/0203744 A1 | 8/2007 | Scholl |
| 2007/0215157 A1 | 9/2007 | Straw |
| 2007/0276261 A1 | 11/2007 | Banet et al. |
| 2008/0012833 A1 | 1/2008 | Beck et al. |
| 2008/0021379 A1 | 1/2008 | Hickle |
| 2008/0055074 A1 | 3/2008 | Gao et al. |
| 2008/0058609 A1 | 3/2008 | Garibaldi et al. |
| 2008/0058614 A1 | 3/2008 | Banet et al. |
| 2008/0072896 A1 | 3/2008 | Setzer et al. |
| 2008/0077026 A1 | 3/2008 | Banet et al. |
| 2008/0086691 A1 | 4/2008 | Hopermann et al. |
| 2008/0103375 A1 | 5/2008 | Kiani |
| 2008/0115081 A1 | 5/2008 | Sankaravadivelu et al. |
| 2008/0155406 A1 | 6/2008 | Naka |
| 2008/0208812 A1 | 8/2008 | Quoc et al. |
| 2008/0229248 A1 | 9/2008 | Fagans et al. |
| 2008/0249377 A1 | 10/2008 | Molducci et al. |
| 2008/0249801 A1 | 10/2008 | Zaleski |
| 2008/0281168 A1 | 11/2008 | Gibson et al. |
| 2008/0281637 A1 | 11/2008 | Matz |
| 2008/0318529 A1 | 12/2008 | Harb |
| 2009/0005651 A1 | 1/2009 | Ward et al. |
| 2009/0054743 A1 | 2/2009 | Stewart |
| 2009/0054798 A1 | 2/2009 | Varney et al. |
| 2009/0112630 A1 | 4/2009 | Collins, Jr. et al. |
| 2009/0131761 A1 | 5/2009 | Moroney, III et al. |
| 2009/0132588 A1 | 5/2009 | Mahesh et al. |
| 2009/0143652 A1 | 6/2009 | Warburton et al. |

(56) References Cited

U.S. PATENT DOCUMENTS

| | | |
|---|---|---|
| 2009/0149927 A1 | 6/2009 | Kneuer et al. |
| 2009/0158415 A1 | 6/2009 | Dillon |
| 2009/0240116 A1 | 9/2009 | Bluth |
| 2009/0240193 A1 | 9/2009 | Mensinger et al. |
| 2009/0241958 A1 | 10/2009 | Baker, Jr. |
| 2009/0275805 A1 | 11/2009 | Lane et al. |
| 2009/0275810 A1 | 11/2009 | Ayers et al. |
| 2009/0282340 A1 | 11/2009 | Akaike et al. |
| 2009/0306482 A1 | 12/2009 | Davis et al. |
| 2009/0306488 A1 | 12/2009 | Al-Ali et al. |
| 2009/0312648 A1 | 12/2009 | Zhang et al. |
| 2010/0050075 A1 | 2/2010 | Thorson et al. |
| 2010/0069004 A1 | 3/2010 | Bioebaum |
| 2010/0094096 A1 | 4/2010 | Petruzzelli et al. |
| 2010/0097380 A1 | 4/2010 | Daniels et al. |
| 2010/0218766 A1 | 9/2010 | Milne |
| 2010/0249540 A1 | 9/2010 | Lisogurski |
| 2010/0274098 A1 | 10/2010 | Belford et al. |
| 2010/0324380 A1 | 12/2010 | Perkins et al. |
| 2011/0010621 A1 | 1/2011 | Wallaert et al. |
| 2011/0015502 A1 | 1/2011 | Peyser |
| 2011/0071420 A1 | 3/2011 | St. Pierre et al. |
| 2011/0169644 A1 | 7/2011 | Muhsin et al. |
| 2011/0190600 A1 | 8/2011 | McKenna et al. |
| 2011/0205577 A1 | 8/2011 | Mori et al. |
| 2011/0209707 A1 | 9/2011 | Terhark |
| 2011/0227739 A1 | 9/2011 | Gilham et al. |
| 2011/0245630 A1 | 10/2011 | St. Pierre et al. |
| 2011/0246565 A1 | 10/2011 | Irwin et al. |
| 2011/0276338 A1 | 11/2011 | Warner et al. |
| 2011/0290250 A1 | 12/2011 | Olson et al. |
| 2011/0313301 A1 | 12/2011 | Lane et al. |
| 2012/0000470 A1 | 1/2012 | Milne et al. |
| 2012/0016251 A1 | 1/2012 | Zhang et al. |
| 2012/0030610 A1 | 2/2012 | DiPerna et al. |
| 2012/0048090 A1 | 3/2012 | Etter et al. |
| 2012/0095778 A1 | 4/2012 | Gross et al. |
| 2012/0096367 A1 | 4/2012 | DelloStritto et al. |
| 2012/0110444 A1 | 5/2012 | Li et al. |
| 2012/0117099 A1 | 5/2012 | Gross |
| 2012/0215075 A1 | 8/2012 | Surace et al. |
| 2012/0296183 A1 | 11/2012 | Kinsley et al. |
| 2013/0151285 A1 | 6/2013 | McLaren et al. |
| 2013/0187780 A1 | 7/2013 | Angelides |
| 2013/0265327 A1 | 10/2013 | Vann et al. |
| 2013/0267792 A1 | 10/2013 | Petersen et al. |
| 2013/0267793 A1 | 10/2013 | Meador et al. |
| 2013/0267861 A1 | 10/2013 | Vassallo et al. |
| 2013/0268283 A1 | 10/2013 | Vann et al. |
| 2013/0293373 A1 | 11/2013 | Gegner et al. |
| 2013/0311926 A1 | 11/2013 | Keegan et al. |
| 2014/0040429 A1 | 2/2014 | Irwin et al. |
| 2014/0059436 A1 | 2/2014 | Swenson et al. |
| 2014/0098209 A1 | 4/2014 | Neff |
| 2014/0108041 A1 | 4/2014 | Bechtel et al. |
| 2014/0135588 A1 | 5/2014 | Al-Ali et al. |
| 2014/0331189 A1 | 11/2014 | Lee et al. |
| 2015/0186023 A1 | 7/2015 | Alisanski et al. |
| 2016/0085942 A1 | 3/2016 | Vann et al. |
| 2016/0196010 A1 | 7/2016 | Sheha et al. |
| 2016/0196041 A1 | 7/2016 | Lavoie |
| 2016/0196584 A1 | 7/2016 | Franklin et al. |
| 2016/0202866 A1 | 7/2016 | Zambetti et al. |
| 2016/0216868 A1 | 7/2016 | Victor |
| 2016/0217423 A1 | 7/2016 | Magnan et al. |
| 2016/0217599 A1 | 7/2016 | Neels et al. |

FOREIGN PATENT DOCUMENTS

| | | |
|---|---|---|
| GB | 2 409 951 A | 7/2005 |
| JP | 10-91687 A | 4/1998 |
| JP | 3682617 B2 | 8/2005 |
| JP | 2010-015193 A | 1/2010 |
| WO | 2001-26021 A1 | 4/2001 |
| WO | 2001-89362 A2 | 11/2001 |
| WO | 2006-076498 A2 | 7/2006 |
| WO | 2010-102069 A2 | 9/2010 |
| WO | 2011-001302 A1 | 1/2011 |

OTHER PUBLICATIONS

Colin Prodigy Press-Mate Prodigy II® Portable Vital Signs Monitors, DRE, Copyright 2009, accessed at: http://www.dremed.com/catalog/product_info.php/products_id/1181; 5 pages.

Fingertip Pulse Oximeter SPO2 Monitor Oxygen Oximeter; Copyright 1995-2010, accessed at: http://74.125.45.132/search?q=cache:ANfHne9je7gJ:cgi.ebay.com.sg/ws/eBayISAPI.dll%3FViewItem%26item%3D260412542031+"Fingertip+Pulse+Oximeter+SPO2+Monitor+Oxigen+Oximeter"&cd=2&hl=en&ct=clnk&gl=us; 6 pages.

Handheld Pulse Oximeter PM-60A, Contec Medical System Co. Ltd., Jul. 31, 2009; accessed at: http://www.tradeindia.com/selloffer/1858593/Handheld-Pulse-Oximeter-PM-60A.html; 5 pages.

International Search Report and Written Opinion in PCT/US2010/048450 dated Apr. 12, 2011, 9 pages.

International Search Report and Written Opinion in PCT/US2013/031342 dated Jun. 24, 2013, 12 pages.

International Search Report and Written Opinion in PCT/US2013/031458 dated Jun. 28, 2013, 10 pages.

International Search Report and Written Opinion in PCT/US2013/031486 dated Jun. 28, 2013, 10 pages.

International Search Report and Written Opinion in PCT/US2013/031582 dated Jun. 28, 2013, 11 pages.

Kozlovszky et al.; Network and Service Management and Diagnostics Solution of a Remote Patient Monitoring System, IEEE copyright 2011, 4 pages.

Lamberti et al.; Ubiquitous Real-Time Monitoring of Critical-Care Patients in Intensive Care Units, IEEE copyright 2003, 4 pages.

mCare 300 Vital Signs Monitor, Spacelabs Medical, Inc., Copyright 2006, 4 pages.

Multiple Vital Signs from One Non-invasive Sensor, Starr™ Life Sciences Corp., Copyright 2009, accessed at: http://www.starrlifesciences.com/mouseox.html; 1 page.

Nag et al., Wireless E-jacket ofr Multiparameter Biophysical Monitoring and Telemedicine Applications, Medial Devices and Biosensors, 2006, 3rd IEEE/EMBS Inernational Summer School, Sep. 4-6, 2006, pp. 40-44.

NTIA Handheld Pulse Oximeter, Frontline Systems; Dec. 31, 2009, accessed at: http://www.tradeindia.com/fp385774/NTIA-Handheld-Pulse-Oximeter.html; 3 pages.

O'Donoughue et al., Design and Implementation of a Framework for Monitoring Patients in Hospitals Using Wireless Sensors in Ad Hoc configuration, Engineering in Medicine and Biology Society, EMBS '06, 28th Annual International Confernece of the IEEE, vol., No., Aug. 30, 2006-Sep. 3, 2066, pp. 6449-6452.

Panorama™ Central Station, Surgical Product Guide copyright 2011, 2 pages.

Portable Patient Monitors, Welch Allyn, Copyright 2005-2006 MedDirect, Copyright 2005-2006, accessed at: http://www.meddirect.co.nz/Product.aspx?ProductId=3476; 1 page.

Station—Dictionary.com, [online], retrieved on Sep. 2, 2014, Retrived from, <URL: http://dictionary.reference.com/browse/station>, 4 pages.

U.S. Appl. No. 61/243,872, filed Sep. 18, 2009 expired, of record.

U.S. Appl. No. 12/751,579, filed Mar. 31, 2010.

U.S. Appl. No. 12/751,602, filed Mar. 31, 2010.

U.S. Appl. No. 29/353,090, filed Dec. 31, 2009.

U.S. Appl. No. 29/417,592, filed Apr. 5, 2012.

U.S. Appl. No. 29/417,611, filed Apr. 5, 2012.

Ultraview DM3—Dual Mode Vital Signs Monitor, Spacelabs Healthcare, Copyright 2010, 4 pages.

Zhao et al.; A Portable, Low-Cost, Batter-Powered Wireless Monitoring System for Obtaining Varying Physiologic Parameters from Multiple Subjects, IEEE copyright 2006, 4 pages.

Extended European Search Report for PCT/US2010/048450, dated Nov. 18, 2014, 7 pages.

Capnography: An Objecti ve Tool for Assessing Respiratory Status, Physio-Control, Inc., 2008, pp. 1-8.

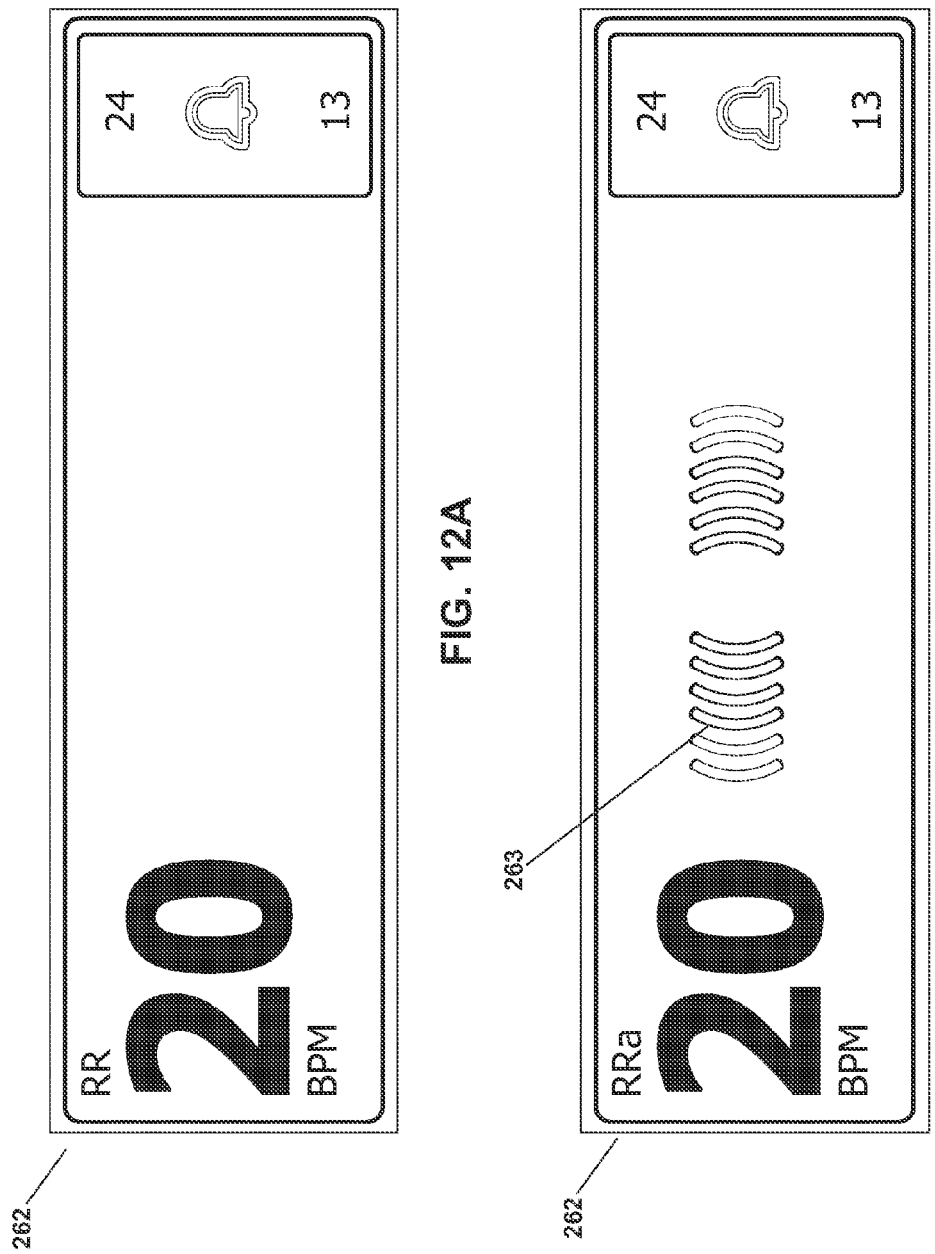

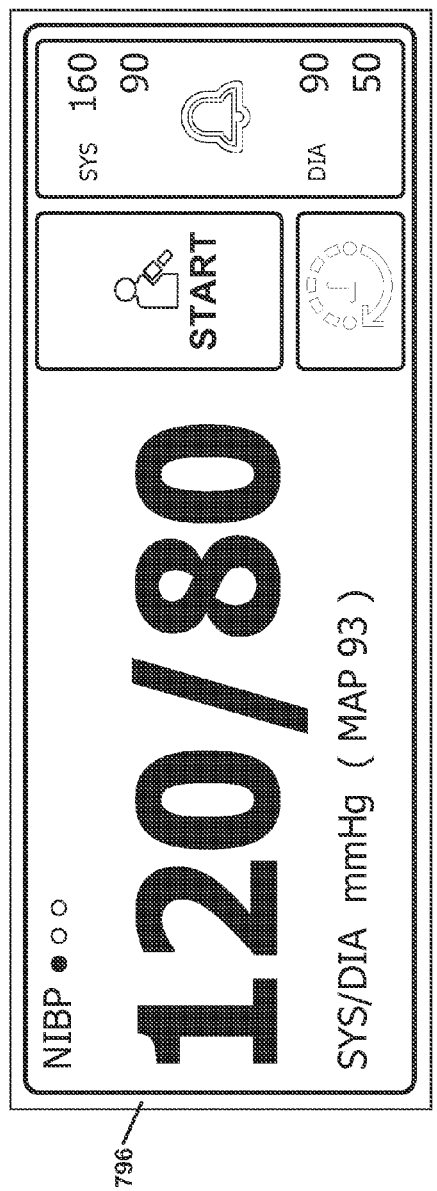
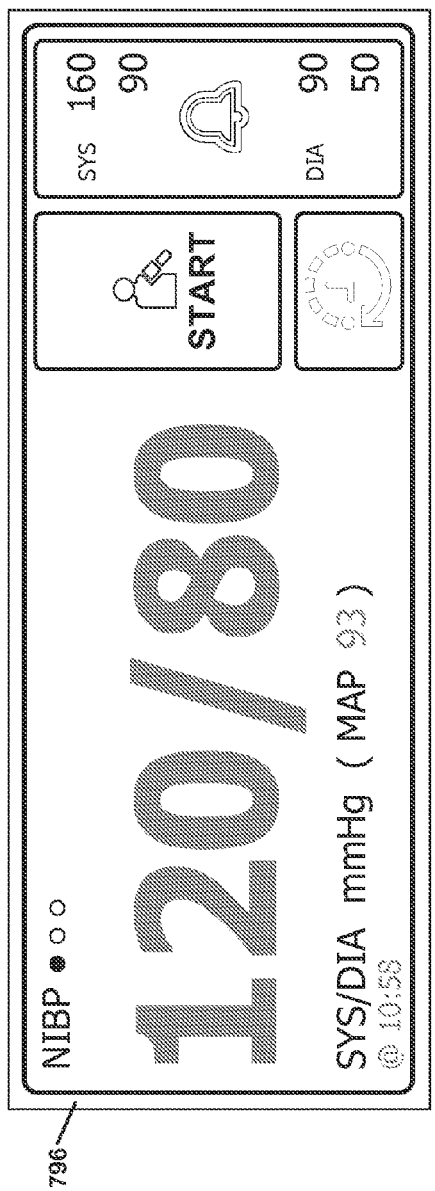
FIG. 13A
FIG. 13B

PHYSIOLOGICAL PARAMETER MEASURING PLATFORM DEVICE SUPPORTING MULTIPLE WORKFLOWS

RELATED APPLICATION

The present application is related to U.S. patent application Ser. No. 12/751,579 filed on Mar. 31, 2010, the entirety of which is hereby incorporated by reference.

BACKGROUND

Health care practitioners, such as nurses and physicians, use various types of health-care equipment to assist with the task of providing health care to a patient, also referred to herein as a health-care recipient. Some health-care equipment, referred to as single function equipment, is designed to perform a particular function, such as temperature measurement. Some health-care equipment, referred to as multi-function equipment, is designed to implement the performance of more than one function, such as temperature measurement and blood pressure measurement. Such multi-function equipment may impose excess bulk and/or weight upon a user if such multi-function equipment is used for only one function or a subset of the functions implemented by the multi-function equipment.

SUMMARY

In one aspect, a physiological measuring platform (PMP) device comprising: a central processing unit (CPU) that is configured to control operation of the PMP device; a display screen; and a set of one or more computer readable data storage media storing software instructions that, when executed by the CPU, cause the PMP device to: obtain a series of measurements of a physiological parameter of a monitored patient when the PMP device is operating within a monitoring workflow; display, on the display screen, a monitoring workflow home screen when the PMP device is operating within the monitoring workflow, the monitoring workflow home screen containing a first representation of the physiological parameter of the monitored patient, the first representation based on a measurement in the series of measurements; obtain a measurement of the physiological parameter of each patient in a series of patients when the PMP device is operating within a non-monitoring workflow; and display, on the display screen, a non-monitoring workflow home screen when the PMP device is operating within the non-monitoring workflow, the non-monitoring workflow home screen containing a second representation of the physiological parameter of a given patient in the series of patients, the second representation based on the measurement of the physiological parameter of the given patient in the series of patients; obtain a continuous measurement of the physiological parameter of the monitored patient when the PMP device is operating within a continuous workflow; and display, on the display screen, a continuous workflow home screen when the PMP device is operating within the continuous workflow, the continuous workflow home screen containing a third representation of the physiological parameter of the monitored patient, the third representation based on the measurement of the physiological parameter of the monitored patient; wherein the monitoring workflow home screen, the non-monitoring workflow home screen, and the continuous workflow home screen are each different.

Another aspect includes a method for performing physiological parameter measurements for a plurality of patients, the method including: displaying, by a physiological measurement platform (PMP) device, a settings screen on a display screen, the settings screen enabling a user to select a workflow within which the PMP device is to operate; when the PMP device is operating within a monitoring workflow: obtaining, by the PMP device, a series of measurements of a physiological parameter of a monitored patient; and displaying, by the PMP device, a monitoring workflow home screen on the display screen, the monitoring workflow home screen containing a first representation of the physiological parameter of the monitored patient, the first representation based on a measurement in the series of measurements; when the PMP device is operating within a non-monitoring workflow: obtaining, by the PMP device, a measurement of the physiological parameter of each patient in a series of patients; and displaying, by the PMP device, a non-monitoring workflow home screen on the display screen, the non-monitoring workflow home screen containing a second representation of the physiological parameter of a given patient in the series of patients, the second representation based on the measurement of the physiological parameter of the given patient in the series of patients; and when the PMP device is operating within a continuous workflow: obtaining, by the PMP device, continuous measurements of a continuous physiological parameter of the monitored patient; and displaying, by the PMP device, a continuous workflow home screen on the display screen, the continuous workflow home screen containing a third representation of the continuous physiological parameter of the monitored patient, the third representation based on a continuous measurement in the continuous measurements.

Yet another aspect includes a computer-readable storage medium comprising software instructions that, when executed, cause a physiological measurement platform (PMP) device to: obtain a series of measurements of a physiological parameter of a monitored patient when the PMP device is operating within a monitoring workflow; display, on the display screen, one of a plurality of workflow home screens, each of the workflow home screens being configured to address a different type of workflow; when a continuous workflow home screen is selected: obtain a continuous measurement of the physiological parameter of the monitored patient when the PMP device is operating within a continuous workflow; and display, on the display screen, the continuous workflow home screen when the PMP device is operating within the continuous workflow, the continuous workflow home screen containing a representation of the physiological parameter of the monitored patient, the representation based on the measurement of the physiological parameter of the monitored patient, the continuous workflow home screen including: an SpO2 frame displaying an oxygen saturation percentage and a pulse amplitude blip bar indicating a pulse beat relative pulse amplitude; an etCO2 frame displaying a numeric value representing etCO2 and a Capnogram waveform; an RR frame displaying a numeric value representing respirations per minute, wherein the aging is shown by changing a display color of the episodic data when an age of the data reaches a threshold.

DESCRIPTION OF THE DRAWINGS

FIGS. 12A-12B illustrate an example RR frame of the continuous workflow home screen.

FIGS. 13A-13B illustrate an example NIPB frame of the continuous workflow home screen.

DETAILED DESCRIPTION

Figure 1:
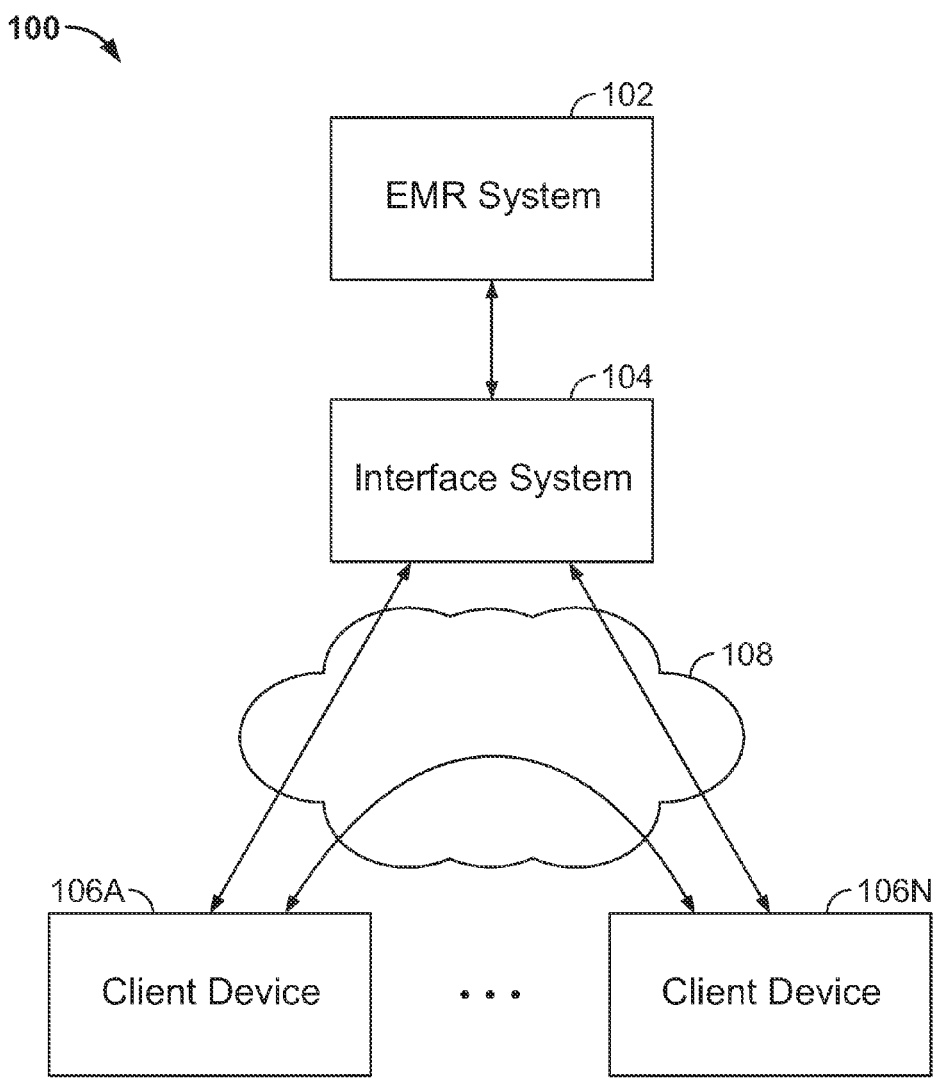
FIG. 1 is a block diagram illustrating an example system for collecting measurements of physiological parameters of patients.

Embodiments of the present invention are directed to a physiological parameter measuring platform (PMP) device having a user interface configured to operate within and transition between a plurality of workflows. These workflows can include a continuous workflow, a monitoring workflow, and a non-monitoring workflow.

In the following detailed description, references are made to the accompanying drawings that form a part hereof, and in which are shown by way of illustrations specific embodiments or examples. These embodiments may be combined, other embodiments may be utilized, and structural changes may be made without departing from the spirit or scope of the present disclosure. The following detailed description is therefore not to be taken in a limiting sense and the scope of the present disclosure is defined by the appended claims and their equivalents.

Referring now to the drawings, in which like numerals refer to like elements through the several figures, aspects of the present disclosure and an example computing operating environment will be described.

FIG. 1 is a block diagram illustrating an example system 100 for collecting measurements of physiological parameters of patients. As illustrated in the example of FIG. 1, the system 100 comprises an Electronic Medical Records (EMR) system 102, an interface system 104, a set of client devices 106A-106N (collectively, "client devices 106"), and a network 108.

The network 108 is an electronic communication network that facilitates communication between the client devices 106 and the interface system 104. An electronic communication network is a set of computing devices and links between the computing devices.

The computing devices in the network use the links to enable communication among the computing devices in the network. The network 108 can include routers, switches, mobile access points, bridges, hubs, intrusion detection devices, storage devices, standalone server devices, blade server devices, sensors, desktop computers, firewall devices, laptop computers, handheld computers, mobile telephones, and other types of computing devices. In various embodiments, the network 108 includes various types of links. For example, the network 108 can include wired and/or wireless links.

Furthermore, in various embodiments, the network 108 is implemented at various scales. For example, the network 108 can be implemented as one or more local area networks (LANs), metropolitan area networks, subnets, wide area networks (such as the Internet), or can be implemented at another scale.

The EMR system 102 is a computing system that allows storage, retrieval, and manipulation of electronic medical records. As used herein, a computing system is a system of one or more computing devices. A computing device is a physical, tangible device that processes data. Example types of computing devices include personal computers, standalone server computers, blade server computers, mainframe computers, handheld computers, smart phones, special purpose computing devices, and other types of devices that process data.

Each client device in the set of client devices 106 is a computing device. The client devices 106 can provide various types of functionality. For example, the set of client devices 106 can include one or more PMP devices (such as the PMP device 200). In addition, the set of client devices 106 can include one or more wall-mounted devices. Such wall-mounted devices can have similar functionality to the PMP device 200 but are stationary instead of portable.

In addition, the set of client devices 106 can include one or more monitor devices. Such monitor devices can display representations of physiological parameters, but do not directly obtain measurements of the physiological parameters from patients. A monitor device could, for example, be used by a clinician to monitor the physiological parameters of multiple patients.

The client devices 106 can communicate with each other through the network 108. In various embodiments, the client devices 106 can communicate various types of data with each other through the network 108. For example, in embodiments where the set of client devices 106 includes a set of PMP devices and a monitor device, each of the PMP devices can send data representing measurements of physiological parameters of patients to the monitor device. In this way, the monitor device can display representations of physiological parameters to a clinician.

The interface system 104 is a computing system that acts as an interface between the EMR system 102 and the client devices 106. In some embodiments, the interface system 104 is a Connex system. Different EMR systems have different software interfaces. For example, the EMR system used by two different hospitals can have two different software interfaces. The interface system 104 provides a single software interface to each of the client devices 106.

The client devices 106 send requests to software interface provided by the interface system 104. When the interface system 104 receives a request from one of the client devices 106, the interface system 104 translates the request into a request that works with the software interface provided by the EMR system 102. The interface system 104 then provides the translated request to the software interface provided by the EMR system 102.

When the interface system 104 receives a response from the EMR system 102, the interface system 104 translates the response from a format of the EMR system 102 to a system understood by the client devices 106. The interface system 104 then forwards the translated response to an appropriate one of the client devices 106.

The client devices 106 can send various types of data to the interface system 104 for storage in the EMR system 102 and can receive various types of data from the EMR system 102 through the interface system 104. For example, in some embodiments, the client devices 106 can send measurements of physiological parameters to the interface system 104 for storage in the EMR system 102. In another example, a monitor device can retrieve past measurements of physiological parameters of patients from the EMR system 102 through the interface system 104.

Figure 2A:
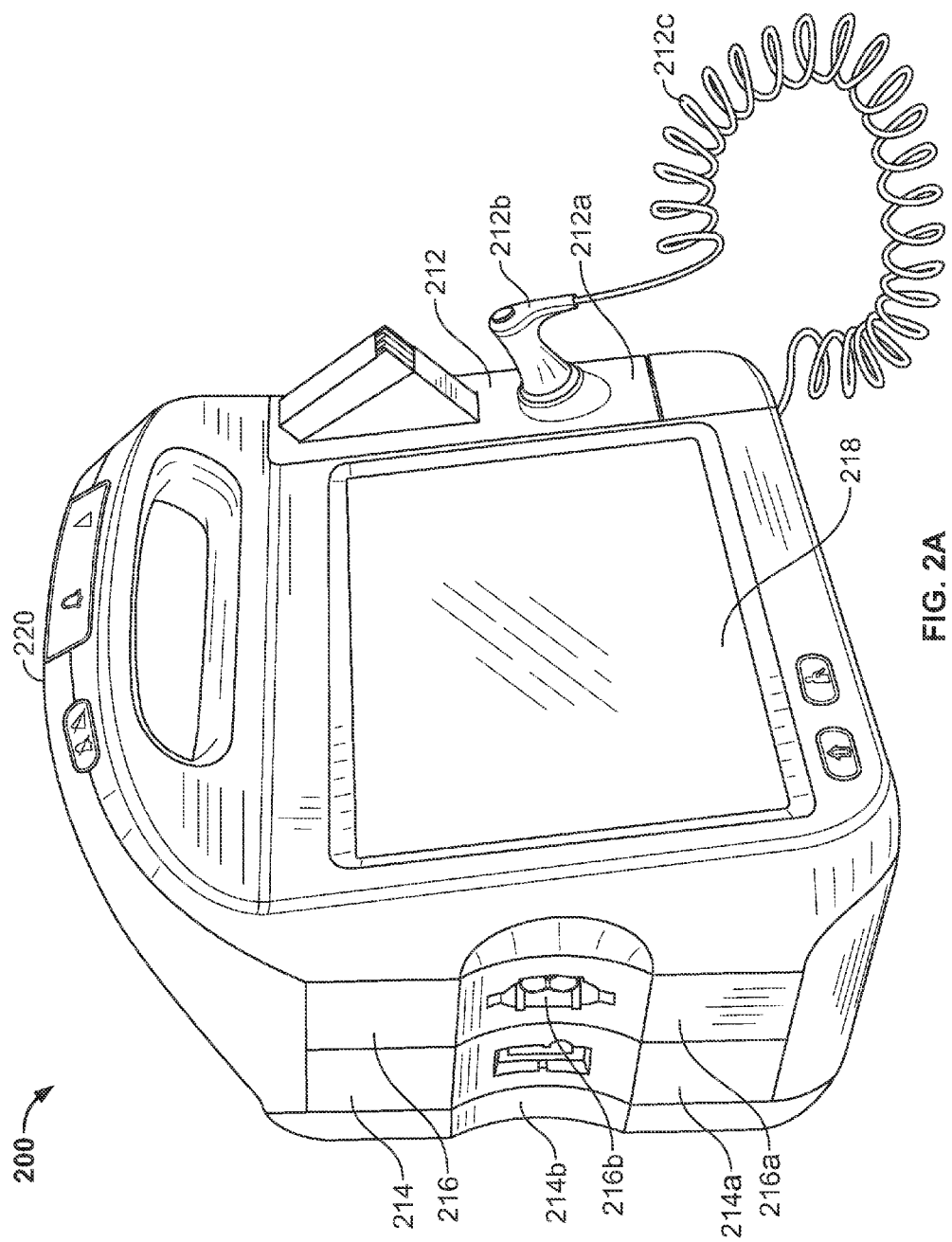
FIG. 2A illustrates a view of an example physiological parameter measuring platform (PMP) device.

FIG. 2A illustrates a view of a PMP device 200. The PMP device 200 is classified and referred to as a portable monitor platform device. The PMP device 200 includes multiple health care equipment (HCE) modules. Each of the HCE modules is configured to measure one or more physiological parameters of a health-care recipient, also referred to herein as a patient.

A temperature measurement module 212 is accessible from the front side of the PMP device 200. An oxygen saturation (SpO2) module 214 and a non-invasive blood pressure (NIBP) module 216 are accessible from a left hand side of the PMP device 200. An upper handle portion 220 enables the PMP device 200 to be carried by hand. Other modules, such as those described below, can also be used.

A front side of the PMP device 200 includes a display screen 218 and an outer surface of the temperature measurement module 212. The temperature measurement module 212 is designed to measure the body temperature of a patient. As used in this document, a "module" is a combination of a physical module structure which typically resides within the PMP device 200 and optional peripheral components (not shown) that typically attach to and reside outside of the PMP device 200.

The temperature measurement module 212 includes a front panel 212a. The front panel 212a has an outer surface that is accessible from the front side of the PMP device 200. The front panel 212a provides access to a wall (not shown) storing a removable probe (not shown), also referred to as a temperature probe, that is attached to a probe handle 212b. The probe and its attached probe handle 212b are tethered to the temperature measurement module 212 via an insulated conductor 212c. The probe is designed to make physical contact with a patient in order to sense a body temperature of the patient.

A left hand side of the PMP device 200 includes an outer surface of the SpO2 module 214 and an outer surface of the NIBP module 216. The SpO2 module 214 is a HCE module designed to measure oxygen content within the blood of a patient. The NIBP module 216 is a HCE module designed to measure blood pressure of a patient.

As shown, the SpO2 module 214 includes a front panel 214a. The front panel 214a includes an outer surface that is accessible from the left side of the PMP device 200. The front panel 214a includes a connector 214b that enables a connection between one or more peripheral SpO2 components (not shown) and a portion of the SpO2 module 214 residing inside the PMP device 200. The peripheral SpO2 components reside external to the PMP device 200. The peripheral SpO2 components are configured to interoperate with the SpO2 module 214 when connected to the SpO2 module 214 via the connector 214b. In some embodiments, the peripheral SpO2 components include a clip that attaches to an appendage of a patient, such as a finger. The clip is designed to detect and measure a pulse and an oxygen content of blood flowing within the patient.

As shown, the NIBP module 216 includes a front panel 216a having an outer surface that is accessible from the left side of the PMP device 200. The front panel 216a includes a connector 216b that enables a connection between one or more peripheral NIBP components (not shown) and a portion of the NIBP module 216 residing inside the PMP device 200. The peripheral NIBP components reside external to the PMP device 200. The peripheral NIBP components are configured to interoperate with the NIBP module 216 when connected to the NIBP module 216 via the connector 216b. In some embodiments, the peripheral NIBP components include an inflatable cuff that attaches to an appendage of a patient, such as an upper arm of the patient. The inflatable cuff is designed to measure the systolic and diastolic blood pressure of the patient, the mean arterial pressure (MAP) of the patient, and the pulse rate of blood flowing within the patient.

The PMP device 200 is able to operate within one or more workflows. A workflow is a series of one or more tasks that a user of the PMP device 200 performs. When the PMP device 200 operates within a workflow, the PMP device 200 provides functionality suitable for assisting the user in performing the workflow. When the PMP device 200 operates within different workflows, the PMP device 200 provides different functionality.

When the PMP device 200 is manufactured, the PMP device 200 is configured to be able to operate within one or more workflows. After the PMP device 200 is manufactured, the PMP device 200 can be reconfigured to operate within one or more additional workflows. In this way, a user can adapt the PMP device 200 for use in different workflows as needed.

In various embodiments, the PMP device 200 operates within various workflows. For example, in some embodiments, the PMP device 200 can operate within one or more of a continuous workflow, a monitoring workflow, and/or a non-monitoring workflow. Example types of non-monitoring workflows include, but are not limited to, a spot check workflow and a triage workflow.

In example embodiments, the names for the workflows can be defined by the user. For example, the user can rename a "triage workflow" as "ED 3 North" or any other nomenclature as desired to provide more context to the user.

When the PMP device 200 is operating with the continuous workflow, the PMP device 200 obtains a series of measurements of one or more physiological parameters of a single monitored patient continuously over a period of time. The continuous measurements can be taken over short intervals, such as 1 millisecond, 0.5 second, 1 second, 2 seconds, etc. In addition, the PMP device 200 displays, on the display screen 218, a continuous workflow home screen. The continuous workflow home screen contains a representation of a physiological parameter of the monitored patient. The representation is based on the continuous measurements taken by the PMP device 200.

When the PMP device 200 is operating within the monitoring workflow (sometimes referred to as "intervals monitoring") the PMP device 200 obtains a series of measurements of one or more physiological parameters of a single monitored patient periodically over a period of time. These periodic measurements can be taken at intervals such as 1 minute, 2 minutes, 5 minutes, 10 minutes, 15 minutes, 1 hour, 2 hours, 4 hours, 12 hours, etc. In addition, the PMP device 200 displays, on the display screen 218, a monitoring workflow home screen. The monitoring workflow home screen contains a representation of a physiological parameter of the monitored patient. The representation is based on at least one measurement in the series of measurements.

A representation of a physiological parameter is a visible image conveying information about the physiological parameter. For example, when the PMP device 200 is operating within the monitoring workflow, the PMP device 200 can obtain a temperature measurement of a single patient once every ten minutes for six hours. In this example, the PMP device 200 displays a monitoring workflow home screen that contains a representation of the patient's body temperature based on a most recent one of the temperature measurements. In this way, a user of the PMP device 200 can monitor the status of the patient.

When the PMP device 200 is operating within a non-monitoring workflow, the PMP device 200 obtains a measurement of one or more physiological parameters from each patient in a series of patients. In addition, the PMP device 200 displays a non-monitoring workflow home screen on the display screen 218. The non-monitoring workflow home screen contains a representation of the physiological parameter of a given patient in the series of patients. The representation is based on the measurement of the physiological parameter of the given patient.

In one example, when the PMP device 200 is operating within a spot check workflow, the PMP device 200 obtains blood pressure measurements from a series of previously-identified patients. In this other example, the PMP device 200 displays a spot check workflow home screen containing a blood pressure measurement of a given patient in the series of previously-identified patients. In this way, a user of the PMP device 200 can perform spot checks on the blood pressures of patients who have already been admitted to a hospital.

As used in this document, a patient is a previously identified patient when the PMP device 200 stores information regarding the identity of the patient. In another example, when the PMP device 200 is operating within a triage workflow, the PMP device 200 can obtain a single blood pressure measurement from each patient in a series of unidentified patients as the patients arrive at a hospital.

In this example, the PMP device 200 displays a triage workflow home screen containing a representation of the patients' blood pressure based on the single blood pressure measurements of the patients. In this way, a user of the PMP device 200 can perform triage on the series of unidentified patients as they arrive. As used in this document, a patient is an unidentified patient when the PMP device 200 does not store information regarding the identity of the patient.

The home screen for each type of workflow can be different to optimize the information shown. In some examples, the continuous monitoring workflow home screen displays measurements not shown in other workflows, such as SpO2, PR, etCO2, Fraction of inspired CO2 (FiCO2), IPI, RR and/or SpHb. In addition, the continuous monitoring workflow can display both continuous and episodic measurements. See FIGS. 13A-13B described below.

In some embodiments, the monitoring workflow home screen includes at least one user-selectable control that is not included in the non-monitoring workflow home screen. In other embodiments, a representation of a physiological parameter in the monitoring workflow home screen has a different size than a representation of the same physiological parameter in the non-monitoring workflow home screen.

Figure 2B:
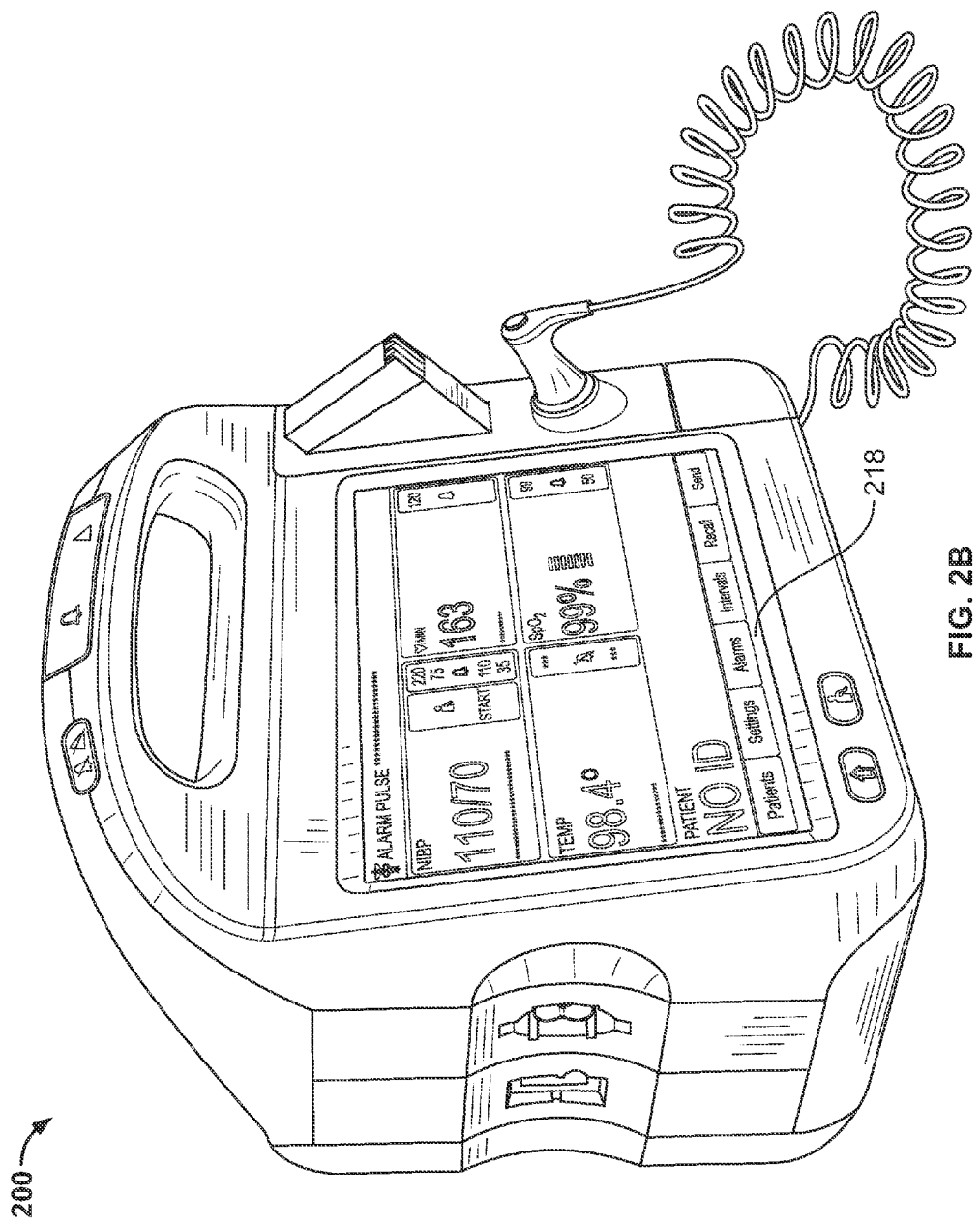
FIG. 2B illustrates an example user interface displayed on a user interface display of the PMP device of FIG. 2A.

FIG. 2B illustrates an example user interface displayed on the display screen 218 of FIG. 2A. The PMP device 200 outputs and displays user interfaces discussed in this document on the display screen 218.

Figure 3A:
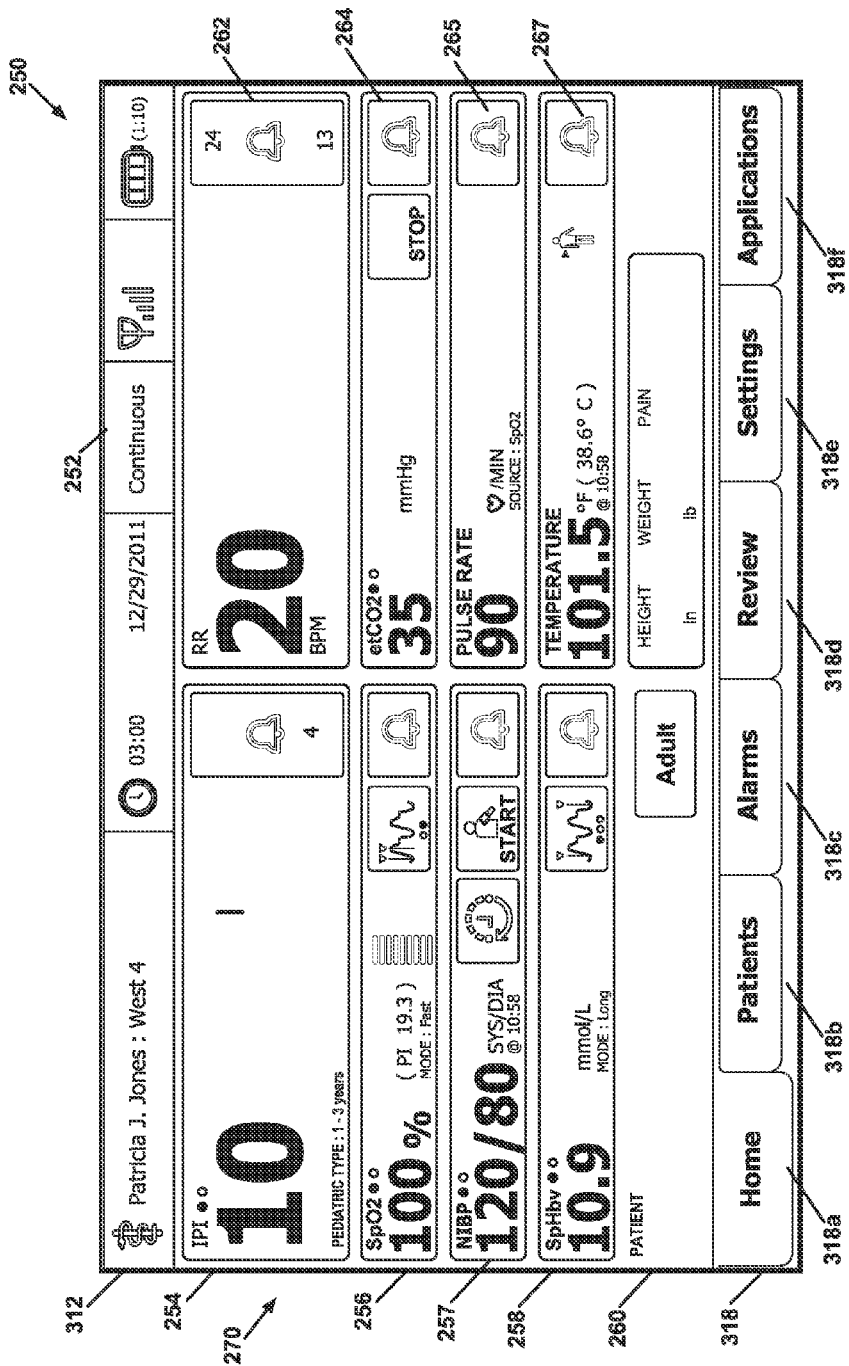
FIG. 3A illustrated an example continuous workflow home screen.

FIG. 3A illustrates an example continuous workflow home screen 250. The PMP device 200 displays the continuous workflow home screen 250 while the PMP device 200 is operating within a continuous workflow.

As described herein, the continuous workflow is designed for obtaining a continuous series of physiological measurements associated with an identified patient over a period of time.

As shown in the example of FIG. 3A, the continuous workflow home screen 250 includes a device status area 312, a navigation area 318, and a content area 270.

The device status area 312 contains data regarding a status of the PMP device 200. In the example of FIG. 3A, the device status area 312 includes text that identifies a clinician ("Patricia Jones") and a health care facility location ("West 4A"). A current time of day value ("19:31") is located towards the center of the device status area 312. A date value ("7/3/2012") is located to the right side of the time of day value. A remaining time of a battery ("1:10") value is located at the right side of the device status area 312.

In one example, the device status area 312 also includes a workflow indicator 252 that provides the user with an indication of the current workflow configuration for the PMP device 200. In this example, the workflow indicator 252 indicates that the PMP device 200 is in the "Continuous" workflow configuration. Other examples can include "Monitoring" and "Spot Check."

The PMP device 200 is functionally connected to one or more sensors that enable monitoring of at least one physiological parameter that is associated with a patient. Typically, each sensor is physically attached to the patient while the PMP device 200 is operating within the continuous workflow. Examples of these sensors include a respiration rate (RR) probe, an SpO2 probe, and an end tidal CO2 (etCO2) probe that are each attachable to the PMP device 200 as described above.

The content area 270 illustrates the various measurements taken by the PMP device 200 while in the continuous workflow configuration. The examples include an IPI frame 254, a SpO2 frame 256, an NIBP frame 257, a SpHbv frame 258, an RR frame 262, an etCO2 frame 264, a pulse rate frame 265, and a temperature frame 267.

The continuous workflow home screen 250 also includes a patient information section 260 that provides information about the patient. As described herein, such information can include patient name, room number, age (e.g., adult or child), etc.

The navigation area 318 of the continuous workflow home screen 250 includes a home tab 318a, a patients tab 318b, an alarms tab 318c, a review tab 318d, a settings tab 318e, and an applications tab 318f. The home tab 318a, the patients tab 318b, the alarms tab 318c, the review tab 318d, the settings tab 318e, and the applications tab 318f are referred to herein collectively as the screen tabs 318. Selection of screen tabs 318b-318f causes substitution of the monitoring workflow home screen 300 with another screen associated with the screen tabs 318b-318e. For example, the PMP device 200 displays a patient screen when a user selects the patients tab 318b.

Figure 4:
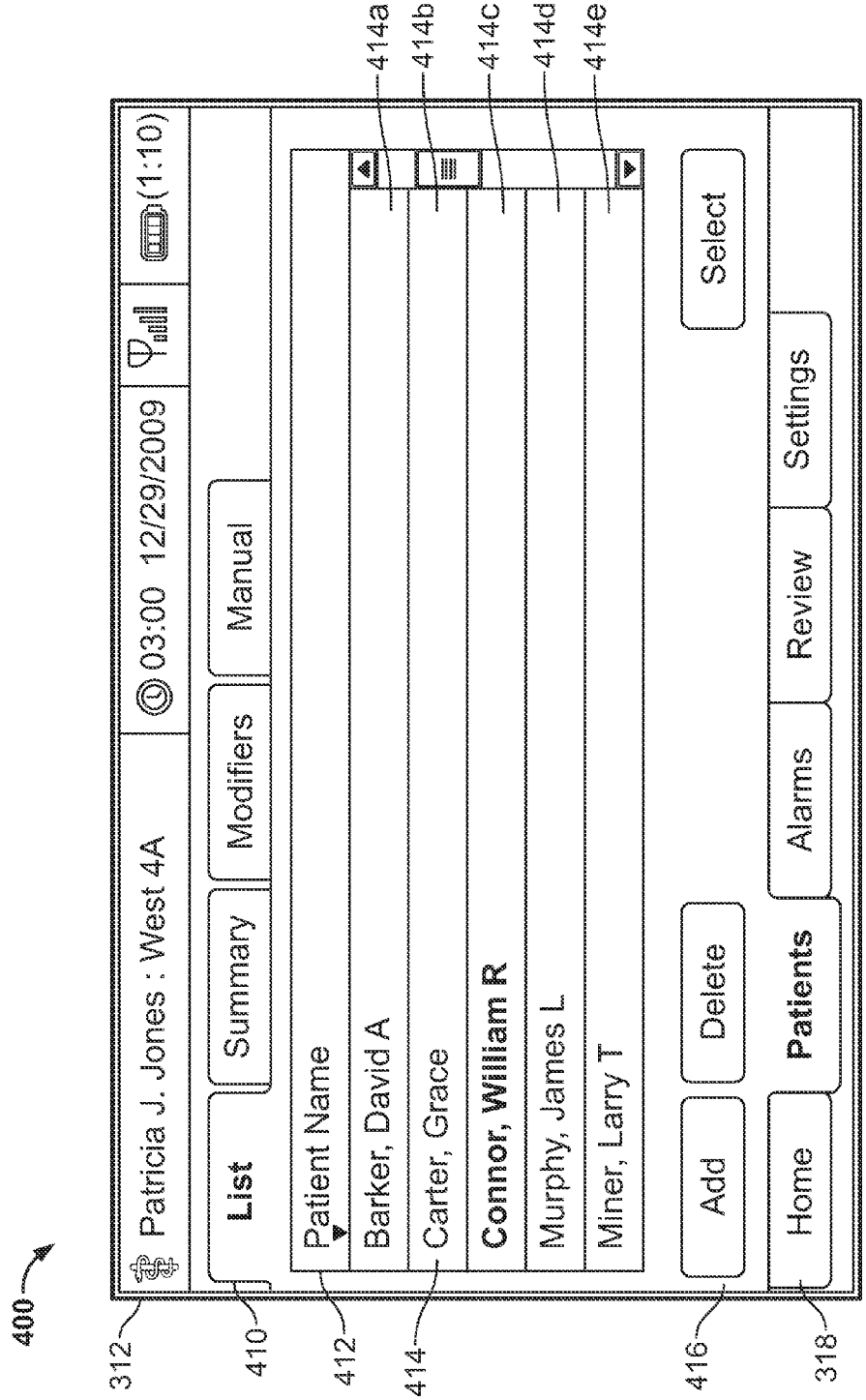
FIG. 4 illustrates an example patient selection screen.
Figure 5:
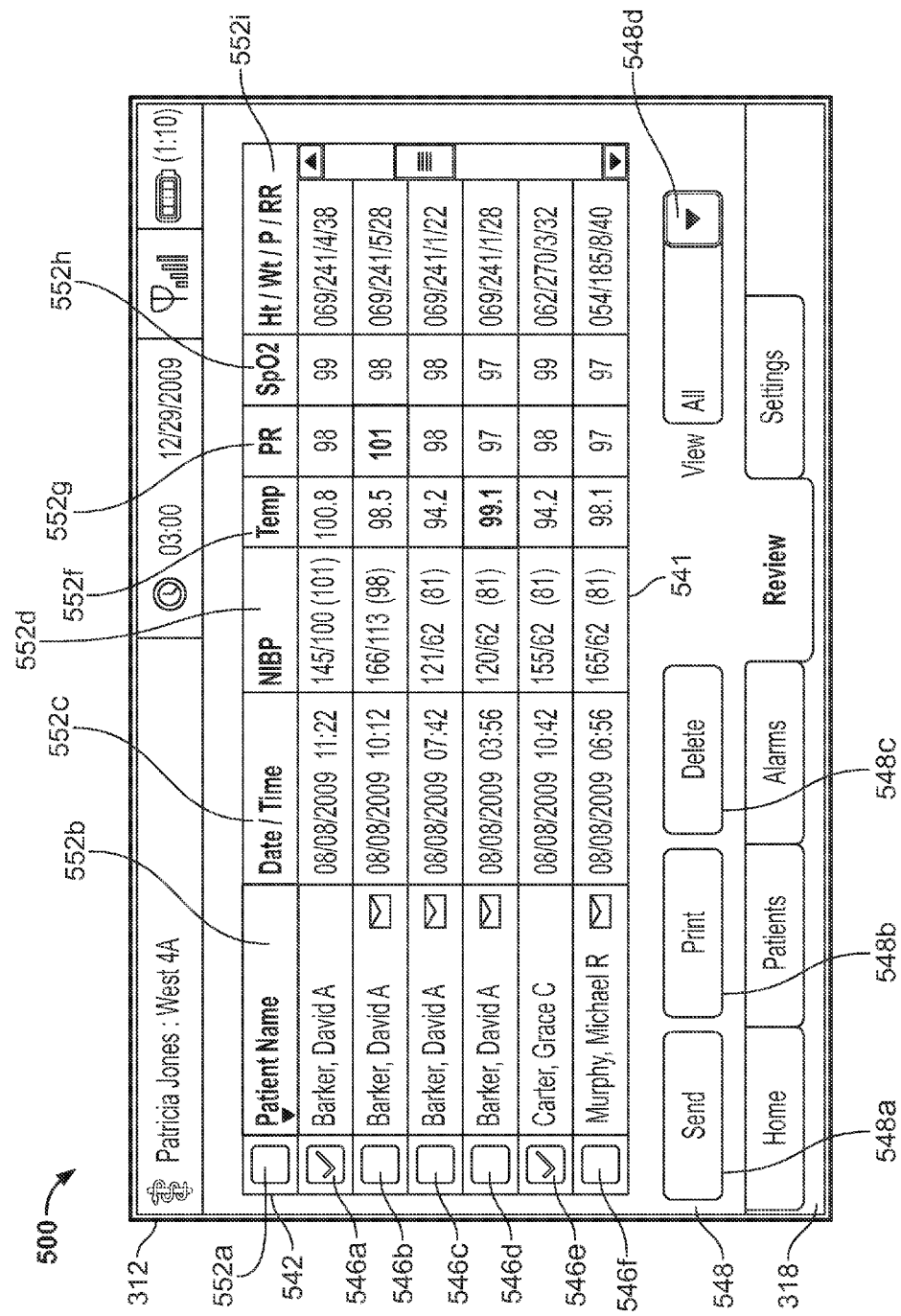
FIG. 5 illustrates an example review screen.

FIG. 4, discussed elsewhere in this document, illustrates an example patient selection screen. Furthermore, the PMP device 200 displays an alarms screen when a user selects the alarms tab 318c. FIGS. 7A-7E, discussed elsewhere in this document, illustrate an example alarms screen. Furthermore, the PMP device 200 displays a review screen when a user selects the review tab 318d. FIG. 5, discussed elsewhere in this document, illustrates an example review screen.

Furthermore, the PMP device 200 displays a settings screen when a user selects the settings tab 318e. FIGS. 6A-6G, discussed elsewhere in this document, illustrate an example settings screen. When the PMP device 200 displays a screen other than the monitoring workflow home screen 300 and a user selects the home tab 318a, the PMP device 200 displays the monitoring workflow home screen 300.

The PMP device 200 displays applications that have been installed on the PMP device 200 when the applications tab 318f is selected. Applications can be installed on the PMP device 200 to enhance the functionality of the PMP device 200. One example of such an application is a body mass index (BMI) calculator that allows the caregiver to calculate a BMI on the PMP device 200. When the applications tab 318f is selected, a list of the installed application is provided, and one or more of the applications can be launched by selecting the application. Additional details regarding a PMP device including such applications is provided in Patent Cooperation Treaty Application No. PCT/US2010/045814 filed on Aug. 17, 2010, the entirety of which is hereby incorporated by reference.

Figure 3B:
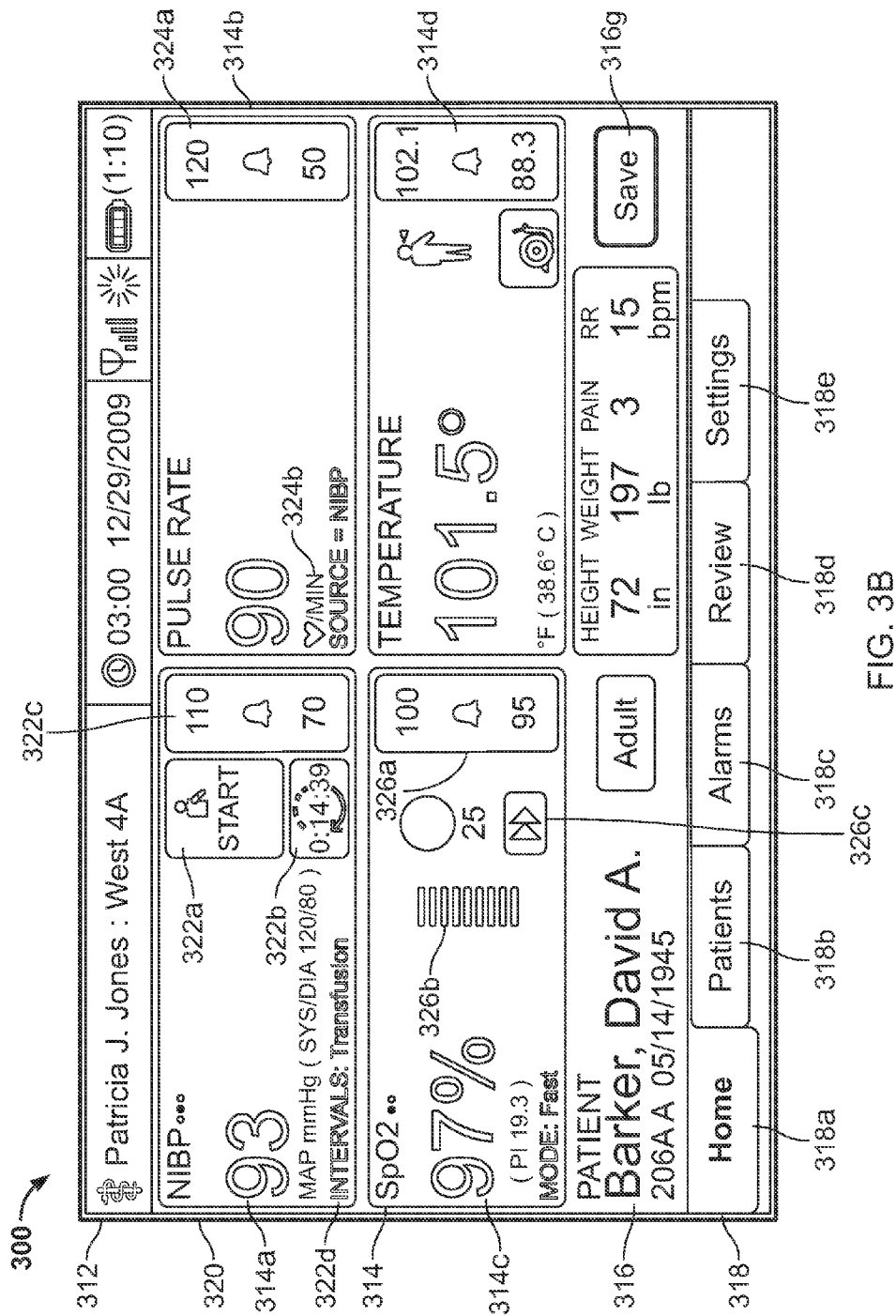
FIG. 3B illustrates an example monitoring workflow home screen.

FIG. 3B illustrates an example monitoring workflow home screen 300. The PMP device 200 displays the monitoring workflow home screen 300 while the PMP device 200 is operating within a monitoring workflow. The monitoring workflow is designed for obtaining a series of physiological measurements associated with an identified patient over a period of time.

The PMP device 200 is functionally connected to one or more sensors that enable monitoring of at least one physiological parameter that is associated with a patient. Typically, each sensor is physically attached to the patient while the PMP device 200 is operating within the monitoring workflow. These sensors include a temperature probe, a SpO2 clip, and a NIBP blood pressure cuff that are each attachable to the PMP device 200 as described above.

As shown in the example of FIG. 3B, the monitoring workflow home screen 300 includes the device status area 312, the navigation area 318, and a content area 320. The content area 320 is divided into a parameter reporting area 314 and a patient attribute area 316.

The parameter reporting area 314 includes one or more parameter reporting frames. Each of the parameter reporting frames contains a representation of a different physiological parameter for a patient. The representations are based on one or more measurements of the physiological parameters of a monitored patient. In addition, each of the parameter reporting frames contains an alarm reporting area. The alarm reporting areas specify upper alarm limits and lower alarm limits for the physiological parameters. The upper alarm limits and the lower alarm limits define the alarm ranges for the physiological parameters. Alarms associated with the physiological parameters are active when measurements of the physiological parameters are outside the alarm range for the physiological parameters.

In the example of FIG. 3B, the parameter reporting area 314 contains a NIBP frame 314a, a pulse rate frame 314b, a SpO2 frame 314c, and a temperature frame 314d. The NIBP frame 314a is located within an upper left portion of the parameter reporting area 314. The pulse rate frame 314b is located within an upper right portion of the parameter reporting area 314. The SpO2 frame 314c is located within a lower left portion of the parameter reporting area 314. The temperature frame 314d is located within a lower right portion of the parameter reporting area 314.

The NIBP frame 314a contains a representation of the blood pressure of the patient. The representation of the blood pressure of the patient is based on one or more measurements of the blood pressure of the patient. In various embodiments, the NIBP frame 314a contains various representations of the blood pressure of the patient. In the example of FIG. 3B, the NIBP frame 314a includes enlarged numerical text that represents a systolic blood pressure value ("120") and a diastolic blood pressure value ("80"), separated from each other via a slash '/' text character. The systolic blood pressure value is located at the left side of the NIBP frame 314a and the diastolic blood pressure is located to the right side of the systolic blood pressure value.

An NIBP alarm status area 322c is located at the right side of the NIBP frame 314a. The NIBP alarm status area 322c specifies an upper alarm limit and a lower alarm limit for the patient's systolic blood pressure and an upper alarm limit and a lower alarm limit for the patient's diastolic blood pressure. The upper alarm limit and the lower alarm limit for the patient's systolic blood pressure define a systolic blood pressure alarm range. The upper alarm limit and the lower alarm limit for the patient's diastolic blood pressure define a diastolic blood pressure alarm range. An alarm associated with the patient's blood pressure is active when the patient's systolic blood pressure is outside the systolic blood pressure alarm range or when the patient's diastolic blood pressure is outside the diastolic blood pressure alarm range The NIBP frame 314a also contains a NIBP cuff inflation stop button 322a. The NIBP cuff inflation stop button 322a is labeled with the text "Stop." The NIBP frame 314a also contains a NIBP automatic interval timer 322b. The NIBP automatic interval timer 322b is located between the diastolic blood pressure value and the NIBP alarm status area 322c. Selection of the NIBP cuff inflation stop button 322a ceases inflation of the NIBP cuff and toggles the label of the NIBP cuff inflation stop button 322*a* to display the ("Start") text. As used herein, a user selects a button or control when the user provides input to the PMP device 200 that specifies the control. For example, a user can select a control by pressing the control, by pressing another button while the control is highlighted, or by another means. Selection of the NIBP cuff inflation stop button 322*a* (now labeled the "Start" button) restarts inflation of the NIBP cuff and toggles the label of the NIBP cuff inflation stop button 322*a* to display the ("Stop") text. The NIBP automatic interval timer 322*b* indicates an amount of time remaining before the next scheduled inflation of the NIBP cuff. Additionally, a user can determine the age of the current NIBP reading on the NIBP frame 314*a* by subtracting the remaining time on the NIBP automatic interval timer 322*b* from the original interval duration. In the example of FIG. 3B, the NIBP frame 314*a* also displays a MAP value in an extended label field 322*d*.

The pulse rate frame 314*b* contains a representation of the patient's pulse rate. The representation of the patient's pulse rate is based on one or more measurements of the patient's pulse rate. In different embodiments, the pulse rate frame 314*b* contains different representations of the patient's pulse rate. In the example of FIG. 3B, the pulse rate frame 314*b* includes enlarged numerical text that represents a pulse rate value ("122"). The pulse rate value ("122") is located at the left side of the pulse rate frame 314*b*. A pulse rate alarm status area 324*a* is located at the right side of the pulse rate frame 314*b*. The pulse rate frame 314*b* also indicates a source of the pulse rate in an extended label field 324*b*.

The pulse rate alarm status area 324*a* specifies an upper alarm limit and a lower alarm limit. The upper alarm limit and the lower alarm limit define a pulse rate alarm range. An alarm associated with the patient's pulse rate is active when the patient's pulse rate is outside the pulse rate alarm range.

The SpO2 frame 314*c* contains a representation of the patient's SpO2 level. The representation of the patient's SpO2 level is based on one or more measurements of the patient's SpO2 level. In different embodiments, the SpO2 frame 314*c* contains different representations of the patient's SpO2 level. In the example of FIG. 3B, the SpO2 frame 314*c* includes enlarged numerical text that represents an SpO2 value ("97%"). The SpO2 value ("97%") is located at the left side of the SpO2 frame 314*c* and is accompanied by a '%' text character on the right side of the SpO2 value. A SpO2 alarm status area 326*a* is located at the right side of the SpO2 frame 314*c*. An SpO2 alarm parameter 326*d*, appearing as a circle adjacent to the text ("25"), indicates a duration of time. The SpO2 alarm status area 326*a* specifies an upper alarm limit and a lower alarm limit. The upper alarm limit and the lower alarm limit define a SpO2 alarm range. An alarm associated with the patient's SpO2 level is active when the patient's SpO2 level is outside the SpO2 alarm range for the duration of time indicated by the SpO2 alarm parameter 326*d*. The SpO2 frame 314*c* also includes a pulse amplitude blip bar 326*b* which indicates pulse beat and shows the relative pulse amplitude. As the detected pulse becomes stronger, more bars in the pulse amplitude blip bar 326*b* light up. The SpO2 frame 314*c* also includes an SpO2 response time control button 326*c* that is configured for a user to control the SpO2 alarm parameter 326*d*.

The temperature frame 314*d* contains a representation of the patient's body temperature. The representation of the patient's body temperature is based on one or more measurements of the patient's body temperature. In different embodiments, the temperature frame 314*d* contains different representations of the patient's body temperature. In the example of FIG. 3B, the temperature frame 314*d* includes enlarged numerical text that represents a temperature value ("101.5"). The temperature value ("101.5") is located at the left side of the temperature frame 314*d* and is accompanied by a Fahrenheit degree indicating symbol on the right side of the temperature value. A temperature alarm status area 328*a* is located at the right side of the temperature frame 314*d*. The temperature alarm status area 328*a* specifies an upper alarm limit and a lower alarm limit. The upper alarm limit and the lower alarm limit define a temperature alarm range. An alarm associated with the patient's temperature is active when the patient's temperature level is outside the temperature alarm range.

In some embodiments, the PMP device 200 can measure the patient's temperature in either a predictive mode or in a direct mode. When the PMP device 200 measures the patient's temperature in the predictive mode, the PMP device 200 predicts the patient's current temperature based on periodic readings of the patient's temperature. When the PMP device 200 measures the patient's temperature in the direct mode, the PMP device 200 continually measures the patient's temperature.

The temperature value in the temperature frame 314*d* is based on measurements received from a thermometer attached to a patient. When the PMP device 200 measures the patient's temperature in the predictive mode, the thermometer can be located at various places on the patient's body. Example locations on the patient's body where the thermometer can be located include in the patient's mouth, on the patient's thigh, in the patient's armpit, in the patient's rectum, and other locations. The temperature frame 314*d* includes a thermometry location control 328*b*. The thermometry location control 328*b* indicates a location on the patient's body where the thermometer is located. In the example of FIG. 3B, the thermometry location control 328*b* indicates that the thermometer is located in the patient's mouth.

When a user selects the thermometry location control 328*b*, the PMP device 200 updates the thermometry location control 328*b* such that the thermometry location control 328*b* indicates a different location on the patient's body or whether the PMP device 200 is to obtain measurements of the patient's temperature in direct mode. The user can continue selecting the thermometry location control 328*b* until the thermometry location control 328*b* indicates a location where the thermometer is located on the patient's body or until the thermometry location control 328*b* indicates that measurements are to be obtained in direct mode. For example, in some embodiments, the PMP device 200 accepts readings from a thermometer when the thermometer is located in the patient's mouth, in an adult patient's armpit, or in a pediatric patient's armpit. In this example, the thermometry location control 328*b* initially indicates that the thermometer is in a patient's mouth. When the user selects the thermometry location control 328*b* one time, the thermometry location control 328*b* indicates that the thermometer is located in an adult patient's armpit. When the user selects the thermometry location control 328*b* again, the thermometry location control 328*b* indicates that the thermometer is located in a pediatric patient's armpit. When the user selects the thermometry location control 328*b* yet again, the thermometry location control 328*b* indicates that the measurements of the patient's temperature are to be obtained in direct mode. When the user selects the thermometry location control 328*b* yet again, the thermometry location control 328*b* again indicates that the thermometer is located in a patient's mouth.

The display screen 218 enables a user to select the parameter reporting frames 314a-314d in order to change how the physiological parameters are represented in the parameter reporting frames 314a-314d. In other words, each of the parameter reporting frames 314a-314d contains an initial representation of a physiological parameter. The parameter reporting frame displays an alternate representation of the physiological parameter instead of the initial representation of the physiological parameter when a user selects the parameter reporting frame. For example, selecting the temperature frame 314d toggles the temperature value between being expressed in Fahrenheit or Centigrade. This feature is referred to as "tap to toggle." In another example, when a user selects the pulse rate frame 314b, the PMP device 200 displays a waveform in the pulse rate frame 314b instead of a number representing the patient's current pulse rate. The waveform represents a patient's pulse over time. In this example, when the user selects the pulse rate frame 314b again, the PMP device 200 displays a number in the pulse rate frame 314b representing the patient's current pulse rate. In yet another example, when the user selects the SpO2 frame 314c, the PMP device 200 displays a plethysmograhic waveform view in the SpO2 frame 314c. FIG. 3E illustrates an example alternate representation of a patient's SpO2 level. In the example of FIG. 3E, the SpO2 frame 314c contains a plethysmographic waveform view 325.

The patient attribute area 316 contains data that specify attributes of a patient. In various embodiments, the patient attribute area 316 contains data that specify various attributes of a patient. For example, in some embodiments, text that identifies a patient is located at the left side of the patient attribute area 316. In the example of FIG. 3B, the patient attribute area 316 contains the value "83645211" to identify the patient.

Furthermore, in the example of FIG. 3B, the patient attribute area 316 contains a patient type button 316b that is labeled with the text "Adult." The patient type button 316b is located towards the center of the patient attribute area 316. Patient-related attribute values that are labeled with the text ("HEIGHT"), ("WEIGHT"), ("PAIN") and ("RR") are located to the right side of the patient type button 316b. A save button 316g that is labeled with the text ("Save") is located at the right side of the patient attribute area 316.

The patient type button 316b indicates a value of a patient type parameter associated with the current patient. The patient type parameter can store a value of "Adult", "Pediatric", or "Neonatal" patient type. The patient type parameter controls the amount of air pressure applied to the NIBP cuff. Furthermore, in some embodiments, the patient type parameter controls the default alarm limits for the patient's physiological parameters. Thus, by using the patient type button 316b to change the patient type parameter, the user can automatically change the alarm limits for the patient's physiological parameters. As described elsewhere in this document, the user can also manually set the alarm limits for physiological parameters. When a user selects the patient type button 316b, the monitoring workflow home screen 300 is replaced by the patient selection screen as if the patients tab 318b was selected.

When the save button 316g is selected while the PMP device is operating in the monitoring workflow, the PMP device 200 saves a patient reading to local non-volatile storage within the PMP device 200. The patient reading is a set of data that includes measurements of the physiological parameters of the patient. If applicable, the patient reading can also include data indicating attributes of the patient. A user can use the review screen to review saved patient reading. Furthermore, in some embodiments, the PMP device 200 automatically attempts to transmit the patient reading to another computing node. A user can use the settings screen to specify the other computing node. In some embodiments, the other computing node is an electronic medical records system. Optionally, the other computing node is the interface system 104. The PMP device 200 does not clear the monitoring workflow home screen 300 when the save button 316g is selected.

The PMP device 200 can be configured to automatically save measurements as well. For example, when in the continuous workflow mode, the PMP device 200 can be configured to automatically store measured values at periodic intervals, such as once per second, once per minute, once every 5 minutes, etc.

The monitoring workflow is designed for obtaining a series of measurements of one or more physiological parameters of an identified patient over a period of time. A user uses the patient selection screen to select the identified patient. The PMP device 200 is programmable via an intervals pane of the settings screen to periodically record measurements of one or more physiological parameters over time from the identified patient.

A user may select the save button 316g one or more times. Each time the user selects the save button 316g, the PMP device 200 locally saves the patient reading and may attempt to send the patient reading to another computing node. The sending is dependent on the workflow in which the PMP device 200 is operating. In the spot check workflow (see FIG. 3C), the PMP device 200 automatically sends the patient reading because a clinician is present when the measurements are obtained. When the PMP device 200 is operating in the monitoring workflow, a clinician may not be always present. Thus, the patient reading is not sent automatically. Instead, a clinician navigates to the review screen (See FIG. 5) and manually selects the patient reading that the user wants to send.

When the PMP device 200 is operating in the monitoring workflow, the representations of the physiological parameters and patient attributes remain displayed on the monitoring workflow home screen 300, regardless of whether or not the patient reading is saved locally and/or transmitted to another computing node in response to a selection of the save button 316g. Unlike the spot check and triage workflows, the PMP device 200 does not clear the monitoring workflow home screen 300 when a user selects the save button 316g.

In some embodiments, the home screens for each workflow supported by the PMP device 200 contain at least one common user interface element. The common user interface element has the same appearance in each of the home screens, but does not necessarily perform the same function in the home screens of the different workflows. In the example of FIG. 3B, the patient type button 316b and the save button 316g are user interface elements that are included within and common to the monitoring workflow home screen 300 and to home screens for the spot check workflow (FIG. 3C) and the triage workflow (FIG. 3D). Further, the patient type button 316b and the save button 316g have a same appearance but also have different functions depending upon which workflow the PMP device 200 is operating within.

When the PMP device 200 is operating in the monitoring workflow, the PMP device 200 clears the monitoring workflow home screen 300 upon discharge of the current (first) identified patient for which physiological parameters are being obtained. When the PMP device 200 clears the monitoring workflow home screen 300, the PMP device 200 modifies the monitoring workflow home screen 300 such that the monitoring workflow home screen 300 no longer contains data representing physiological parameters of a patient and attributes of the patient. The monitored patient is discharged by the selection of another (second) identified patient for which to obtain physiological data, via the patient selection screen 400 or by power-cycling the PMP device 200. Upon selection of the second patient, the PMP device 200 locally stores the patient reading for the first patient and transmits the patient reading for the first patient to another computing node when a user selects a send patient reading control 448a on the review screen (see FIG. 5). Upon attaching the sensors to the second identified patient, the PMP device 200 obtain measurements of a set of one or more physiological parameter from the second identified patient, periodically over time.

Unlike the home screens for non-monitoring workflows (e.g., the spot check workflow and the triage workflow), the monitoring workflow home screen 300 provides direct access to the alarm screen via the alarm status areas 322c, 324a, 326a, 328a located within the parameter reporting frames 314a-314d. Each alarm status area 322c, 324a, 326a, 328a (including the bell-shaped symbols) indicates high and low alarm limits and provides a visual indication of when an alarm is active.

Figure 3C:
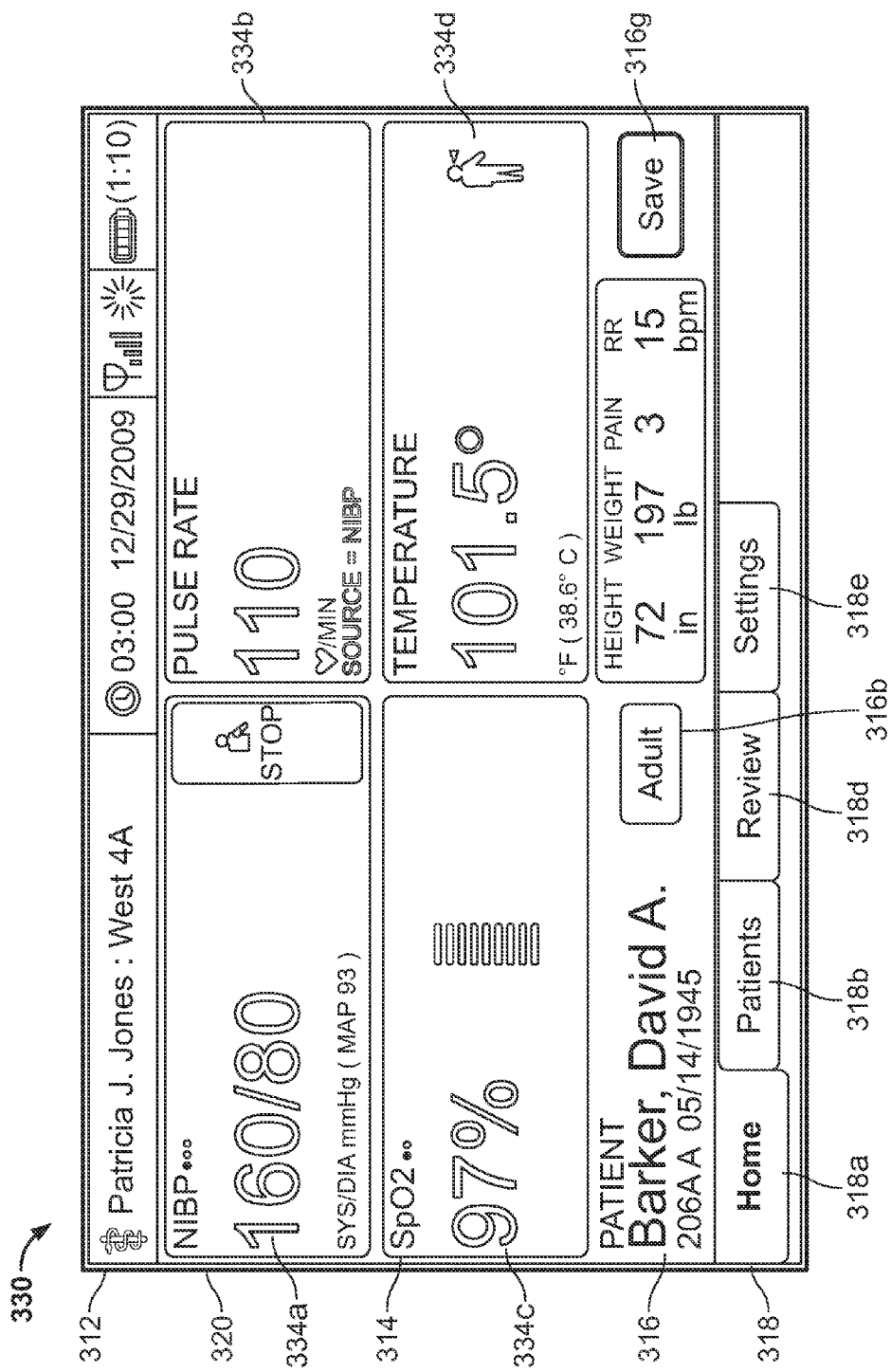
FIG. 3C illustrates an example spot check workflow home screen.
Figure 3D:
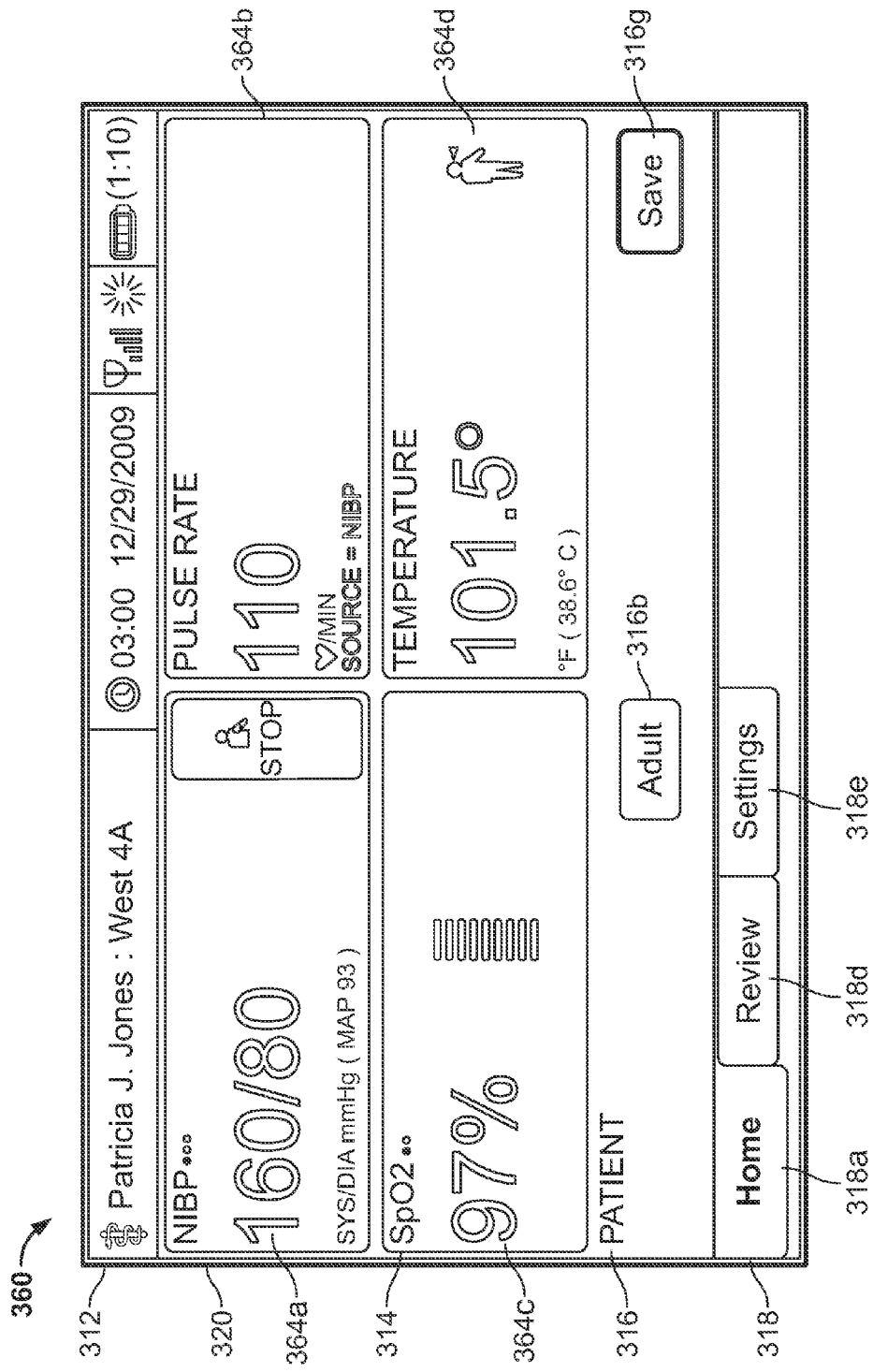
FIG. 3D illustrates an example triage workflow home screen.
Figure 3E:
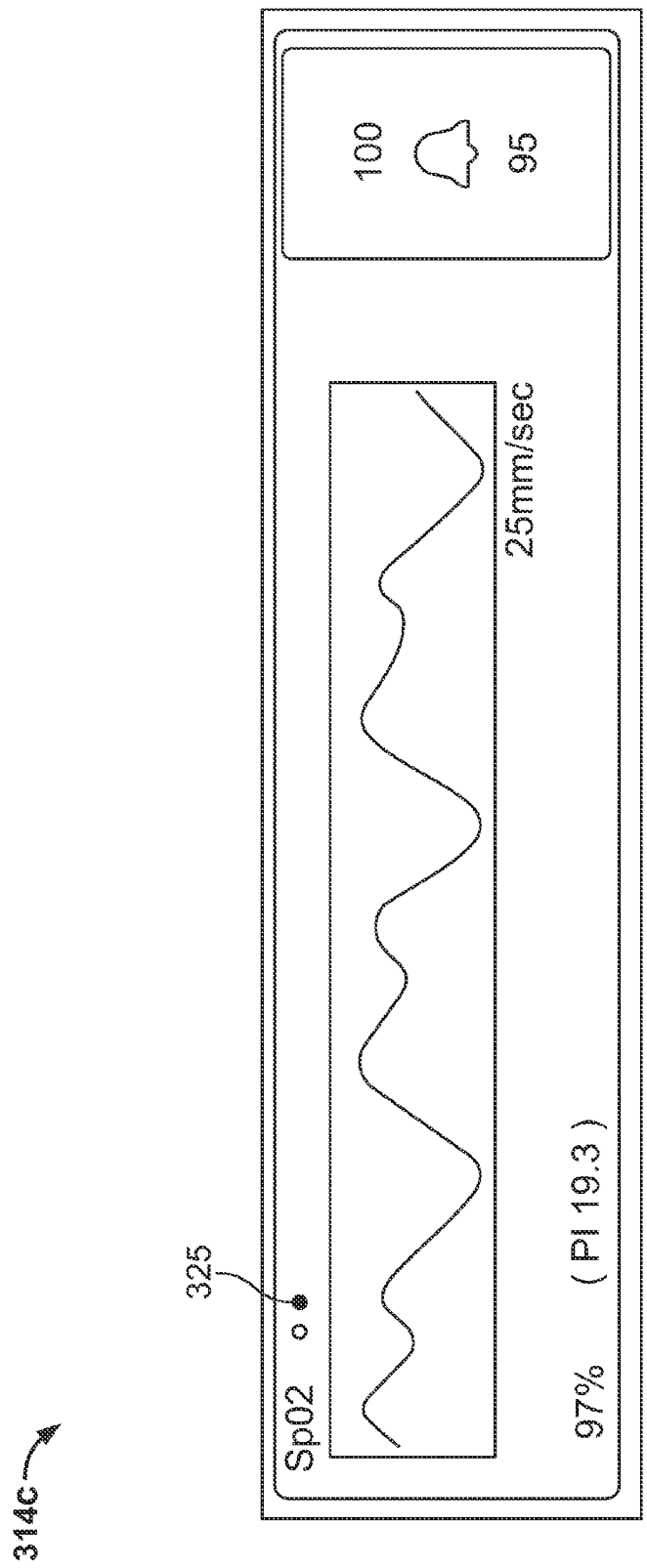
FIG. 3E illustrates an example alternative view of a patient's SpO2 level.
Figure 3F:
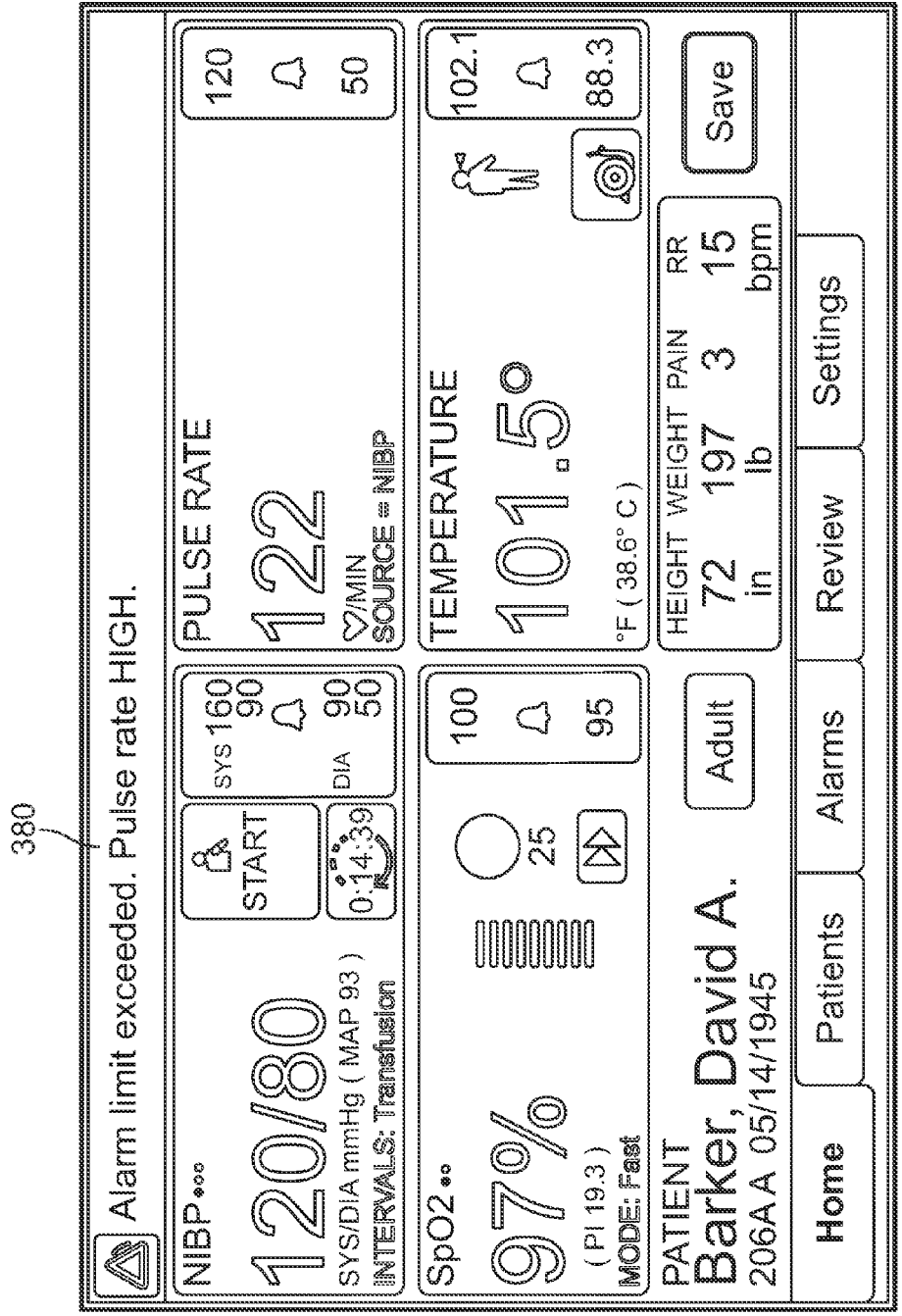
FIG. 3F illustrates the example monitoring workflow home screen when an alarm is active.

FIG. 3F illustrates the monitoring workflow home screen 300 when an alarm is active. When an alarm is active with respect to a particular physiological parameter, a perimeter around the parameter reporting frame for the particular physiological parameter transitions from a gray color to a red color. Changing the color of the perimeter provides a visual indication that the alarm is active. In some embodiments, the perimeter around the parameter reporting frame also flashes, thereby providing another visual indication that the alarm is active. Furthermore, the bell-shaped symbol within the alarm status area transitions from a white color to a red or yellow color, depending on a priority of the alarm. This provides another visual indication that the alarm is active. When the alarm is resolved, the bell-shaped symbol within the alarm status area transitions from the red or yellow color to the white color. In the example of FIG. 3F, an alarm associated with the patient's pulse rate is active. Accordingly, the perimeter around the pulse rate frame 314b is red instead of gray.

Furthermore, as illustrated in the example of FIG. 3F, when an alarm associated with a particular physiological parameter is active, the PMP device 200 causes the device status area 312 to display an alarm message 380. The alarm message 380 visually indicates that an alarm is active and indicates a brief description of the alert. In the example FIG. 3F, the alarm message 380 indicates that the reason for the alert is that the patient's heart rate is too high.

Furthermore, when an alarm associated with a particular physiological parameter is active, the PMP device 200 emits an alarm sound. The PMP device 200 continues to emit the alarm sound until the alarm is deactivated or until a user temporarily silences the alarm sound. When the user temporarily silences the alarm sound, the PMP device 200 suspends emitting the alarm sound for a given time period. In various embodiments, the user is able to temporarily silence the alarm sound in various ways. For example, in some embodiments, the user temporarily silences the alarm sound by touching the parameter reporting frame corresponding to the alarm. In other embodiments, the user temporarily silences the alarm sound by touching the alarm message 380. In yet other embodiments, the user temporarily silences the alarm sound by selecting a physical button on the PMP device 200.

When the user temporarily silences the alarm sound, the PMP device 200 resumes emitting the alarm sound after a given time period expires. For example, in some embodiments, the PMP device 200 resumes emitting the alarm sound after 30 seconds. When the user temporarily silences the alarm sound, the alarm message 380 indicates a time remaining before the PMP device 200 resumes emitting the alarm sound.

Figure 3G:
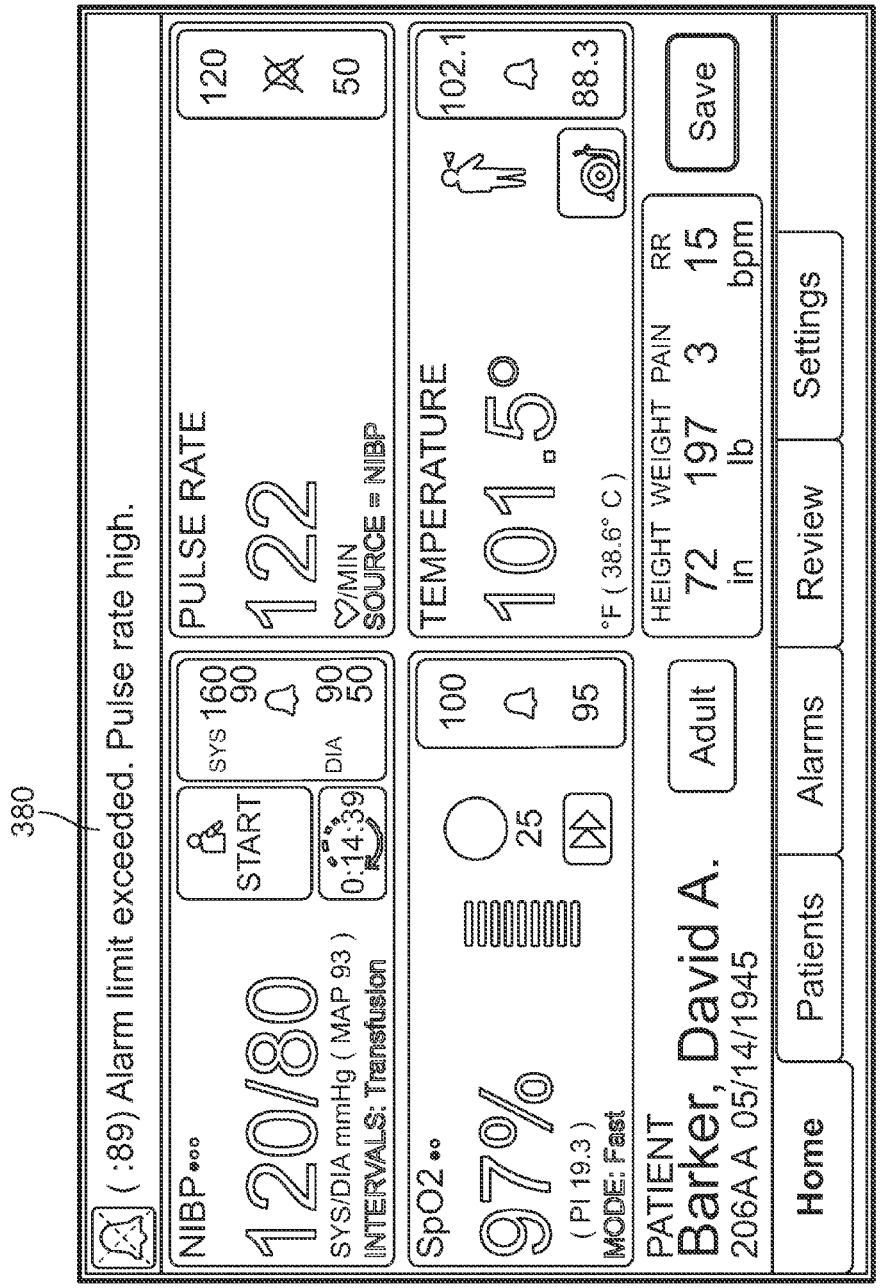
FIG. 3G illustrates the example monitoring workflow home screen when an alarm is active and when an alarm sound for the alarm has been temporarily silenced.

FIG. 3G illustrates the monitoring workflow home screen 300 when an alarm is active and when the alarm sound for the alarm has been temporarily silenced. In the example of FIG. 3G, the alarm message 380 indicates that eighty-nine seconds remain before the PMP device 200 resumes emitting the alarm sound.

In some embodiments, the user is able to temporarily silence the alarm sound for various lengths of time by selecting a button on the PMP device 200 or a control displayed by the PMP device 200 multiple times. For example, when the user selects the alarm message 380 one time, the PMP device 200 resumes emitting the alarm sound after sixty seconds. In this example, each time the user selects the alarm message 380, the PMP device 200 adds thirty seconds to the length of time before the PMP device 200 resumes emitting the alarm sound. In some embodiments, the PMP device 200 prevents the user from temporarily silencing the alarm sound for more than a given amount of time. For example, in some embodiments, the PMP device 200 prevents the user from temporarily silencing the alarm sound for more than five minutes.

When the user temporarily silences an alarm sound for an alarm, the monitoring workflow home screen 300 visually indicates that the alarm sound has been temporarily silenced. In various embodiments, the monitoring workflow home screen 300 visually indicates that the alarm sound has been temporarily silenced in various ways. For example, in some embodiments, the alarm message 380 contains a bell-shaped icon when the alarm sound has been temporarily silenced. In this example, the bell-shaped icon has an X-shaped mark over a bell. The lines of the X-shaped mark are dashed. In other example embodiments, the alarm message 380 or other parts of the monitoring workflow home screen 300 contain differently shaped icons or visual indicators.

Figure 7A:
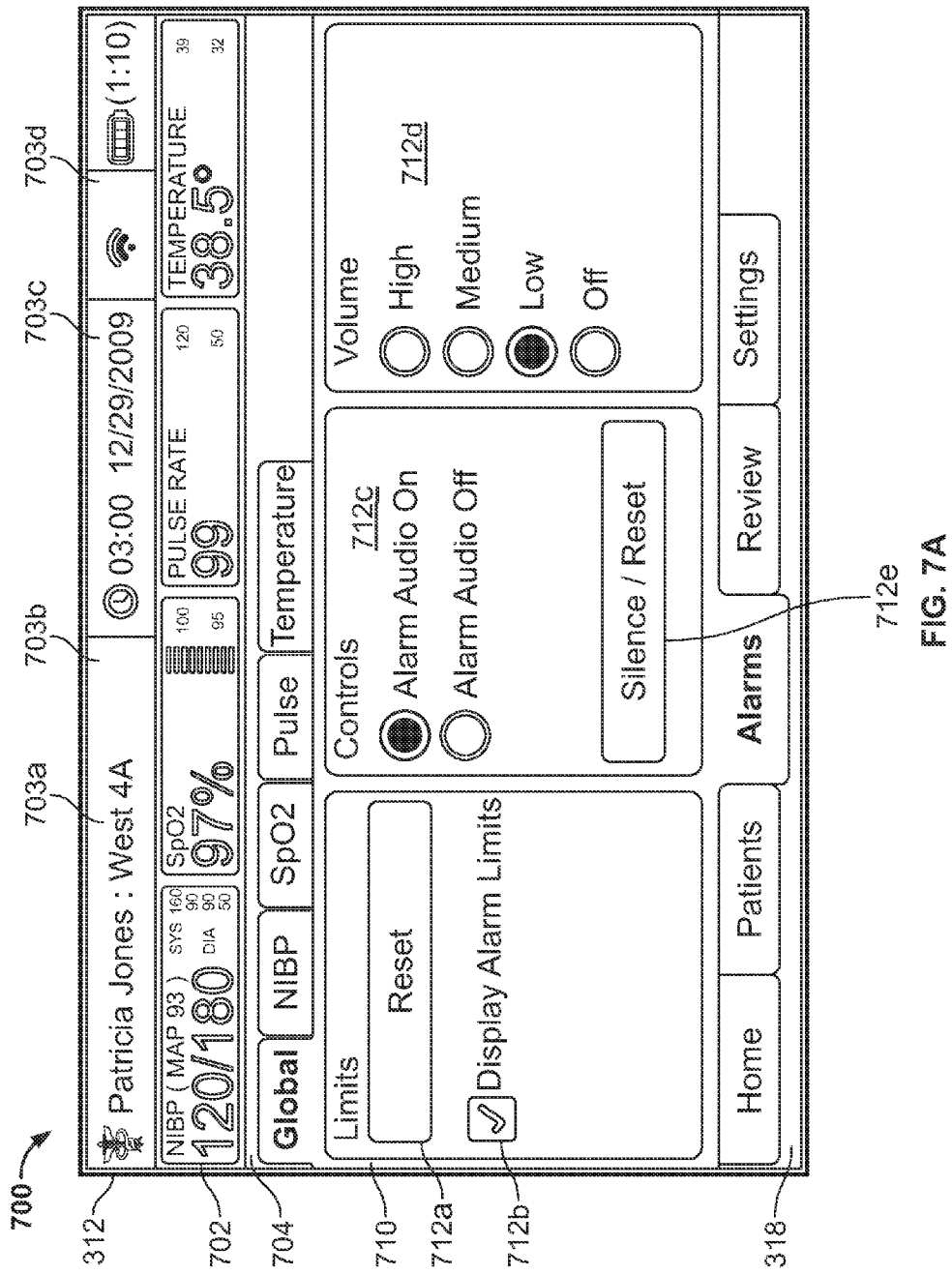
FIG. 7A illustrates an example global pane of an alarms screen.

The alarm status areas 322c, 324a, 326a, 328a act as navigational short cuts to appropriate panes within the alarms screen for each respective physiological parameter (See FIG. 7A). In this way, selecting an alarm status area while no alarm is active results in the PMP device 200 displaying the same user interface as if a user selects the alarms tab 318c and then selects an appropriate pane of the alarms screen. Navigation to the appropriate pane of the alarms screen happens only when the PMP device 200 is not emitting an alarm sound. In other words, the first selection of this area (or anywhere in the parameter reporting frame) would cause the alarm to silence the audio. A subsequent selection of the alarm status area performs the navigation.

Various alarms have various priority levels. For example, an alarm associated with a patient's pulse rate has a high priority level and an alarm associated with detachment of a SpO2 clip has a medium priority level. The PMP device 200 visually and/or sonically indicates alarms having different priority levels in different ways. For example, in some embodiments, when an alarm having a high priority level is active, the PMP device 200 displays visual indications of the alarm in a given color, such as red. When an alarm having a medium or low priority level is active, the PMP device 200 displays visual indications of the alarm in another color, such as yellow. Furthermore, in some embodiments, when an alarm having a high priority level is active, the PMP device 200 emits a given alarm sound, such as a continuous tone. When an alarm having a medium or low priority level is active, the PMP device 200 emits another alarm sound, such as a periodic beep.

When the PMP device 200 is operating in different workflows, the PMP device 200 can activate different alarms and/or emit different alarm sounds. For example, the PMP device 200 activates an alarm when a SpO2 clip detachment event occurs while the PMP device 200 operating within the monitoring workflow, but does not activate the alarm while in a non-operating in the monitoring workflow. This feature can be convenient considering that the PMP device 200 and the patient are more likely to be unattended by a user of the PMP device 200 for periods of time when the PMP device 200 is operating in the monitoring workflow, but less likely when the PMP device 200 is operating in the spot check or the triage workflows. In one embodiment, monitoring of SpO2 may be prevented by the PMP device 200 beyond ten minutes if the PMP device 200 is operating in the spot check or the triage workflows.

Under certain circumstances, multiple alarms can be active concurrently. For example, one alarm can be active because a patient's pulse rate is too high and another alarm can be active because a SpO2 clip has been detached from the patient. When multiple alarms are active concurrently, the PMP device 200 indicates that multiple alarms are active. In various embodiments, the PMP device 200 indicates that multiple alarms are active in various ways. For example, in some embodiments, the alarm message 380 includes an icon that indicates a number of alarms that are currently active. In this example, icon can be a triangle containing the number of alarms that are currently active.

In some embodiments, the PMP device 200 displays different visual indicators depending on the priority levels of concurrently active alarms. For example, when two or more high level alarms are active concurrently, the PMP device 200 displays visual indications for each of the high level alarms. In another example, when an alarm having a medium priority level ("the medium level alarm") and an alarm having a high priority level ("the high level alarm") are active concurrently, the PMP device 200 displays visual indications for the high level alarm and does not display visual indications for the medium level alarm. If the user of the PMP device 200 temporarily silences the alarm sound for the high level alarm, the PMP device 200 does not emit the alarm sound for the high level alarm or the alarm sound for the medium level alarm. When the high level alarm is resolved before the medium level alarm is resolved, the PMP device 200 displays visual indications for the medium level alarm and the PMP device 200 resumes emitting the alarm sound for the medium level alarm.

In some embodiments, the user of the PMP device 200 is able to toggle between multiple concurrently active alarms by selecting one or more controls in the user interface of the PMP device 200 or by selecting one or more buttons on the PMP device 200. In this way, the user causes the PMP device 200 to display the visual indications for each of the multiple concurrently active alarms. For example, a first alarm and a second alarm can be concurrently active. In this example, the PMP device 200 displays an alarm message describing a first alarm. In this example, the PMP device 200 modifies the alarm message to describe a second alarm when a user selects the alarm message.

In some alternative embodiments, the PMP device 200 enables a user to customize the content within the monitoring workflow home screen 300. For example, the PMP device 200 enables a user to adjust the relative sizes of the parameter reporting frames 314a-314d within the monitoring workflow home screen 300. In another example, the PMP device 200 enables the user to add or remove parameter reporting frames from the monitoring workflow home screen 300. Furthermore, in some such embodiments, the PMP device 200 includes one or more predefined templates for the monitoring workflow home screen 300. Each of the predefined templates specifies a predefined set of content within the monitoring workflow home screen 300. For example, one predefined template specifies that the monitoring workflow home screen 300 includes a large parameter reporting frame for the patient's blood pressure and three smaller parameter reporting frames for the patient's pulse rate, SpO2 level, and body temperature. In this example, another predefined template specifies that the monitoring workflow home screen 300 includes only a frame for the patient's SpO2 level and the patient's blood pressure. The user can customize the content within the monitoring workflow home screen 300 by selecting one of these predefined templates or by modifying one of these predefined templates.

FIG. 3C illustrates an example spot check workflow home screen 330. The PMP device 200 displays the spot check workflow home screen 330 when the PMP device 200 is operating in a spot check workflow. The spot check workflow home screen 330 is referred to as the "Home" screen for the spot check workflow. Like when the PMP device 200 is operating in the monitoring workflow, each sensor is physically attached to an identified patient when the PMP device 200 is operating in the spot check workflow. These sensors include a temperature probe, a SpO2 clip, and a NIBP blood pressure cuff. As described elsewhere in this document, the temperature probe, the SpO2 clip and the NIBP blood pressure cuff are peripheral to the PMP device 200.

Also, like the monitoring workflow home screen 300 illustrated in the example of FIG. 3B, the spot check workflow home screen 330 includes a device status area 312, a content area 320, and a navigation area 318. The content area 320 includes a parameter reporting area 314 and a patient attribute area 316. The parameter reporting area 314 of the spot check workflow home screen 330 includes an NIBP frame 334a, a pulse rate frame 314b, a SpO2 frame 334c and a temperature frame 334d.

The NIBP frame 334a contains a representation of a patient's blood pressure. The representation is based on one or more measurements of the blood pressure of a previously identified patient. In the example of FIG. 3C, the NIBP frame 334a includes text representing the patient's systolic and diastolic blood pressure. In the spot check workflow home screen 330, the text representing the patient's systolic and diastolic blood pressure is larger than the text in the monitoring workflow home screen 300 representing the patient's systolic and diastolic blood pressure. The NIBP frame 334a of the spot check workflow home screen 330 does not include the NIBP alarm status area 322c and does not include the NIBP automatic interval timer 322b of the monitoring workflow home screen 300.

The pulse rate frame 334b contains a representation of the patient's pulse rate. The representation is based on one or more measurements of the pulse rate of the patient. In the example of FIG. 3C, the pulse rate frame 334b includes text representing the patient's pulse rate. In the spot check workflow home screen 330, the text representing the patient's pulse rate is larger than the text in the monitoring workflow home screen 300 representing the patient's pulse rate. The pulse rate frame 334b of the spot check workflow home screen 330 does not include the pulse rate alarm status area 324a included within the pulse rate frame 314b of the monitoring workflow home screen 300.

The SpO2 frame 334c contains a representation of the patient's SpO2 level. The representation is based on one or more measurements of the SpO2 level of the patient. In the example of FIG. 3C, the SpO2 frame 334c includes text representing the SpO2 value. In the spot check workflow home screen 330, the text representing the patient's SpO2 level is larger than the text in the monitoring workflow home screen 300 representing the patient's SpO2 level. The SpO2 frame 334c does not include the alarm status area 326a, the SpO2 response time control button 326c, or the SpO2 alarm parameter 326d of the SpO2 frame 314c of the monitoring workflow home screen 300.

The temperature frame 334d contains a representation of the patient's body temperature. The representation is based on one or more measurements of the body temperature of the patient. In the example of FIG. 3C, the temperature frame 334d includes text representing the patient's body temperature. In the spot check workflow home screen 330, the text representing the patient's body temperature is larger than the text in the monitoring workflow home screen 300 representing the patient's body temperature. The temperature frame 334d of the spot check workflow home screen 330 does not include the temperature alarm status area 328a included within the temperature frame 314d of the monitoring workflow home screen 300.

The patient attribute area 316 of the spot check workflow home screen 330 includes text that identifies the patient by name, initials, numerical identifier, or location. In the example of FIG. 3C, the patient attribute area 316 includes text that identifies the patient as "Bar, D." A user is able use the settings screen to configure the PMP device 200 to identify the patient by name or by number. The user is also able to use the settings screen to configure the PMP device 200 not to save or send patient readings when the PMP device 200 does not store information regarding the identity of the patient.

The navigation area 318 of the spot check workflow home screen 330 includes the home tab 318a, the patients tab 318b, the review tab 318d, and the settings tab 318e. The navigation area 318 excludes the alarms tab 318c included in the navigation area 318 of the monitoring workflow home screen 300. As a result, the spot check workflow home screen 330 does not provide direct navigation to the alarms screen as provided by the monitoring workflow home screen 300.

When the PMP device 200 is operating in the spot check workflow, the PMP device 200 locally saves a patient reading and attempts to send the patient reading to another computing node when a user selects the save button 316g. The patient reading includes measurements of the physiological parameters of the patient and data identifying the patient. Unlike when the PMP device 200 is operating in the monitoring workflow, the PMP device 200 clears the spot check workflow home screen 330 when the user selects the save button 316g. When the PMP device 200 clears the spot check workflow home screen 330, the PMP device 200 modifies the spot check workflow home screen 330 such that the spot check workflow home screen 330 no longer contains representations of the physiological parameters of the patient and attributes of the patient.

Because the PMP device 200 clears the spot check workflow home screen 330 when a user selects the save button 316g of the spot check workflow home screen 330, a first identified patient is essentially discharged when the user selects the save button 316g. After selecting the save button 316g, the user selects a second identified patient via the patient selection screen. Upon attaching the sensors to the second identified patient, the PMP device 200 obtains a set of one or more physiological parameter values from the second identified patient.

The spot check workflow is designed for obtaining measurements of physiological parameters from each patient in a series of identified patients. A user selects each patient in the series of identified patients from the patient selection screen. Alternatively, a user can select each patient in the series of identified patient by scanning barcodes of the patients, thereby bypassing the patient selection screen. Further, a user can identify a patient at any step in the workflow prior to saving the patient reading of the spot check workflow home screen 330. Upon attaching the sensors a patient in the series of identified patients, a user uses the PMP device 200 to obtain measurements of one or more physiological parameters of that patient. Typically, the PMP device 200 is attached to a first patient for no more time than is required to obtain one measurement for each of the NIBP, the pulse rate, the SpO2, and the body temperature of the first patient. The user then detaches the sensors from the first patient and attaches the sensors to a second patient that is next in the series of patients.

In one use scenario, a user can use the spot check workflow "making rounds" within a health care facility. For example, a clinician can use the PMP device 200 to obtain one set of measurements of physiological parameters for each patient in a group of twelve patients within a health care facility. Optionally, the clinician can transport the PMP device 200 sequentially to each patient in the group of patients within one "round" of obtaining measurements of physiological parameters. Each "round" of obtaining measurements of physiological parameters can be obtained for each patient in the patients of the group every hour during a working shift.

In some embodiments, the PMP device 200 enables a user to customize the content within the spot check workflow home screen 330. For example, the PMP device 200 enables a user to adjust the relative sizes of the parameter reporting frames 334a-334d within the spot check workflow home screen 330. In another example, the PMP device 200 enables the user to add or remove parameter reporting frames from the spot check workflow home screen 330. Furthermore, in some such embodiments, the PMP device 200 includes one or more predefined templates for the spot check workflow home screen 330. Each of the predefined templates specifies a predefined set of content within the spot check workflow home screen 330. The user can customize the content within the spot check workflow home screen 330 by selecting one of these predefined templates or by modifying one of these predefined templates.

FIG. 3D illustrates an example triage workflow home screen 360. The PMP device 200 displays the triage workflow home screen 360 when the PMP device 200 is in a triage workflow.

Like when the PMP device 200 is operating in the monitoring workflow or the spot check workflow, a user physically attaches each sensor to an unidentified patient when the PMP device 200 is operating in the triage workflow. These sensors include the temperature probe, the SpO2 clip, and the blood pressure cuff that are each attachable to the PMP device 200 as described elsewhere in this document.

The triage workflow home screen 360 includes a device status area 312, a content area 320, and a navigation area 318. The content area 320 of the triage workflow home screen 360 includes a parameter reporting area 314 and a patient attribute area 316. The parameter reporting area 314 of the triage workflow home screen 360 includes an NIBP frame 364a, a pulse rate frame 364b, a SpO2 frame 364c and a temperature frame 364d.

The NIBP frame 364a contains a representation of the systolic and diastolic blood pressure of the patient. The representation is based on one or more measurements of the blood pressure of the patient. In the example of FIG. 3D, the NIBP frame 364a includes text representing the systolic and diastolic blood pressure of the patient. The size of the text in the NIBP frame 364a is similar to the size of the text in the NIBP frame 334a of the spot check workflow home screen 330 and larger than the size of the text in the NIBP frame 314a of the monitoring workflow home screen 300. The NIBP frame 364a does not include the NIBP alarm status area 322c and does not include the NIBP automatic interval timer 322b included in the NIBP frame 314a of the monitoring workflow home screen 300.

The pulse rate frame 364b contains a representation of the pulse rate of the patient. The representation is based on one or more measurements of the pulse rate of the patient. In the example of FIG. 3D, the pulse rate frame 364b contains text representing the pulse rate value of the patient. The size of the text in the pulse rate frame 364b is similar to the size of the text in the pulse rate frame 334b of the spot check workflow home screen 330 and larger than the size of the text in the pulse rate frame 314b of the monitoring workflow home screen 300. The pulse rate frame 364b does not include the pulse rate alarm status area 324a that is included within the pulse rate frame 314b of the monitoring workflow home screen 300.

The SpO2 frame 364c contains a representation of the SpO2 level of the patient. The representation is based on one or more measurements of the SpO2 level of the patient. In the example of FIG. 3D, the SpO2 frame 364c includes text representing the SpO2 value of the patient. The size of the text in the SpO2 frame 364c is similar to the size of the text in the SpO2 frame 334c of the spot check workflow home screen 330 and larger than the size of the text in the SpO2 frame 314c of the monitoring workflow home screen 300. The SpO2 frame 334c does not include the alarm status area 326a, the SpO2 response time control button 326b, or the SpO2 alarm parameter 326b of the SpO2 frame 314c of the monitoring workflow home screen 300.

The temperature frame 364d contains a representation of the body temperature of the patient. The representation is based on one or more measurements of the body temperature of the patient. In the example of FIG. 3D, the temperature frame 364d includes text representing the body temperature of the patient. The size of the text in the temperature frame 364d is similar to the size of the text in the temperature frame 334d of the spot check workflow home screen 330 and larger than the size of the text in the temperature frame 314d of the temperature frame 314d of the monitoring workflow home screen 300. The temperature frame 364d does not include the temperature alarm status area 328a that is included within the temperature frame 314d of the monitoring workflow home screen 300.

The navigation area 318 of the triage workflow home screen 360 includes the home tab 318a, the review tab 318d, and the settings tab 318e. The navigation area 318 of the triage workflow home screen 360 excludes the alarms tab 318c of the monitoring workflow home screen 300. As a result, the triage workflow home screen 360 does not provide direct navigation to the alarms screen as provided by the monitoring workflow home screen 300. Furthermore, the navigation area 318 of the triage workflow home screen 360 excludes the patients tab 318b of the monitoring workflow home screen 300 and the spot check workflow home screen 330. As a result, the triage workflow home screen 360 does not provide direct navigation to the patient selection screen as provided by the monitoring workflow home screen 300 and the spot check workflow home screen 330.

The patient attribute area 316 of the triage workflow home screen 360 includes a patient type button 316b and a save button 316g. The patient attribute area 316 does not include text that identifies the patient.

When the PMP device 200 is operating within the triage workflow, the PMP device 200 locally saves a patient reading of the triage workflow home screen 360. The home screen data of the triage workflow home screen 360 includes measurements of the physiological parameters of the unidentified patient. Furthermore, a user can configure the PMP device 200 to transmit the patient reading of the triage workflow home screen 360 to another computing node in response to a selection of the save button 316g. Unlike the monitoring workflow home screen 300 and like the spot check workflow home screen 330, the PMP device 200 clears the triage workflow home screen 360 when a user selects the save button 316g. When the PMP device 200 clears the triage workflow home screen 360, the PMP device 200 modifies the triage workflow home screen 360 such that the triage workflow home screen 360 no longer contains representations of the physiological parameters of the patient.

When the PMP device 200 is operating in the triage workflow, selection of the patient type button 316b toggles the text label of the patient type button 316b and toggles a value of a patient type parameter within the triage workflow home screen 360. The text label and data value associated with the patient type button 316b, toggles between the label/values of ("Adult"), ("Pediatric") and ("Neonatal").

When the user selects the save button 316g, the patient reading transmitted to another computing node includes a patient type parameter value equal to ("Adult"), ("Pediatric") and ("Neonatal"). The patient type data substitutes for patient identification data that is absent from the patient reading while operating within the triage workflow.

As a result, when the PMP device 200 is operating in the triage workflow, a first unidentified patient is essentially discharged when a user selects the save button 316g. Upon attaching the sensors to a second unidentified patient, the user uses the PMP device 200 to obtain a set of one or more measurements of physiological parameter from the second unidentified patient.

The triage workflow is designed for obtaining measurements of physiological parameters from each of a series of unidentified patients. A user does not select each patient in the series of unidentified patients from the patient selection screen. Instead, the user attaches the sensors to each unidentified patient in sequence. Upon attaching the sensors to a patient in the series of the unidentified patients, the user uses the PMP device 200 to obtain measurements of one or more physiological parameters of that patient at that time. Typically, the user attaches the sensors to the patient for no more time that is required to obtain one measurement for each of the NIBP, the pulse rate, the SpO2 level, and the body temperature of the patient. The user then detaches the sensors are from the patient and attaches the sensors to another patient that is next in the series of patients.

In one use scenario, the triage workflow can be used for obtaining measurements of physiological parameters from unidentified health care recipients. The recipients may or may not be patients of a health care facility. The other computing node is a personal computer which receives the patient reading from the PMP device 200 with no patient names attached.

In some embodiments, the PMP device 200 enables a user to customize the content within the triage workflow home screen 360. For example, the PMP device 200 enables a user to adjust the relative sizes of the parameter reporting frames 364 within the triage workflow home screen 360. In another example, the PMP device 200 enables the user to add or remove parameter reporting frames from the triage workflow home screen 360. Furthermore, in some such embodiments, the PMP device 200 includes one or more predefined templates for the triage workflow home screen 360. Each of the predefined templates specifies a predefined set of content within the triage workflow home screen 360. The user can customize the content within the triage workflow home screen 360 by selecting one of these predefined templates or by modifying one of these predefined templates.

FIG. 4 illustrates an example patient selection screen 400. A user can navigate to the patient selection screen 400 by selecting the patients tab 318b. The patient selection screen 400 includes a device status area 312, a pane selection tab area 310 and a navigation area 318. The pane selection tab area 310 includes four pane selection tabs that are labeled "List", "Summary", "Modifiers" and "Manual." The list pane 418 includes a column label area 412, a patient listing area 414, and a screen control area 416. The device status area 312 appears like the device status area 312 of the monitoring workflow home screen 300, the device status area 312 of the spot check workflow home screen 330, and the device status area 312 of the triage workflow home screen 360. The navigation area 318 appears like the navigation area 318 of the monitoring workflow home screen 300.

The patient listing area 414 includes lines 415a-415e (collectively, "lines 415"). Each of the lines 415 is associated with a different patient. For example, a patient having a name "Barker, D." is listed on the line 415a, a patient having a name "Connor, W." is listed on the line 415c, and a patient having a name "Davison, A" is listed on the line 415e.

The screen control area 416 includes three buttons. A first (left) button that is labeled "Add" is utilized to add a patient to the patient listing area 414. A second (middle) button that is labeled "Delete" is utilized to delete a patient from the patient listing area 414. A third (right) button that is labeled "Select" is utilized to highlight a patient that listed within the patient listing area 414.

FIG. 5 illustrates an example review screen 500. A user can navigate to the review screen 500 using the review tab 318d. The review screen 500 includes a device status area 312, a review table 541, a screen control area 548, and a navigation area 318. The device status area 312 appears like the device status area 312 of the monitoring workflow home screen 300, the device status area 312 of the spot check workflow home screen 330, and the device status area 312 of the triage workflow home screen 360. The navigation area 318 of the review screen 500 appears like the navigation area 318 of the monitoring workflow home screen 300.

The review table 541 includes a column label line 542. In addition, the review table 541 includes patient readings 546a-546f and columns 552a-552i. Each of the patient readings 546a-546f comprises a different set of measurements of physiological parameters of a patient. Each of the columns 552b-552h is associated with a different physiological parameter. Check marks in the column 552a indicate whether particular ones of the patient readings 546a-546f are selected. In the example of FIG. 5, the patient readings 546A and 546e are selected.

For example, the patient reading 546a includes a patient name ("Barker, D.") in the column 552b, a date and time value in the column 552c, a systolic and diastolic measurement value in the column 552d, a mean arterial pressure (MAP) measurement value (not shown), a temperature measurement value in the column 552f, a pulse measurement value in the column 552g, an SpO2 measurement value in the column 552h, and a patient attributes set of values in the column 552i.

The screen control area 548 includes a send patient reading button 548a, a print patient reading button 548b, a delete patient reading button 548c and a view list box 548d. The print patient reading button 548b is utilized to send a selected patient reading. The print patient reading button 548b is utilized to print selected patient readings. The delete patient reading button 548c is utilized to delete selected patient readings. The view list box 548d enables filtering of the review table 541. A user can use the view list box 548d to select to view all available patient readings or only particular patient readings based on sent, unsent or alarm status.

Figure 6A:
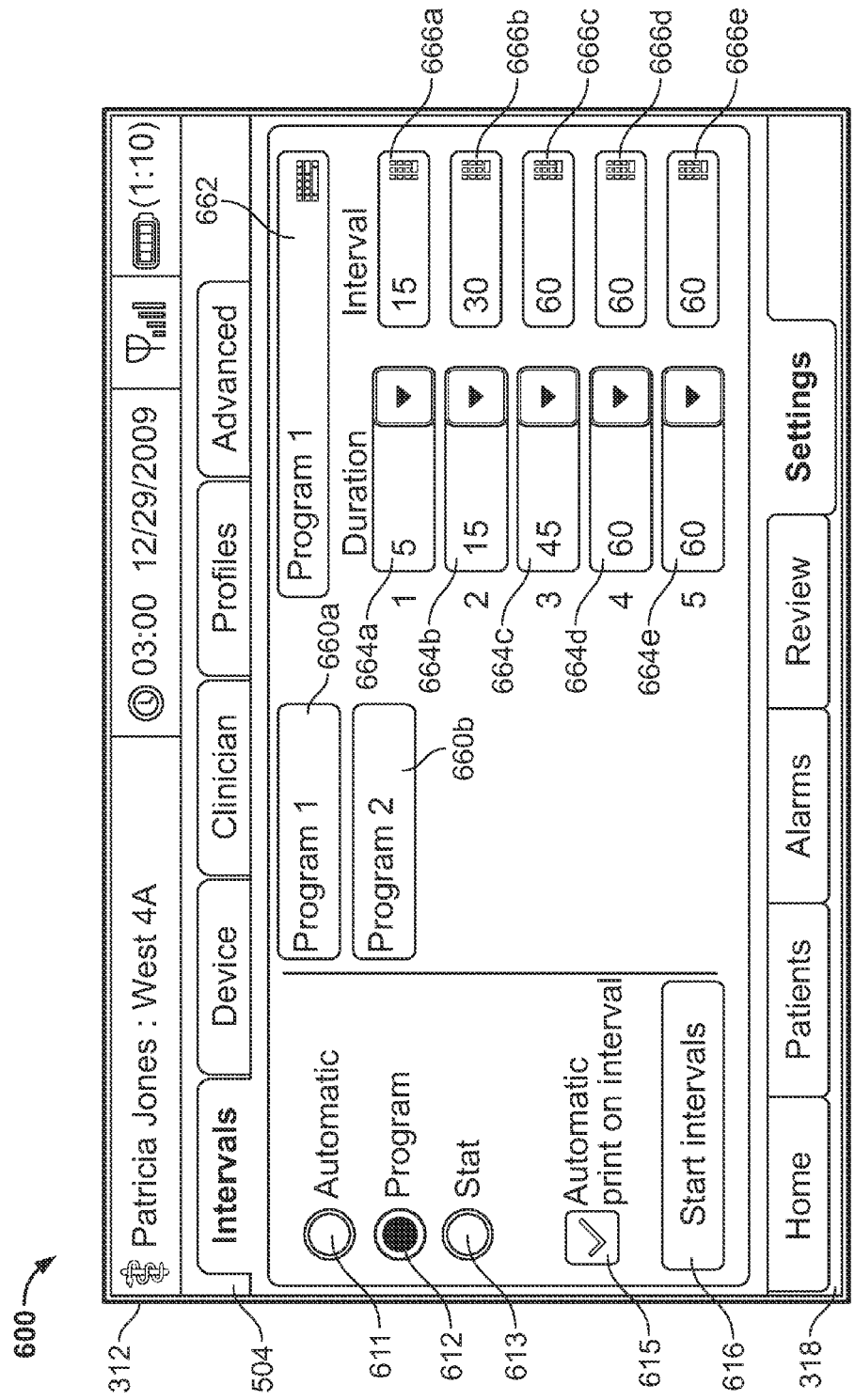
FIG. 6A illustrates an example intervals pane of a settings screen.

FIG. 6A illustrates an example intervals pane 610 of a settings screen 600. Direct navigation to the settings screen 600 is provided from the monitoring workflow home screen 300, from the spot check workflow home screen 330, and from the triage workflow home screen 360. For example, in some embodiments, a user of the PMP device 200 navigates to the settings screen 600 by selecting the settings tab 318e. As illustrated in the example of FIG. 6A, the settings screen 600 includes a device status area 312, a pane selection tab area 604, the intervals pane 610 and a navigation area 318.

The device status area 312 of the settings screen 600 appears like the device status area 312 of the monitoring workflow home screen 300, the device status area 312 of the spot check workflow home screen 330, and the device status area 312 of the triage workflow home screen 360. The pane selection tab area 604 includes five pane selection tabs that are labeled "Intervals," "Device," "Clinician," "Profiles," and "Advanced." The navigation area 318 of the settings screen 600 appears like the navigation area 318 of the monitoring workflow home screen 300.

A user can use the intervals pane 610 to program the PMP device 200 to save NIBP measurements, pulse rate measurements, SpO2 measurements, and temperature measurements for a patient at given intervals over an given time period. Other combinations of physiological parameters can be obtained at other fixed or non-fixed intervals.

The intervals pane 610 includes an automatic control 611, a program control 612, a stat control 613, an off control (not shown), a print control 615, and a start control 616. When the automatic control 611 is selected, the settings screen 600 contains one or more controls for entering a fixed time period to right of control. When the program control 612 is selected, the settings screen 600 contains controls for defining and selecting interval programs. When the stat control 613 is selected, the settings screen 600 contains one or more controls for capturing and saving as many measurements of physiological parameters as possible within a time period, for example a five minute period. When the off control is selected, intervals are turned off. When the print control 615 is selected, a captured measurement at each interval may be printed. The start control 616 is a command button to start the selected interval workflow: Automatic, Program, or Stat. The PMP device 200 automatically initiates an NIBP reading and initiates the interval program once the start control 616 is selected.

In the example of FIG. 6A, the program control 612 is selected. Consequently, the intervals pane 610 includes controls for defining and selecting interval programs. An interval program is a set of parameters that governs the intervals at which the PMP device 200 records measurements of one or more physiological parameters of a patient and for lengths of time for which the PMP device 200 records the measurements of the one or more physiological parameters of the patient.

In the example of FIG. 6A, the intervals pane 610 contains interval program selection controls 660a, 660b (collectively, interval program selection controls 660). More or fewer controls 660 can be provided. The interval program selection controls 660 specify the names of interval programs. In some examples, the interval program selection controls 660 specify names associated with the controls, such as "Transplant," "Transfusion," "Cardiac," which represent names of interval programs.

A user selects an interval program by selecting one of the interval program selection controls 660 that corresponds to the interval program. After selecting the interval program, the user starts the interval program by selecting the start control 616. When the user starts the interval program, the PMP device 200 records measurements of physiological parameters of a patient at the intervals specified by the interval program for the duration specified by the interval program.

In some embodiments, the monitoring workflow home screen 300 contains remaining time controls. The remaining time controls indicate amounts of time remaining before the PMP device 200 records measurements of the physiological parameters. For example, the pulse rate frame 314b of the monitoring workflow home screen 300 can include a remaining time control that indicates that twenty seconds remain before the PMP device 200 records a measurement of the patient's pulse rate. Furthermore, in some embodiments, the PMP device 200 displays the intervals pane 610 when the user selects the remaining time controls. In this way, the user of the PMP device 200 can easily access the intervals pane 610.

Furthermore, in the example of FIG. 6A, the intervals pane 610 contains a program name control 662, duration controls 664a-664e (collectively, "duration controls 664"), and interval controls 666a-666e (collectively, "interval controls 666"). The duration controls 664 and the interval controls 666 are organized into rows. Each row corresponds to a different physiological parameter of the patient. For example, a first row corresponds to the patient's blood pressure, a second row corresponds to the patient's pulse rate, and so on.

When the user selects an interval program using one of the interval program selection controls 660, the program name control 662 contains the name of the interval program. In the example of FIG. 6A, the program name control 662 indicates that the name of the interval program is "Transfusion." The duration controls 664 specify lengths of time during which the PMP device 200 is to record measurements of the physiological parameters. The interval controls 666 specify lengths of time that the PMP device 200 waits between recording measurements of the physiological parameters. In the example of FIG. 6A, the duration control 664a indicates 1 hour and the interval control 666a indicates 15 minutes. Consequently, the PMP device 200 records measurements of a physiological parameter at 15 minute intervals for one hour after the "Transfusion" interval program starts.

When the user selects an interval program using one of the interval program selection controls 660, the user is able to change the values in the program name control 662, the duration controls 664, and the interval controls 666. For example, the user can change the value of the duration control 664b from one hour to two hours.

Figure 6B:
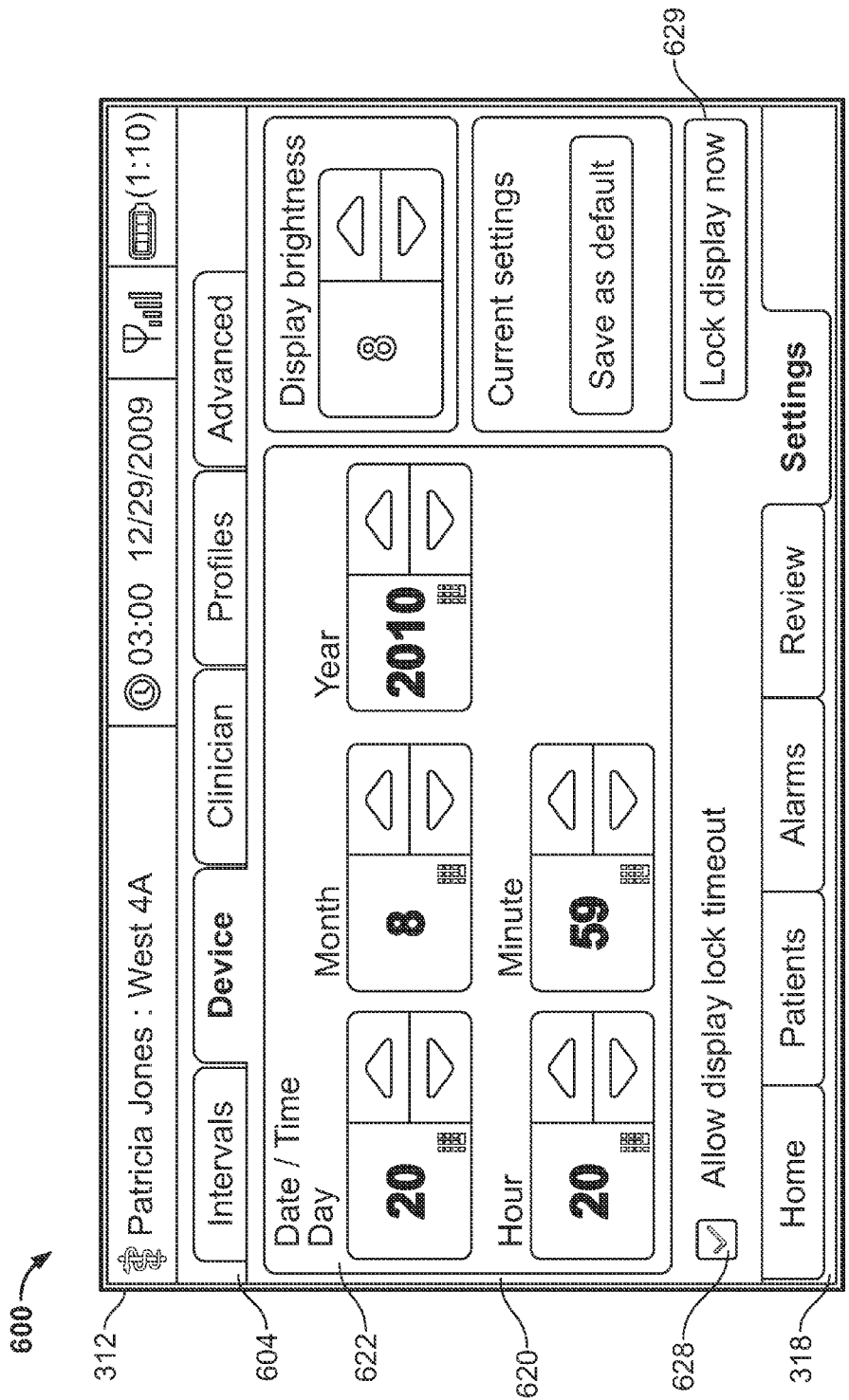
FIG. 6B illustrates an example device pane of the settings screen.

FIG. 6B illustrates an example device pane 620 of the settings screen 600. The settings screen 600 includes a device status area 312, a pane selection tab area 604, a device pane 520 and a navigation area 318. The device status area 312, the pane selection tab area 604, and the navigation area 318 appear like that of FIG. 6A.

The device pane 620 provides controls and information for a user to select or view device characteristics. The device pane 620 includes a set date and time control 622, a touch-screen lock-out control 628, and a command button 629. The set date and time control 622 is configured to set up a date and time for the PMP device 200. A user may select a date display format through the date format selection (not shown), such as MM/DD/YYYY. A user may also select a time zone offset from UTC based on where the PMP device 200 is located. The touch-screen lock-out control 628 is configured to allow a user to lock out the touch screen. When the command button 629 is selected, the touch screen is locked out immediately.

Figure 6C:
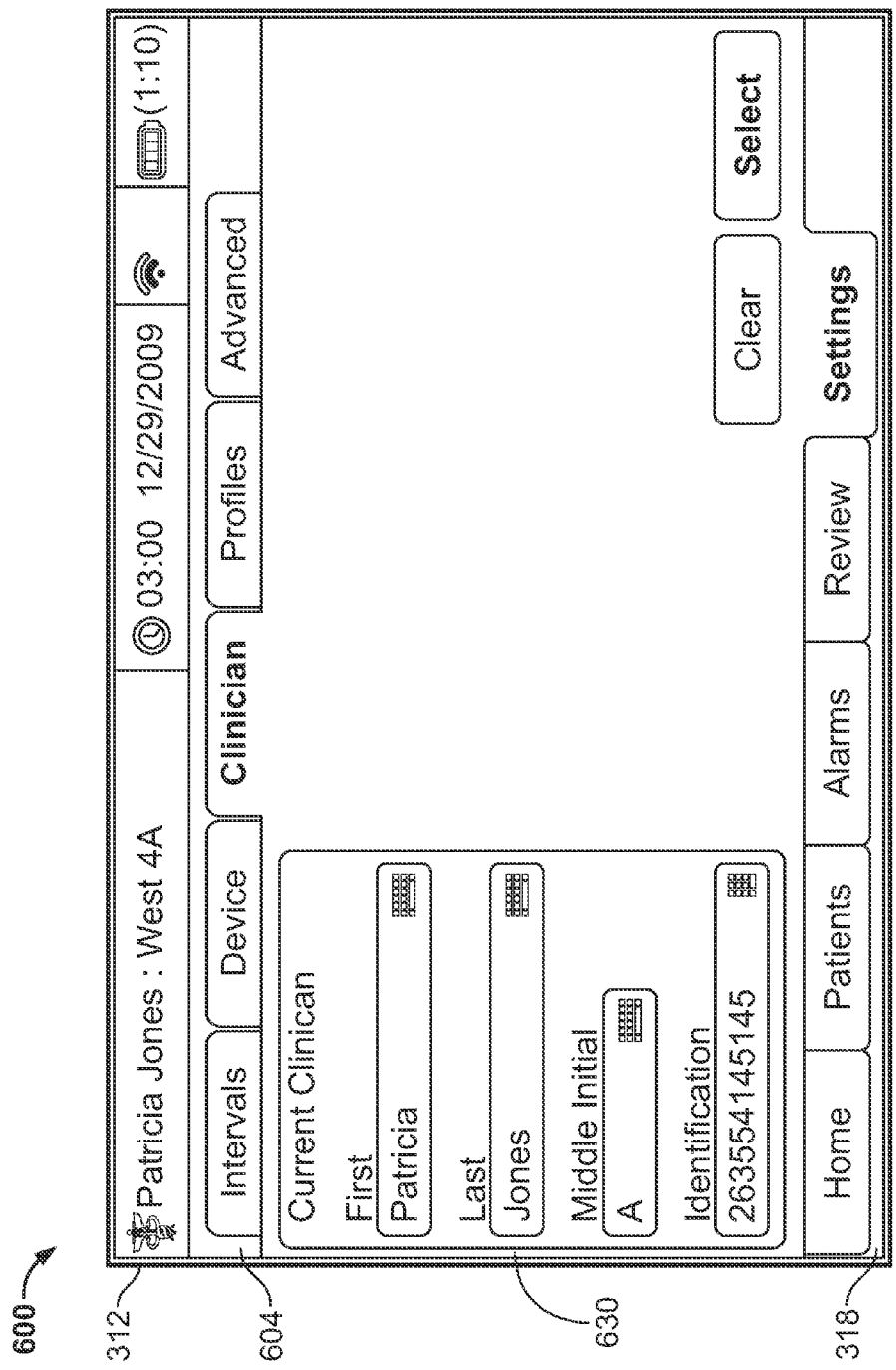
FIG. 6C illustrates an example clinician pane of the settings screen.

FIG. 6C illustrates an example clinician pane of the settings screen 600. The settings screen 600 includes a device status area 312, a pane selection tab area 604, a clinician pane 630 and a navigation area 318. The device status area 312, the pane selection tab area 604 and the navigation area 318 appear like that of FIG. 6A. The clinician pane 630 provides for entry of clinician identification. The clinician identified can include a first name, a last name, a middle initial, and an identification number.

Figure 6D:
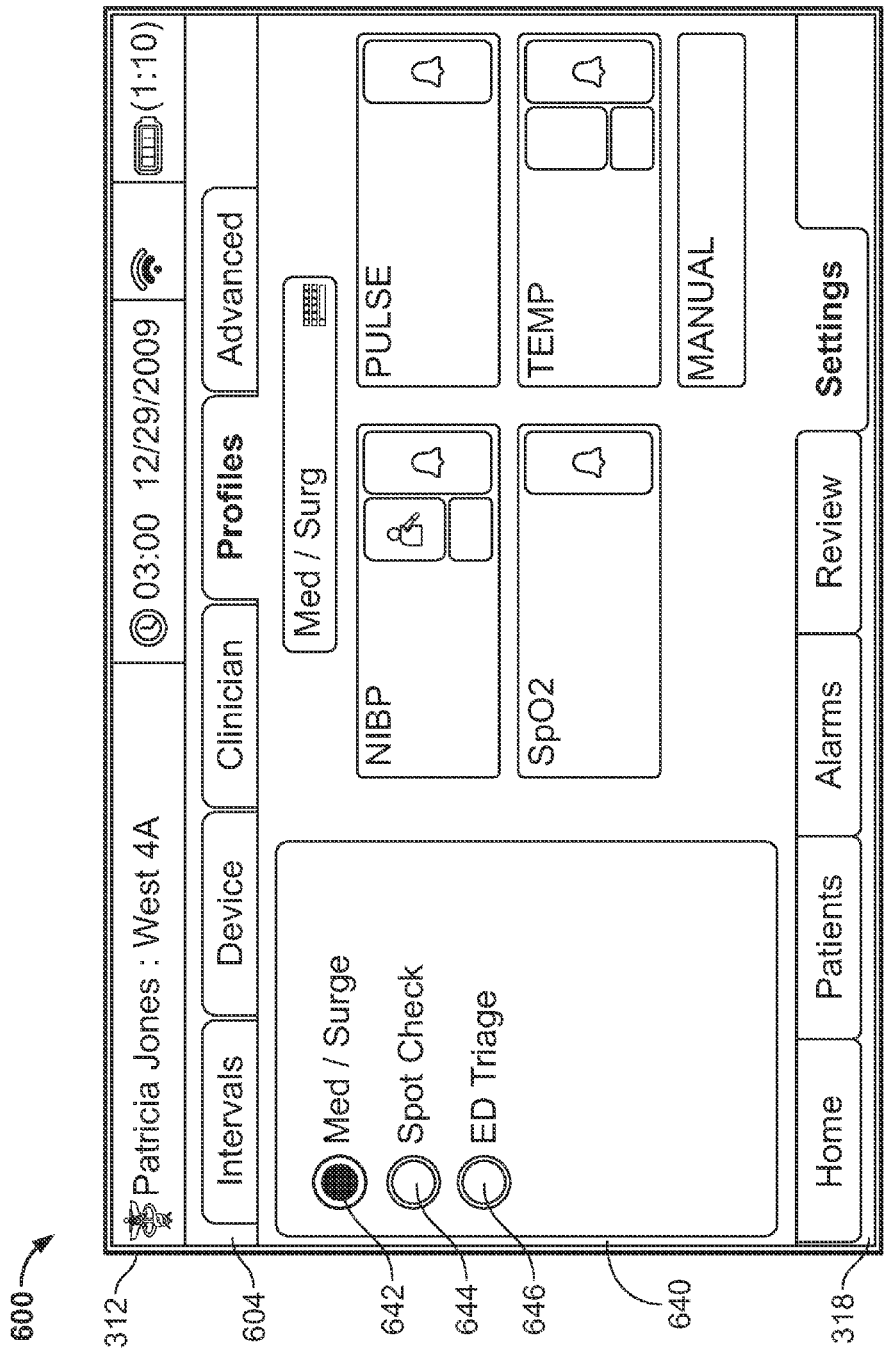
FIGS. 6D-6F illustrate example profile panes of the settings screen.
Figure 6E:
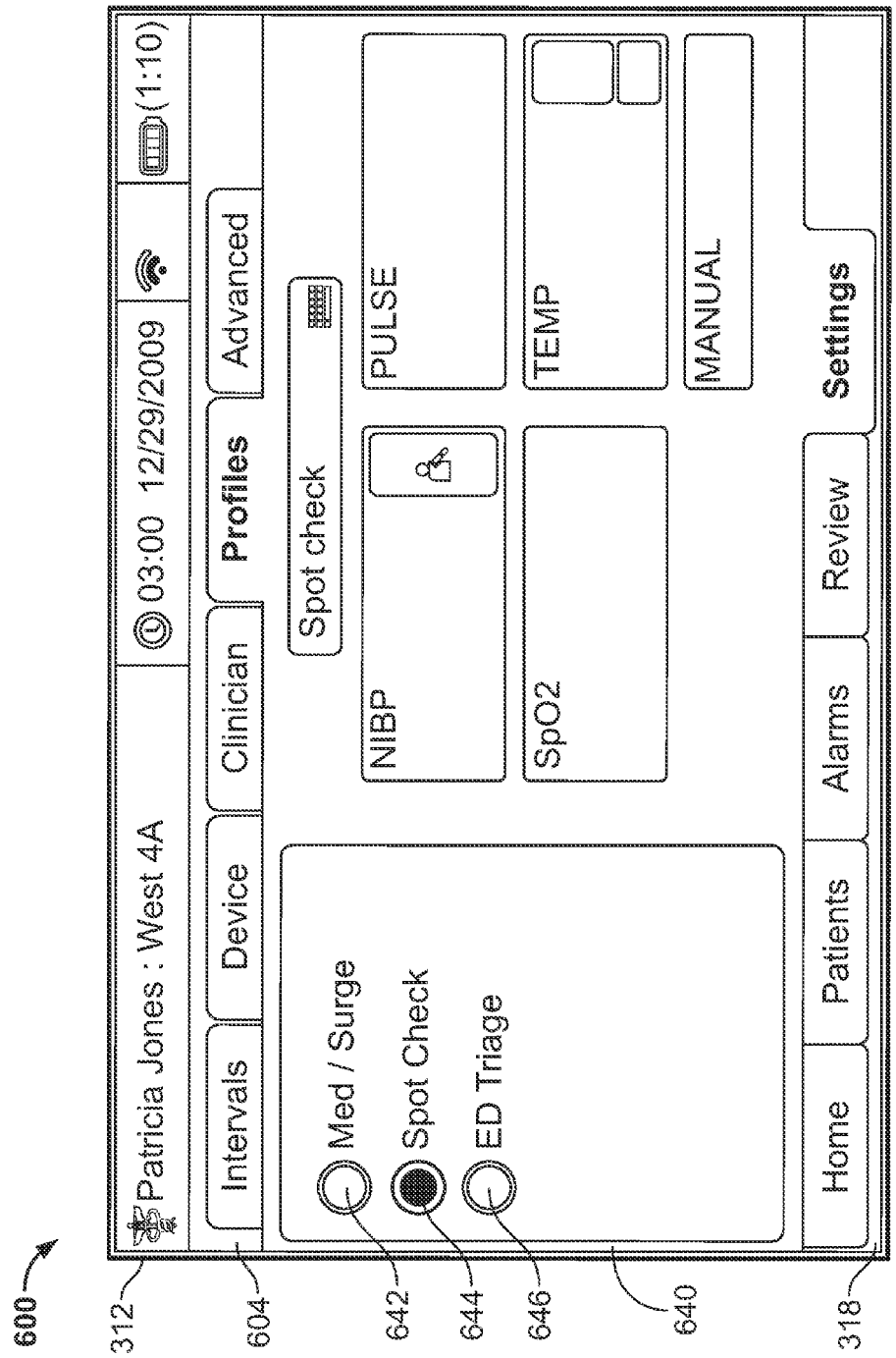
Figure 6F:
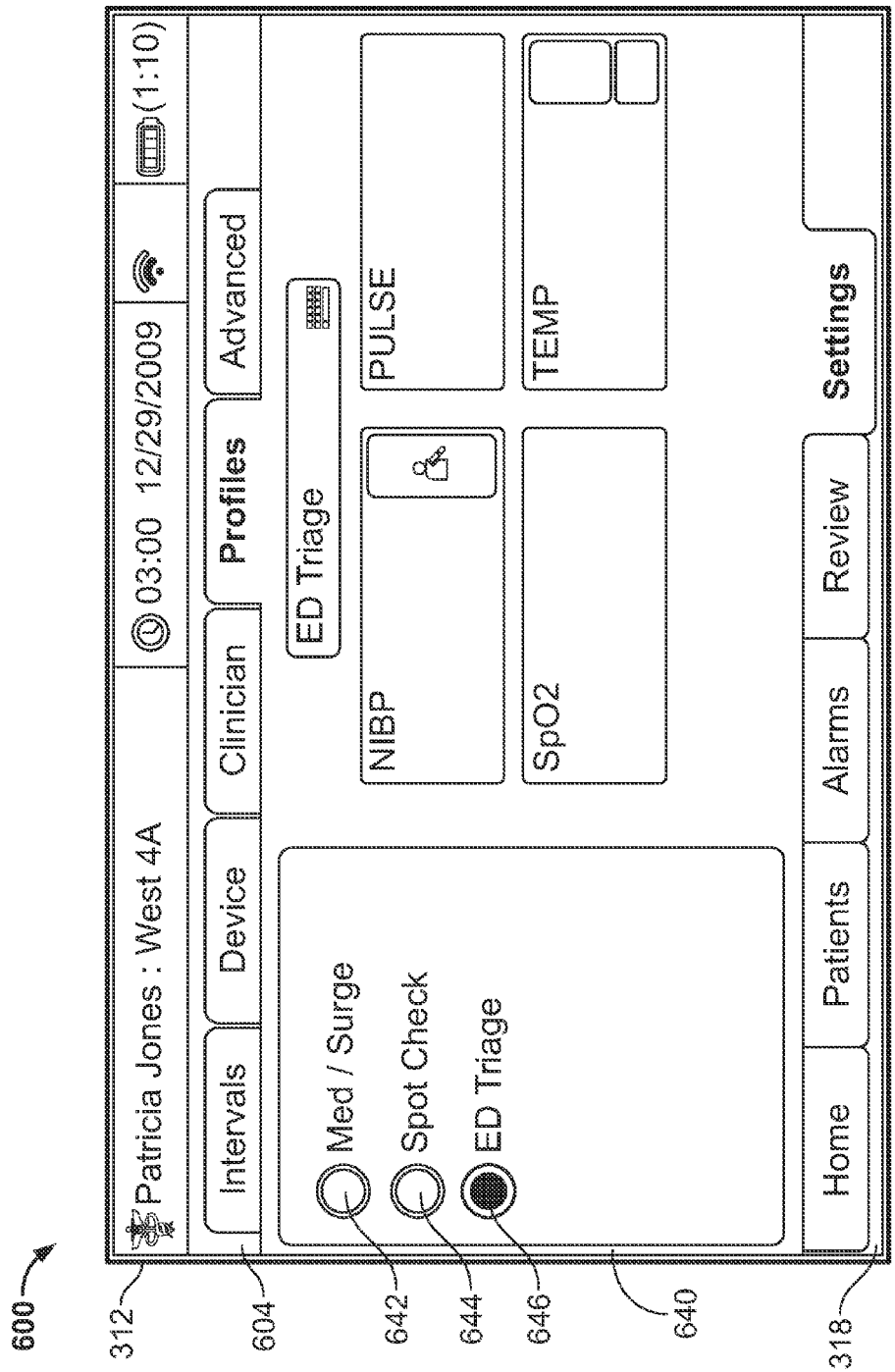

FIGS. 6D-6F illustrate an example profiles pane 640 of the settings screen 600. The settings screen 600 includes the device status area 312, a pane selection tab area 604, the profiles pane 640 and a navigation area 318. The device status area 312, the pane selection tab area 604 and the navigation area 318 appear like that of FIG. 6A. The profiles pane 640 allows a user to select a desired workflow within which the PMP device 200 is to operate. In the examples of FIG. 6D-6F, the profiles pane 640 includes a "Med/Surge" control 642, a "Spot Check" control 644, and an "ED Triage" control 646. A user selects the "Med/Surge" control 642 to select a "Med/Surge" workflow as the workflow in which the PMP device 200 is to operate. The user selects the "Spot Check" control 644 to select the spot check workflow as the workflow in which the PMP device 200 is to operate. The user selects the "ED triage" control 646 to select the triage workflow as the workflow in which the PMP device 200 is to operate. As shown in the examples of FIGS. 6D-6F, the profiles pane 640 shows a preview of the home screen of the selected workflow.

Figure 6G:
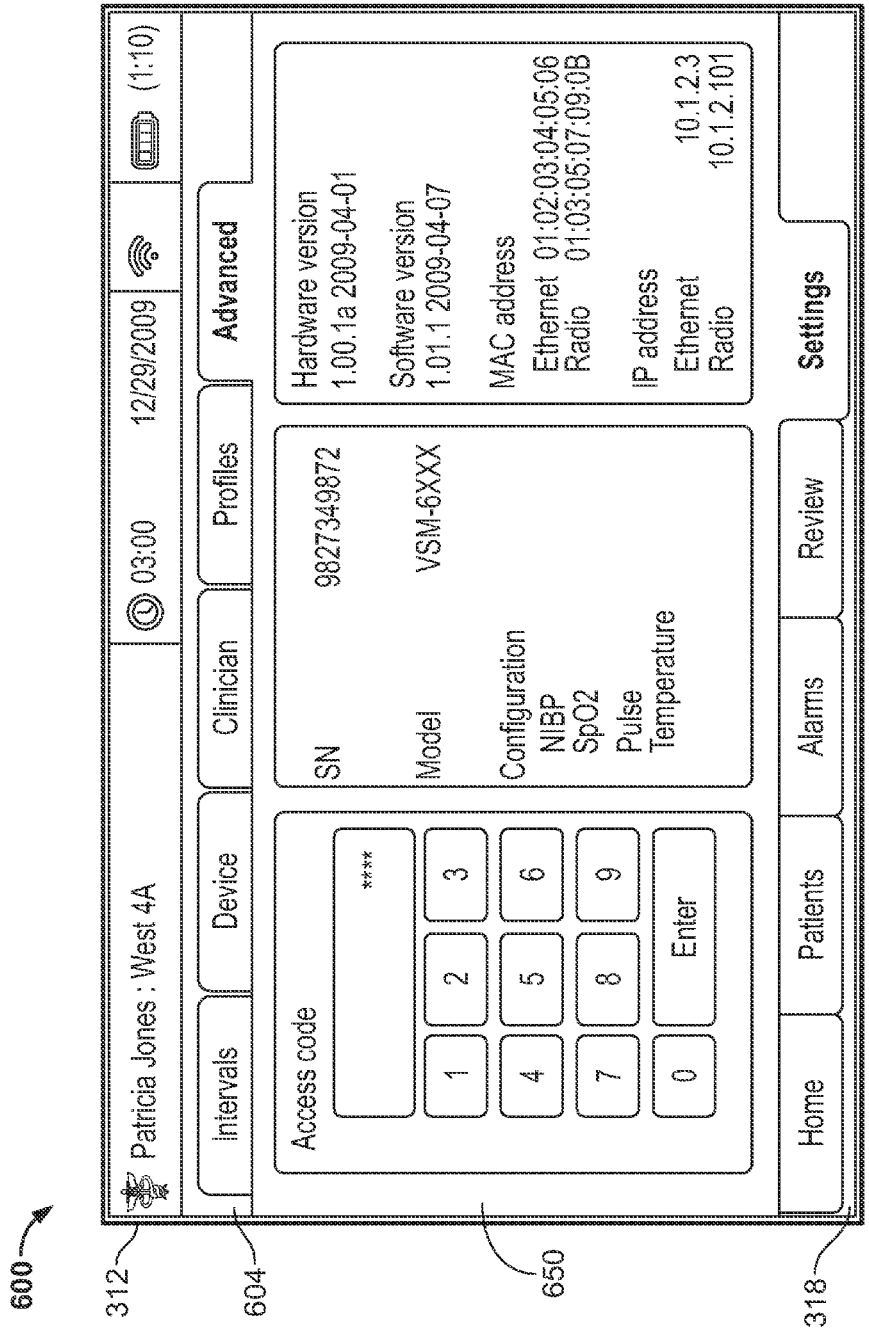
FIG. 6G illustrates an example advanced pane of the settings screen.

FIG. 6G illustrates an example advanced pane 650 of the settings screen 600. The settings screen 600 includes a device status area 312, a pane selection tab area 604, the advanced pane 650 and a navigation area 318. The device status area 312, the pane selection tab area 504 and the navigation area 318 appear like that of FIG. 6A. The advanced pane 650 enables an administrator to access configuration settings that are likely to be set once or less frequently than those required for a normal use. When a proper access code is entered, the PMP device 200 switches to an administration workflow and the navigation tabs switch to advanced settings tabs. The advanced pane 650 also provides read-only information about the PMP device 200.

FIG. 7A illustrates an example global pane 710 of an alarms screen 700. A user of the PMP device 200 navigates to the alarms screen 700 by selecting the alarms tab 318c. The alarms screen 700 includes controls that enable a user to configure global alarm settings and parameter-specific alarm settings.

As illustrated in the example of FIG. 7A, the alarms screen 700 includes the device status area 312, a compressed parameter reporting area 702, a pane selection tab area 704, the global pane 710, and the navigation area 318. The device status area 312 appears like the device status areas of the monitoring workflow home screen 300, the spot check workflow home screen 330 and the triage workflow home screen 360. The navigation area 318 of the alarms screen 700 appears like the navigation area 318 of the monitoring workflow home screen 300.

The compressed parameter reporting area 702 contains one or more compressed parameter frames containing data representing live physiological parameters of a patient. In the example of FIG. 7A, the compressed parameter reporting area 702 contains a compressed NIBP frame 703a, a compressed SpO2 frame 703b, a compressed pulse rate frame 703c, and a compressed temperature frame 703d. The compressed NIBP frame 703a, the compressed SpO2 frame 703b, the compressed pulse rate frame 703c, and the compressed temperature frame 703d are referred to herein collectively as the compressed frames 703. The compressed parameter reporting area 702 has frame dimensions that are smaller than the frame dimensions of the parameter reporting area 314 of the monitoring workflow home screen 300. Because the compressed parameter reporting area 702 is smaller than the parameter reporting area 314, the compressed parameter reporting area 702 appears "squished" relative to the parameter reporting area 314.

The compressed NIBP frame 703a contains a representation of the systolic and the diastolic blood pressure of the patient. The compressed SpO2 frame 703b contains a representation of a SpO2 percentage of the patient, a pulse amplitude blip bar, and alarm limits for the SpO2 parameter. The compressed pulse rate frame 703c contains a representation of a pulse rate of the patient. The compressed temperature frame 703d contains a representation of the body temperature of the patient. In the example of FIG. 7A, the compressed frames 703 do not contain user-selectable controls. Consequently, the user is unable to toggle views of the physiological parameters from the compressed frames 703.

When an alarm associated with one of the physiological parameters is active, the corresponding one of the compressed frames 703 provides a visual indication of the alarm. For example, when the patient's blood pressure is too high, a perimeter of the compressed NIBP frame 703a changes from one color (e.g., gray) to a different color (e.g., red). Furthermore, when an alarm is active, the device status area 312 of the alarms screen 700 is replaced by an alarm message describing the alarm. In some embodiments, selecting the alarm message causes the PMP device 200 to temporarily stop emitting an alarm sound associated with the alarm.

The pane selection tab area 704 includes five pane selection tabs that are labeled "Global", "NIBP", "SpO2", "Pulse" and "Temperature." When the user selects one of the pane selection tabs in the pane selection tab area 704, the PMP device 200 updates the alarms screen 700 to contain a pane associated with the selected pane selection tab.

The global pane 710 is located below the compressed parameter reporting area 702. The global pane 710 provides controls for configuring global alarm settings for the PMP device 200. The global alarm settings are settings that apply to all alarms provided by the PMP device 200. In the example of FIG. 7A, the global pane 710 includes a reset button 712a, a display alarm limit parameter button 712b, a set of alarm audio buttons 712c, a set of volume buttons 712d, and a silence/reset button 712e. A user can use the reset button 712a to reset alarm limits. The user can use the display alarm limit parameter button 712b to configure the PMP device 200 to display or not to display alarm limits. The user can use the set of alarm audio buttons 712c to configure the PMP device 200 to emit alarm sounds. The user can use the set of volume buttons 712d to set a volume of the alarm sounds to high, medium or low. Also, the user can use the silence/reset button 712e to silence or reset alarms.

Figure 7B:
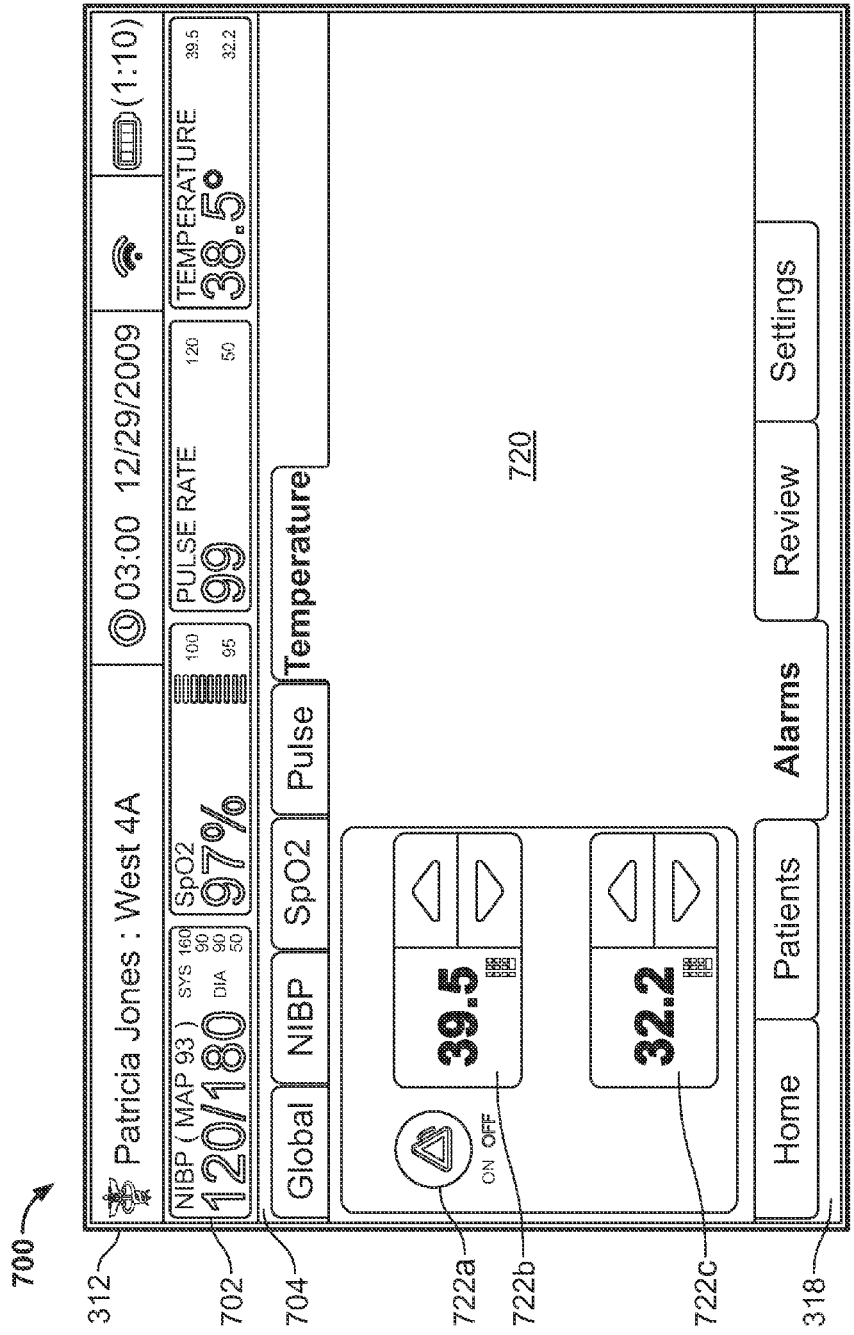
FIG. 7B illustrates an example temperature pane of the alarms screen.

FIG. 7B illustrates an example temperature pane 720 of the alarms screen 700. The alarms screen 700 includes the device status area 312, the compressed parameter reporting area 702, the pane selection tab area 704, the temperature pane 720, and a navigation area 318. The device status area 312, the compressed parameter reporting area 702, the pane selection tab area 704 and the navigation area 318 appear like that of FIG. 7A.

The temperature pane 720 is located below the compressed parameter reporting area 702. The temperature pane 720 enables a user of the PMP device 200 to configure parameter-specific alarm settings for the temperature alarm. In the example of FIG. 7B, the temperature pane 720 provides controls 722a, 722b and 722c. The control 722a sets the temperature alarm to ON or OFF. The control 722b sets an upper temperature limit for the temperature alarm. The control 722c sets a lower temperature limit for the temperature alarm.

Figure 7C:
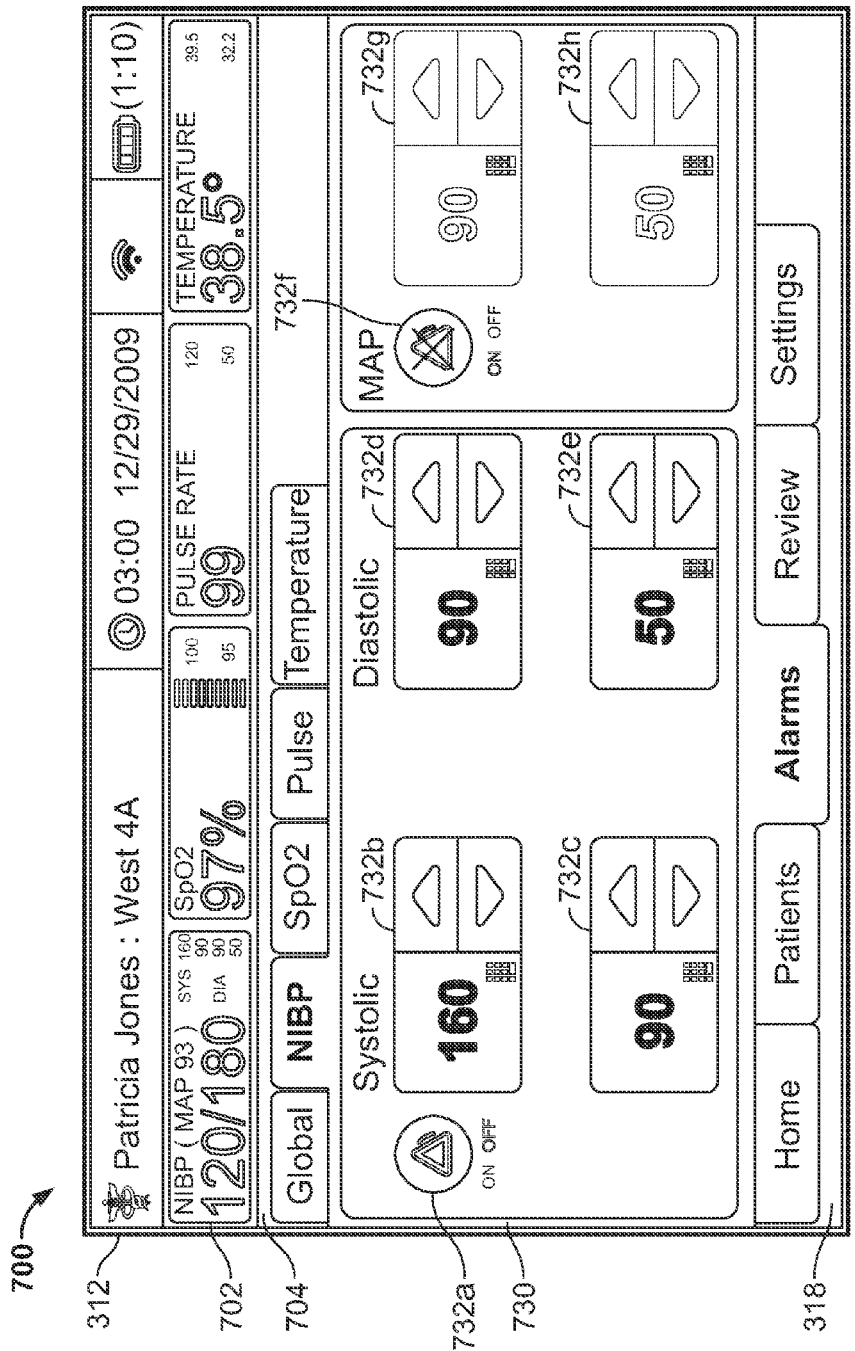
FIG. 7C illustrates an example NIBP pane of the alarms screen.

FIG. 7C illustrates an example NIBP pane 730 of the alarms screen 700. The alarms screen 700 includes a device status area 312, a compressed parameter reporting area 702, a pane selection tab area 704, the NIBP pane 730, and a navigation area 318. The device status area 312, the compressed parameter reporting area 702, the pane selection tab area 704 and the navigation area 318 appear like that of FIG. 7A.

The NIBP pane 730 enables a user of the PMP device 200 to configure parameter-specific alarm settings for the NIBP alarm. In the example of FIG. 7C, the NIBP pane 730 contains a control 732a to set the systolic and diastolic alarm ON or OFF. The NIBP pane 730 also contains controls 732b-732e to set the systolic and diastolic upper and lower alarm limits for the systolic and diastolic alarm. Further, the NIBP pane 730 provides controls 732f, 732g and 732h. The control 732f sets a MAP alarm to ON or OFF. The control 732g sets set an upper MAP limit for the MAP alarm. The control 732h sets a lower MAP limit for the MAP alarm.

Figure 7D:
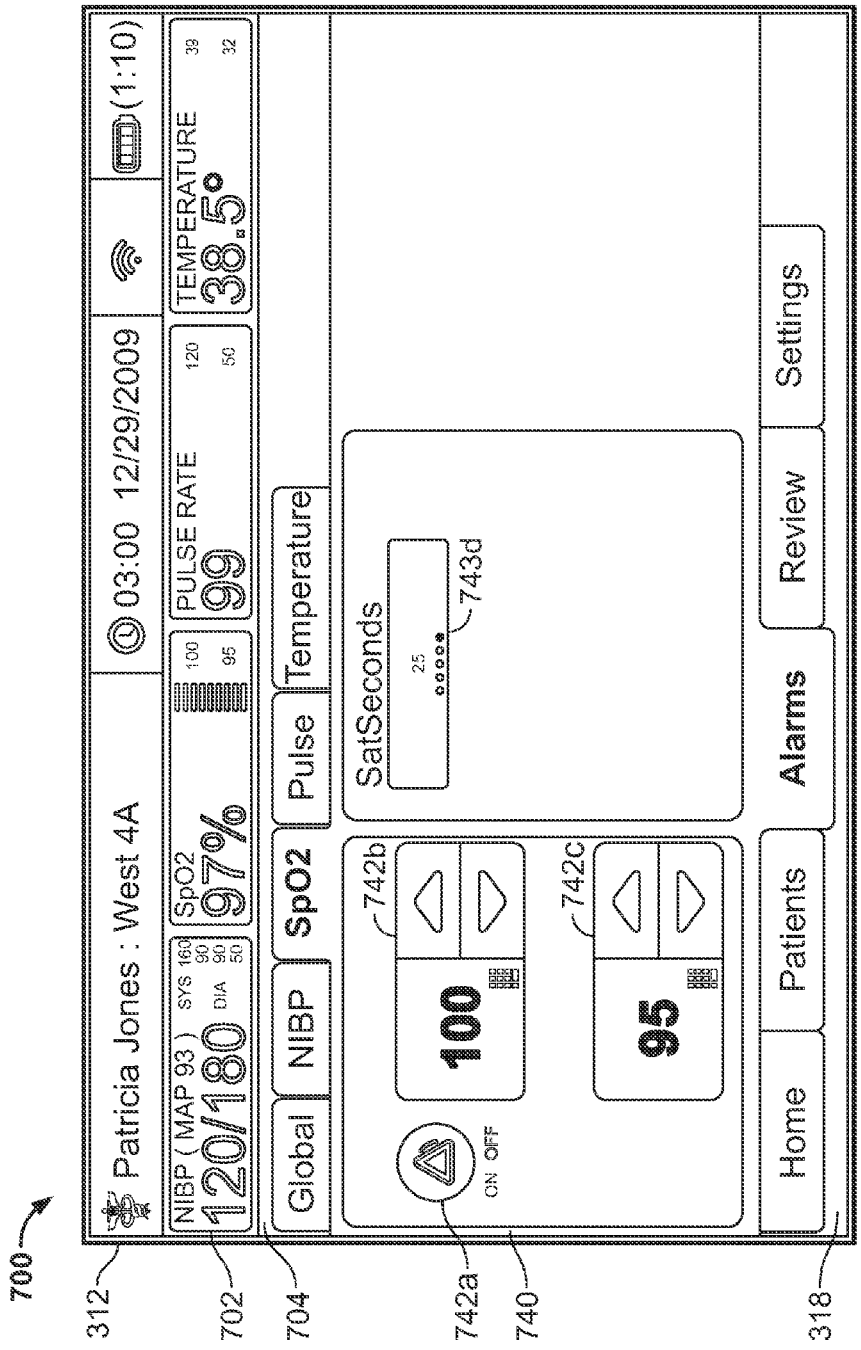
FIG. 7D illustrates an example SpO2 pane of the alarms screen.

FIG. 7D illustrates an example SpO2 pane 740 of the alarms screen 700. The alarms screen 700 includes the device status area 312, the compressed parameter reporting area 702, the pane selection tab area 704, the SpO2 pane 740, and the navigation area 318. The device status area 312, the compressed parameter reporting area 702, the pane selection tab area 704, and the navigation area 318 appear like that of FIG. 7A.

The SpO2 pane 740 enables a user of the PMP device 200 to configure parameter-specific alarm settings for the SpO2 alarm. In the example of FIG. 7D, the SpO2 pane 740 provides controls 742a, 742b and 742c. The control 742a sets the SpO2 alarm to ON or OFF. The controls 742b and 742c set an upper SpO2 limit and a lower SpO2 limit for the SpO2 alarm. The SpO2 pane 740 also includes a SatSeconds™ control 743d. When a numeric value is selected, an SpO2 alarm is not activated until a length of time specified by the SatSeconds control 743d has expired. The length of time specified by the SatSeconds control 743d is based on a duration of a low SpO2 event multiplied by a number of percentage points that the patient's SpO2 falls outside the lower SpO2 alarm threshold. Also, the SatSeconds control 743d appears next to the controls 742b and 742c when the control 742a is set to ON. However, when the control 742a is set to OFF, the SatSeconds control 743d is not displayed and the alarm condition is not delayed per a SatSeconds algorithm.

Figure 7E:
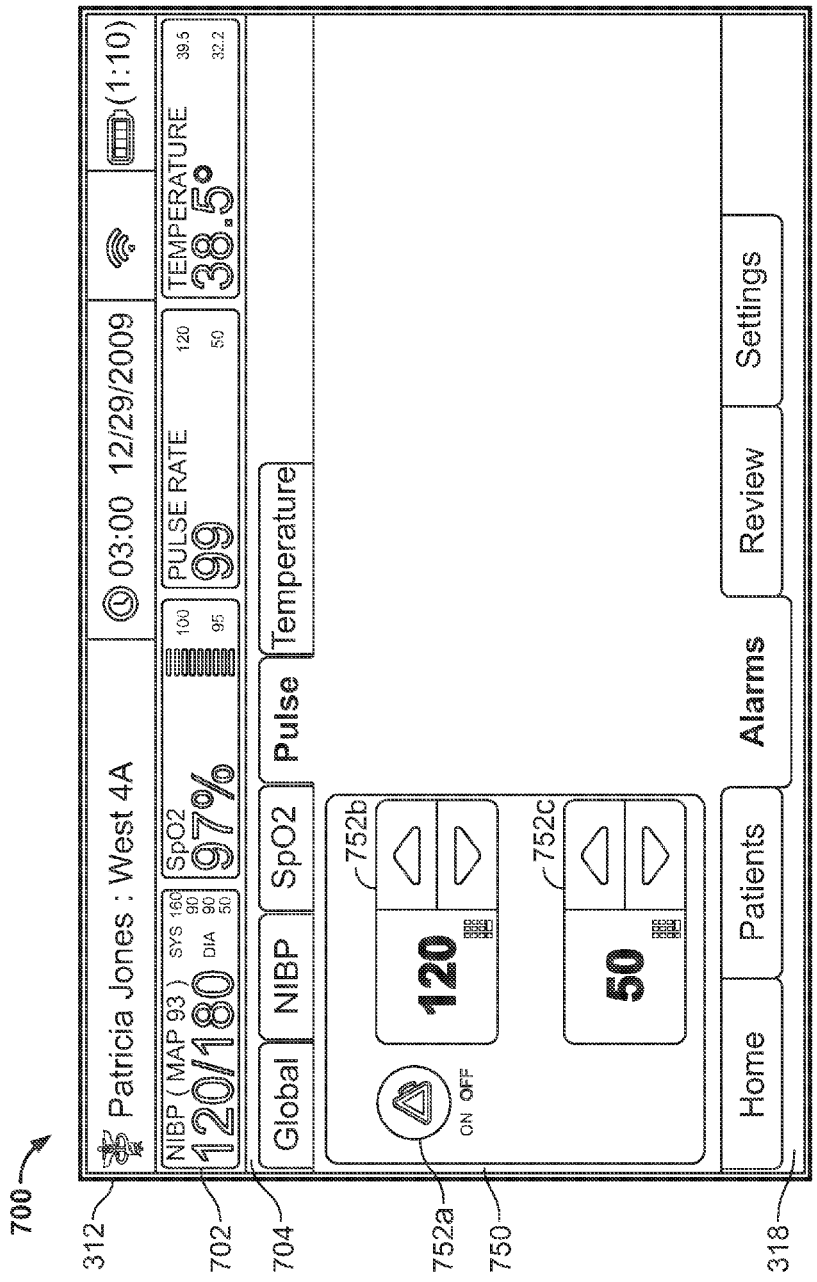
FIG. 7E illustrates an example pulse rate pane of the alarms screen.

FIG. 7E illustrates an example pulse rate pane 750 of the alarms screen 700. The alarms screen 700 includes the device status area 312, the compressed parameter reporting area 702, the pane selection tab area 704, the pulse rate pane 750 and the navigation area 318. The device status area 312, the compressed parameter reporting area 702, the pane selection tab area 704 and the navigation area 318 appear like that of FIG. 7A.

The pulse rate pane 750 enables a user of the PMP device 200 to configure parameter-specific alarm settings for the pulse rate alarm. In the example of FIG. 7E, the pulse rate pane 750 provides an on/off control 752a, an upper limit control 752b and a lower limit control 752c. The on/off control 752a allows a user to turn the pulse rate alarm on or off. The upper limit control 752b allows a user to set an upper pulse rate limit for the pulse rate alarm. The lower limit control 752c allows a user to set a lower pulse rate limit for the pulse rate alarm.

The upper limit control 752b includes a numerical portion, an up button and a down button. The numerical portion of the upper limit control 752b specifies an upper pulse rate limit for the pulse rate alarm. Selecting the up button of the upper limit control 752b incrementally increases the upper pulse rate limit. Selecting the down button of the upper limit control 752b incrementally decreases the upper pulse rate limit. Selecting the numerical portion of the upper limit control 752b causes the PMP device 200 to display a numerical keypad. The user is able to use the numerical keypad to manually enter a value for the upper pulse rate limit.

The lower limit control 752c includes a numerical portion, an up button, and a down button. The numerical portion of the lower limit control 752c specifies the lower pulse rate limit. Selecting the up button of the lower limit control 752c incrementally increases the lower pulse rate limit. Selecting the down button of the lower limit control 752c incrementally decreases the lower pulse rate limit. Selecting the numerical portion of the lower limit control 752c causes the PMP device 200 to display a numerical keypad. The user is able to use the numerical keypad to manually enter a value for the lower pulse rate limit.

In the examples shown, the values that are entered by the user are validated for accuracy. For example, upper and lower thresholds for each parameter can be set. If the user selects a value outside of the upper and lower thresholds, the system can prevent such a selection and/or alert the user. For example, if the user types in 300 minutes on the keypad for a parameter, and the upper threshold set for that parameter is 240 minutes, the system will not allow the user to increase the parameter to 300 minutes.

In some embodiments, various panes of the alarms screen 700 can include other upper limit controls and other lower limit controls like the upper limit control 752b and the lower limit control 752c. The other upper limit controls and the other lower limit controls allow a user to set upper limits and lower limits for alarms for various physiological parameters of patients.

When the PMP device 200 is in a continuous workflow mode, the home screen 250 can display the information described above. Such information can include continuous measurements, such as SpO2, PR, etCO2, FiCO2, IPI, RR and/or SpHb.

The pulse rate can be obtained from two sources, an SpO2 or NIBP reading, with the reading from SpO2 having higher priority for display. If SpO2 readings are available, then pulse rate is displayed and updated once per second with SpO2 as the source. If no SpO2 readings are available and an NIBP reading is started, then the pulse rate is cleared when the NIBP frame is cleared and then updated with a pulse rate from NIBP when it is available, likely when systolic/diastolic is available, with NIBP as the source. Such a reading would be episodic, as described below.

Figure 8:
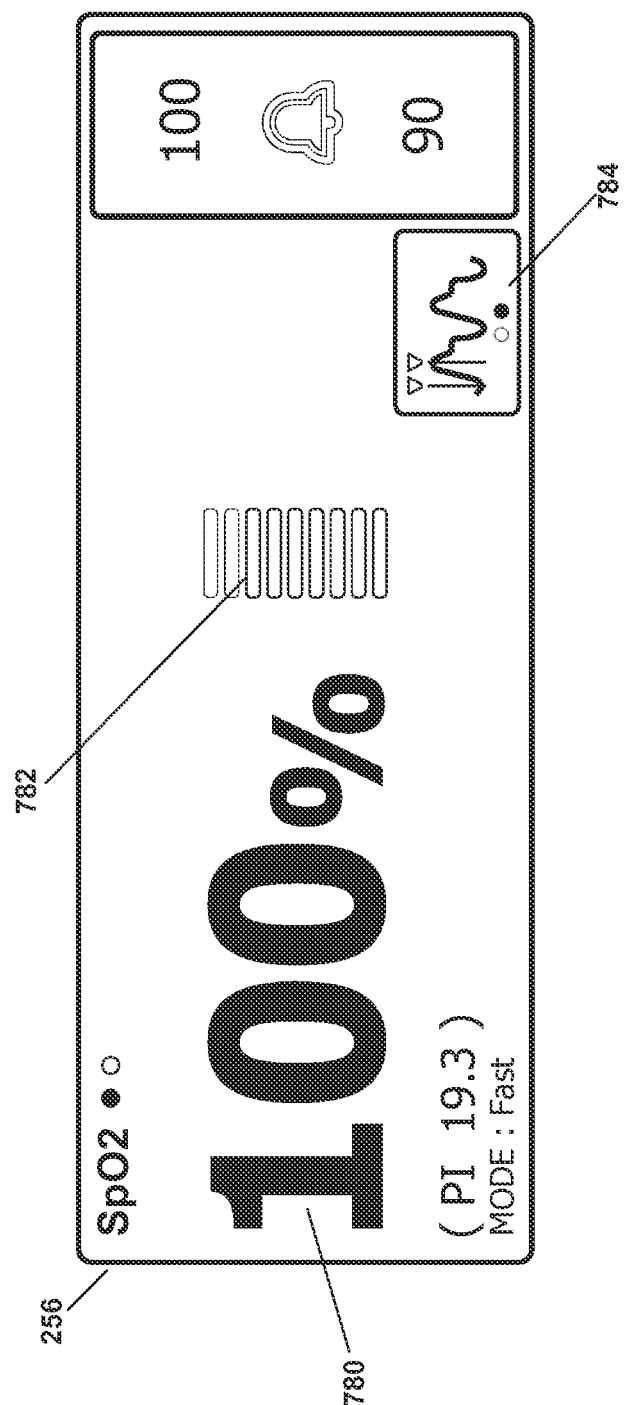
FIG. 8 illustrates an example SpO2 frame of the continuous workflow home screen.

Referring to FIG. 8, the SpO2 frame 256 is shown. The SpO2 frame 256 provides a variety of information, such as a percentage SpO2 780 (e.g., "100%").

In addition, a pulse amplitude blip bar 782 is shown. The pulse amplitude blip bar 782 indicates a pulse beat of the patient and shows the relative pulse amplitude. As the detected pulse becomes stronger, more bars light up with each pulse. The example pulse amplitude blip bar 782 provides 9 bars, and blip values are divided equally into the number of bars. Brighter, more visually intense bars indicate values received from the SpO2 sensor, and their growth vertically up the bar indicates greater levels of strength. Remaining bars are indicated as darker, less prominent, inactive bars. All the bars are displayed darker when no SpO2 activity or signal is available.

In addition, a plethysmographic waveform 784 is shown. The plethysmographic waveform 784 can be selected by the user to provide a larger representation of the waveform. The plethysmographic waveform 784 provides the real-time sensor signal. It allows a user to observe the relative pulsatile strength and quality of the incoming signal. The waveform is displayed per configured sweep speed, which appears above and to right side of waveform display area (except when the smallest frame size for continuous profile is displayed—in this case the sweep speed may not be displayed).

Figure 9:
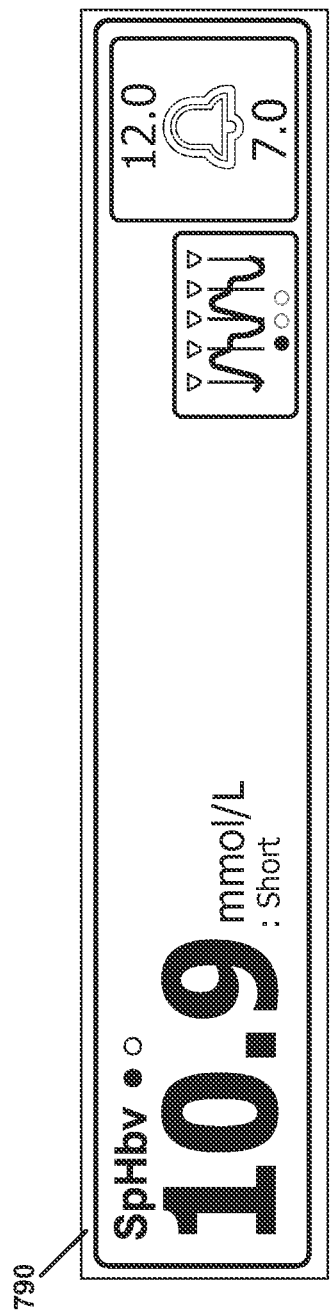
FIG. 9 illustrates an example SpHb frame of the continuous workflow home screen.

Referring to FIG. 9, an example SpHb (measuring total hemoglobin concentration in blood) frame 790 is shown, which presents measures associated with total hemoglobin readings. In this example, the SpHb frame 790 shows the current SpHb reading (e.g., "10.9"), along with alarm limits (e.g., "7.0" to "12.0"). An SpHb trend graphic provides a historical view of total hemoglobin readings over the displayed view time. Selection of the graphic on the SpHb frame 790 provides a larger trend graphic illustrating the change over time with the upper and lower limits set as the configured alarm limits.

Figure 10A:
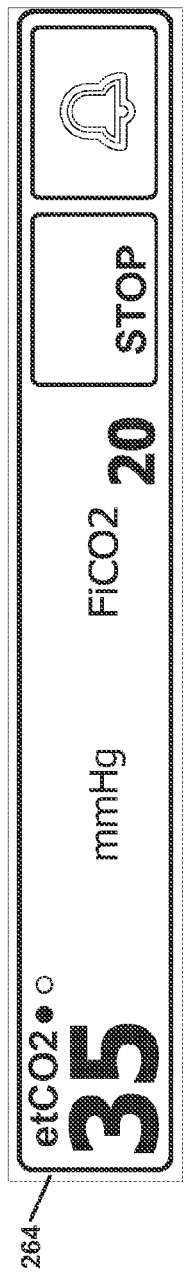
FIGS. 10A-10B illustrate an example etCO2 frame of the continuous workflow home screen.
Figure 10B:
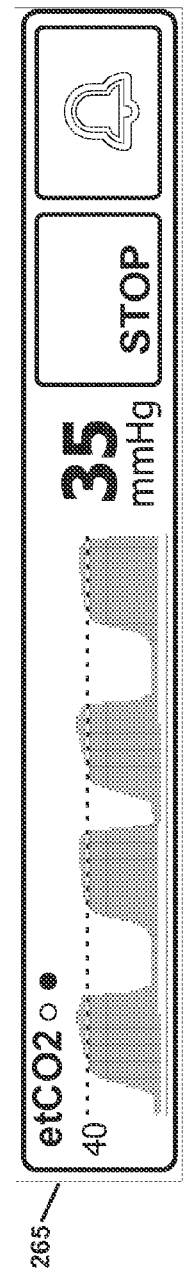

Referring to FIGS. 10A-10B, the etCO2 frame 264 displays data, information, and controls relevant for etCO2 and FiCO2 readings capture, as well as a CO2 waveform. The etCO2 frame 264 provides views with text and graphics, including a Capnogram waveform.

When the Capnogram is selected, the waveform frame 265 is shown, including real-time sensor signal. It allows a user to observe the breathing patterns of the patient for instant determination of adequate ventilation versus hyper/hypo ventilation conditions. The waveform is displayed per the default sweep speed, which appears above and to right side of waveform display area.

Figure 11A:
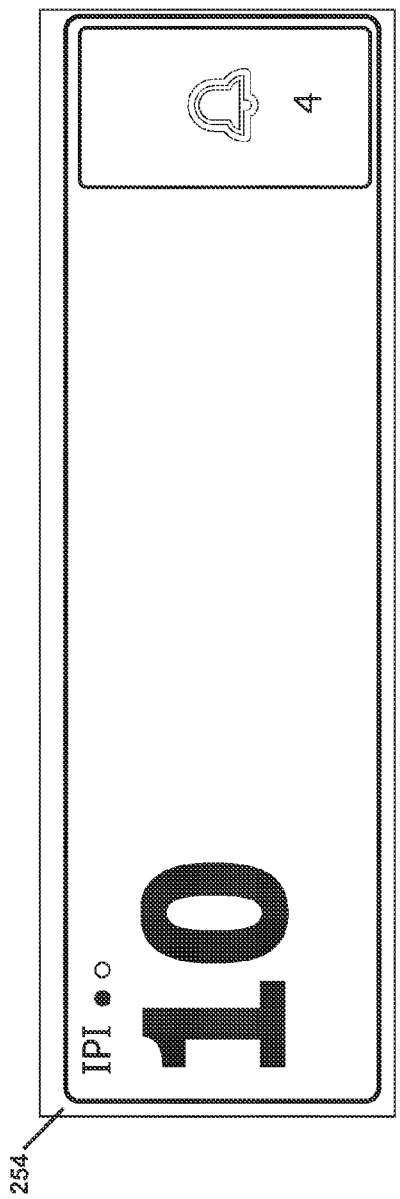
FIGS. 11A-11B illustrate an example IPI frame of the continuous workflow home screen.
Figure 11B:
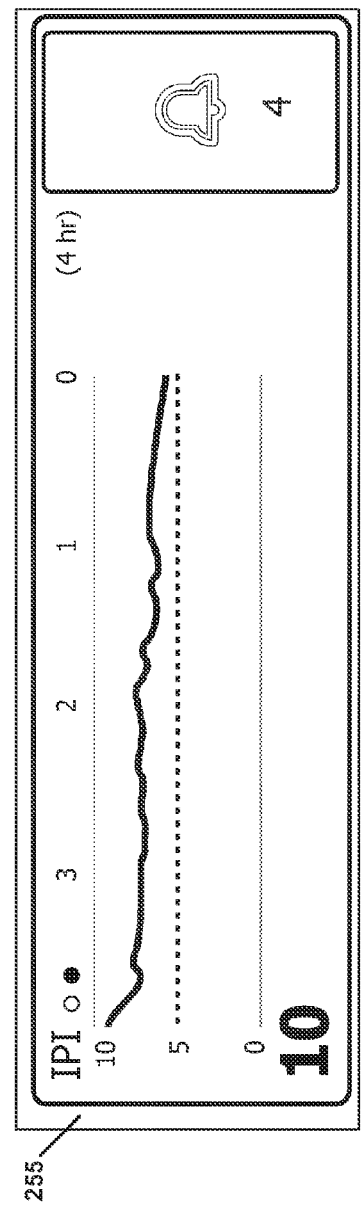

Referring now to FIGS. 11A-11B, the IPI frame 254 encapsulates data, information, and controls relevant for display of IPI readings calculated using CO2, RR, SpO2, and PR readings. It provides views with text and graphics including numeric and trend graph, with the numeric view being primary and the trend graph view being secondary. IPI numeric readings are calculated for Adult patient types, and different classifications of pediatric patient types.

If the trend graphic is selected, an historical trend 255 is shown, as illustrated in FIG. 11B. The IPI trend graphic will provide IPI values on the y-axis and time on the x-axis. The y-axis upper (y-max) limit is 10 and the lower (y-min) limit is 0. The trend graph will continue to show no data until a patient has been connected to the CO2 sensor, a 'valid breath' has been received, and CO2, RR, SpO2, and PR readings required for the IPI calculation are available. Blank areas may appear in trend if sensor is not calculating/sending IPI readings to the device. The oldest to newest readings appear from left to right, with the most recent readings appearing beginning with the rightmost portion of the display area for the trend graphic.

Referring to FIGS. 12A-12B, the RR frame 262 is shown, which encapsulates data, information, and controls relevant for respiration readings capture. It provides a view with text and graphics.

As shown in FIG. 12B, in some instances, a respiration rate indicator graph 263 is shown. The respiration rate indicator graph 263 indicates the acquired signal quality and the respiration rate. As the detected respiration becomes stronger, more bars light up with each breath.

In some examples, the home screen 250 can display both continuous data and episodic data. For example, in typical scenarios, both continuous measurements and episodic measurements may be taken from a patient, and the information displayed on the home screen 250 can include episodic information that is not obtained in a continuous manner. One example of such an episodic parameter is NIBP. Another example is temperature (if not measured continuously).

For example, referring now to FIGS. 13A-13B, an NIPB frame 796 of the home screen 250 is shown. The data associated with the NIPB measurements is episodic, in that it is typically measured at given intervals, such as every 5 minutes, 10 minutes, 15 minutes 30 minutes, 1 hour, etc. As the data provided in the NIBP frame 796 ages, an indication of that aging is provided.

For example, in FIG. 13A, the measurements shown in the NIBP frame 796 are current, in that the measurements were taken within a given threshold of time, such as 10 minutes or 15 minutes. In other words, the measurements shown are less than 15 minutes old. This is indicated by displaying the data (e.g., "120/80") in a brighter color, such as a yellow.

In contrast, as shown in FIG. 13B, the NIPB measurements shown in the NIBP frame 796 have aged. In other words, after episodic measurements have been displayed for a given threshold (e.g., 15 minutes) without new measurement data being provided, the measurement data on the NIBP frame 796 changes from its current color to gray, and a timestamp (e.g., "@10:58") is displayed in the bottom of the NIBP frame 796 to indicate when the last measurements were taken. This allows the caregiver to easily determine that the displayed data may not be current. Other configurations can also be used to indicate aging of measurements.

For example, if measurements associated with continuous data are interrupted, the home screen 250 can be configured to provide the last known measurements, as well as indicate that such measurements have aged by providing indicia, such as changing color and providing a time stamp, as described above.

In addition, other modifications can be made to the various home screens described herein. For example, in some instances, as described further above, the type and amount of measurements shown on the home screen 250 can be modified depending on the type of view shown.

For example, in compressed or squished views, such as when alarm information is shown, only certain of the information associated with the parameters measured during the continuous workflow is shown. For example, in the compressed view of the home screen 250, SpO2 (and the associated pulse amplitude blip bar) and pulse rate are typically displayed.

However, for the home screen 250, when CO2 is shown, FiCO2 is not displayed in the compressed view, and the various other parameters are displayed in the following priority order (with up to five parameters shown at a given time): IPI/RR/SpO2/etCO2/PR/NIBP/Temp. When RRa (acoustic respiration rate) is shown on the home screen 250, the parameters are displayed in the following priority order: RRa/SpO2/PR/NIBP/Temp. Other configurations are possible.

In example embodiments, the desired workflow can be selected for the PMP device 200 based on operating conditions. For example, the continuous workflow can be selected if one or more sensors which measure continuous data are connected to the PMP device 200. In such a scenario, the measurements are displayed on the PMP device 200 and/or sent to a central site for storage, such as the EMR system 102.

In other embodiments, transitions between the various workflows can occur depending on the operating characteristics for the PMP device 200. For example, once a sensor associated with measuring continuous data is connected to the PMP device 200, the PMP device 200 can be configured to transition from a non-continuous workflow (e.g., monitoring workflow or non-monitoring workflow) to a continuous workflow. Additional details about such transitions are provided in U.S. patent application Ser. No. 13/440,860, filed on even date herewith, the entirety of which is hereby incorporated by reference.

Figure 14:
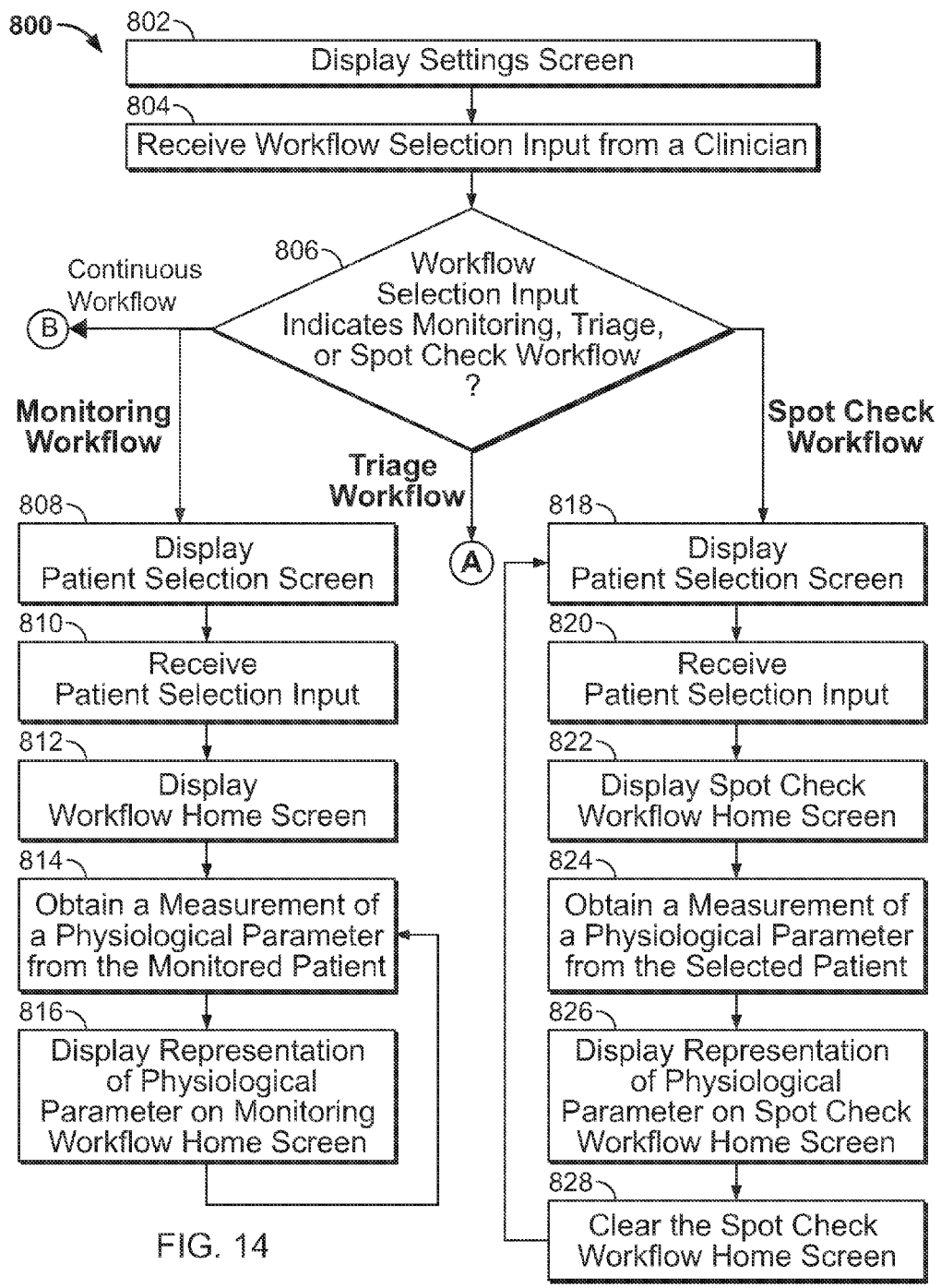
FIG. 14 is a flowchart illustrating an example operation performed by the PMP device.

FIG. 14 is a flowchart illustrating an example operation 800 performed by the PMP device 200. As illustrated in the example of FIG. 14, the operation 800 begins when the PMP device 200 displays the settings screen 600 (802). The PMP device 200 then receives workflow selection input from a clinician via the settings screen 600 (804). In response to receiving the workflow selection input, the PMP device 200 determines whether the workflow selection input indicates the monitoring workflow, the triage workflow, the spot check workflow, or the continuous workflow (806). If the PMP device 200 determines that the workflow selection input indicates the triage workflow, the PMP device 200 performs the steps illustrated in FIG. 15. If the PMP device 200 determines that the workflow selection input indicates the continuous workflow, the PMP device 200 performs the steps illustrated in FIG. 16.

If the PMP device 200 determines that the workflow selection input indicates the monitoring workflow, the PMP device 200 displays the patient selection screen 400 (808). The PMP device 200 then receives patient selection input from the clinician via the patient selection screen 400 (810). The patient selection input indicates a patient that the clinician intends to monitor.

Next, the PMP device 200 displays the monitoring workflow home screen 300 (812). In some embodiments, the PMP device 200 displays the monitoring workflow home screen 300 automatically after the clinician selects the monitored patient via the patient selection screen 400. In other embodiments, the PMP device 200 displays the monitoring workflow home screen 300 in response to the clinician selecting the home tab 318*a*.

Subsequently, the PMP device 200 obtains a measurement of a physiological parameter of the monitored patient (814). The PMP device 200 then displays a representation of the physiological parameter on the monitoring workflow home screen 300 (816). The representation of the physiological parameter is based, at least in part, on the measurement of the physiological parameter. The PMP device 200 then obtains another measurement of the physiological parameter from the same monitored patient (814). In this way, the PMP device 200 enables the clinician to monitor the physiological parameters of the same monitored patient over a period of time.

If, however, the PMP device 200 determines that the workflow selection input indicates the spot check workflow, the PMP device 200 displays the patient selection screen 400 (818). In various embodiments, the PMP device 200 displays the patient selection screen 400 in response to various events. For example, in some embodiments, the PMP device 200 automatically displays the patient selection screen 400 when the PMP device 200 determines that the workflow selection input indicates the spot check workflow. In another example, the PMP device 200 displays the patient selection screen 400 in response to receiving a selection of the patients tab 318*b*.

The PMP device 200 then receives patient selection input from the clinician via the patient selection screen 400 (820). The patient selection input indicates a selected patient. The selected patient is a patient on whom the clinician intends to perform a spot check.

Next, the PMP device 200 displays the spot check workflow home screen 330 (822). In various embodiments, the PMP device 200 displays the spot check workflow home screen 330 in response to various events. For example, in some embodiments, the PMP device 200 automatically displays the spot check workflow home screen 330 when the PMP device 200 receives the patient selection input from the clinician. In other embodiments, the PMP device 200 displays the spot check workflow home screen 330 in response to receiving a selection of the home tab 318*a*.

The PMP device 200 then obtains a measurement of a physiological parameter of the selected patient (824). In response to obtaining the measurement of the physiological parameter of the selected patient, the PMP device 200 displays a representation of the physiological parameter of the selected patent (826). The representation of the physiological parameter is based, at least in part, on the measurement of the physiological parameter.

Subsequently, the PMP device 200 clears the home screen data from the spot check workflow home screen 330 (828). The PMP device 200 then displays the patient selection screen 400 again (818) and receives patient selection input indicating another patient (818), and so on. In this way, the PMP device 200 displays representations of physiological parameters of each patient in a series of patients.

Figure 15:
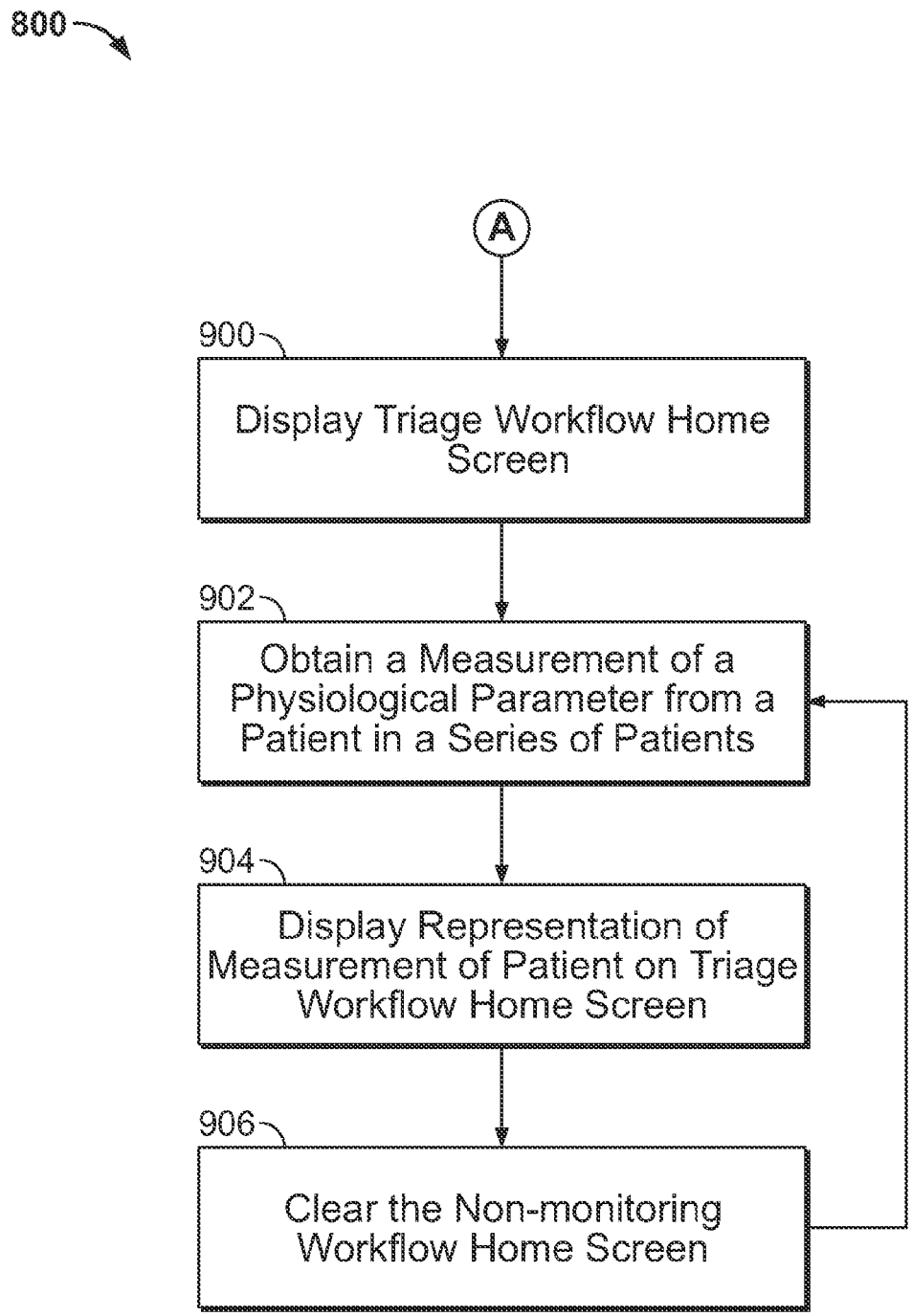
FIG. 15 is a flowchart representing a continuation of the operation in which the workflow selection input indicates the triage workflow.

FIG. 15 is a flowchart representing a continuation of the operation 800 in which the workflow selection input indicates the triage workflow. As illustrated in the example of FIG. 15, if the PMP device 200 determines that the workflow selection input indicates the triage workflow, the PMP device 200 displays the triage workflow home screen 360 (900). In various embodiments, the PMP device 200 displays the triage workflow home screen 360 in response to various events. For example, in some embodiments, the PMP device 200 automatically displays the triage workflow home screen 360 when the PMP device 200 determines that the workflow selection input indicates the triage workflow. In another example, the PMP device 200 displays the triage workflow home screen 360 when the PMP device 200 receives a selection of the home tab 318*a*.

Next, the PMP device 200 obtains a measurement of a physiological parameter of an unidentified patient in a series of patients (902). After obtaining the measurement, the PMP device 200 displays a representation of the physiological parameter on the triage workflow home screen 360 (904). The representation of the physiological parameter is based at least in part on the measurement of the physiological parameter.

Subsequently, the PMP device 200 clears the home screen data from the triage workflow home screen 360 (906). The PMP device 200 then obtains a measurement of the physiological parameter of a different patient in the series of unidentified patients (902), displays a representation of the physiological parameter (904), and so on. In this way, the PMP device 200 displays representations of physiological parameters of each patient in the series of unidentified patients.

Figure 16:
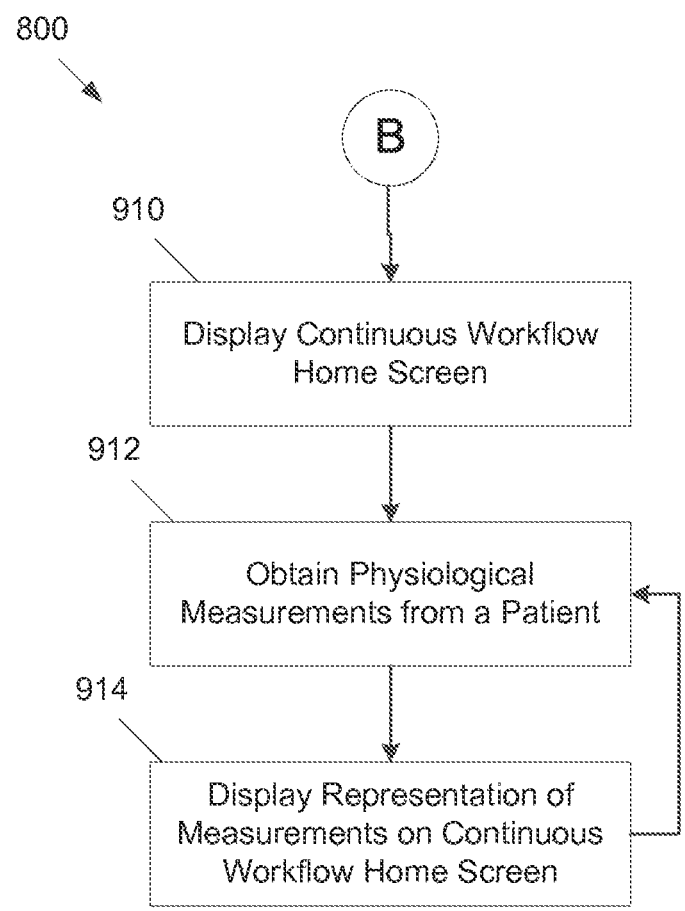
FIG. 16 is a flowchart representing a continuation of the operation in which the workflow selection input indicates the continuous workflow.

FIG. 16 is a flowchart representing a continuation of the operation 800 in which the workflow selection input indicates the continuous workflow. As illustrated in the example of FIG. 16, if the PMP device 200 determines that the workflow selection input indicates the continuous workflow, the PMP device 200 displays the continuous workflow home screen 250 (910). In various embodiments, the PMP device 200 displays the continuous workflow home screen 250 in response to various events. For example, in some embodiments, the PMP device 200 automatically displays the continuous workflow home screen 250 when the PMP device 200 determines that the workflow selection input indicates the continuous workflow. In another example, the PMP device 200 displays the continuous workflow home screen 250 when the PMP device 200 receives a selection of the home tab 318*a*.

Next, the PMP device 200 obtains measurements of physiological parameters of an identified patient (912). After obtaining the measurements, the PMP device 200 displays a representation of the physiological parameters on the continuous workflow home screen 250 (914). The representation of the physiological parameters is based at least in part on the measurement of the physiological parameters. The home screen 250 continues to disclose the physiological parameters as these parameters are continuously obtained from the patient by the PMP device 200.

Figure 17:
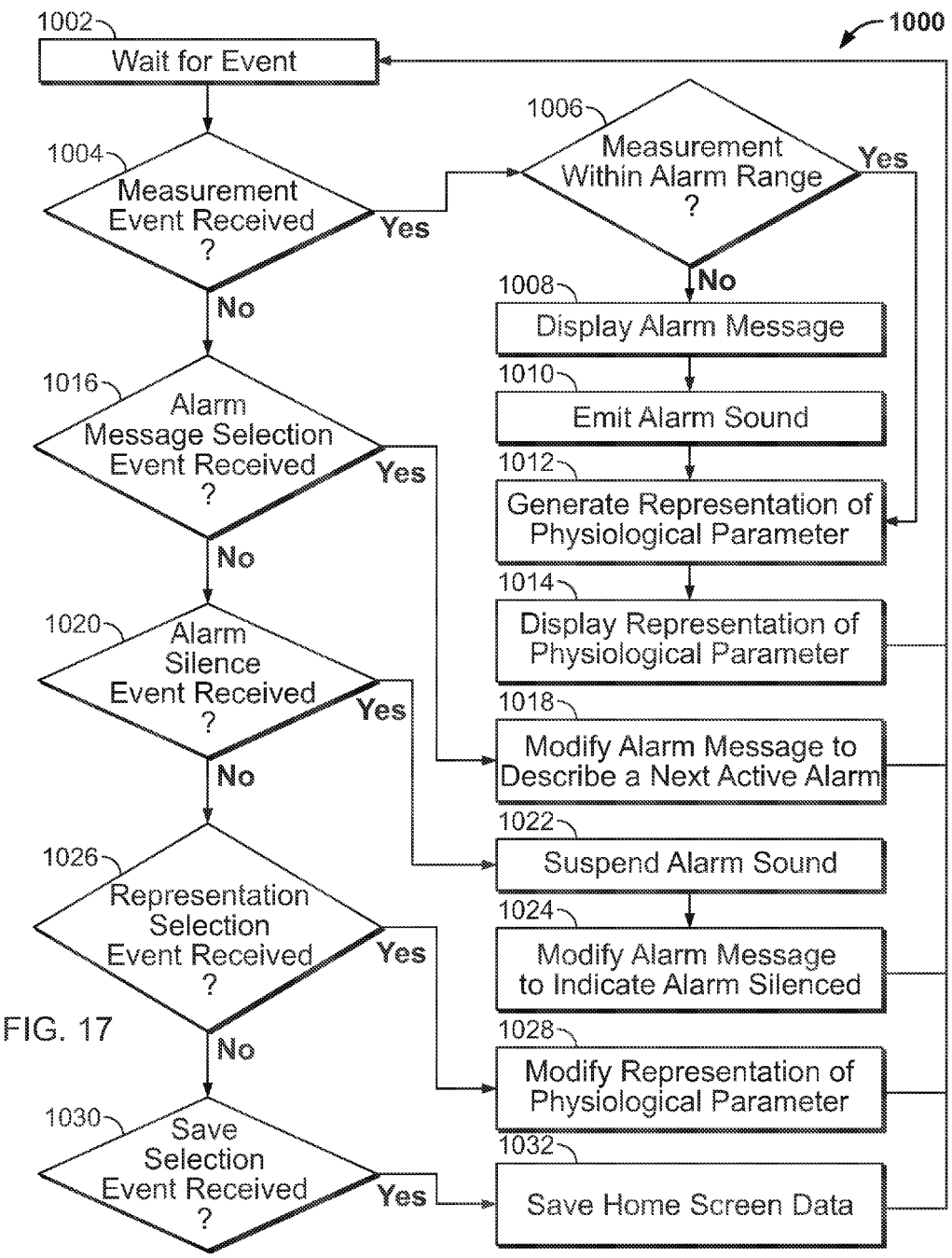
FIG. 17 is a flowchart illustrating an operation performed by the PMP device when the PMP device displays a workflow home screen.

FIG. 17 is a flowchart illustrating an operation 1000 performed by the PMP device 200 when the PMP device 200 displays a workflow home screen. In some embodiments, the PMP device 200 can perform the operation 1000 when the PMP device 200 displays either the monitoring workflow home screen 300, the spot check workflow home screen 330, or the triage workflow home screen 360.

As illustrated in the example of FIG. 17, the PMP device 200 initially waits to receive an event (1002). An event is an occurrence or happening of significance to a task or program.

The PMP device 200 receives a measurement event when the PMP device 200 receives a measurement of a physiological parameter of a patient. If the PMP device 200 receives a measurement event ("YES" of 1004), the PMP device 200 determines whether the measurement of the physiological parameter is within an alarm range for the physiological parameter (1006). If the measurement of the physiological parameter is not within (i.e., is outside) the alarm range for the physiological parameter ("NO" of 1006), the PMP device 200 displays an alarm message on the workflow home screen (1008). In addition, the PMP device 200 emits an alarm sound (1010).

The PMP device 200 also generates a representation of the physiological parameter based on the measurement of the physiological parameter (1012). The PMP device 200 generates the representation of the physiological parameter regardless of whether the measurement is within the alarm range of the physiological parameter. The PMP device 200 then displays the representation of the physiological parameter on the workflow home screen (1014). The PMP device 200 then waits for another event (1002).

The PMP device 200 can receive an alarm message selection event when the PMP device 200 displays an alarm message, there are two or more active alarms, and a clinician selects the alarm message. If the PMP device 200 receives an alarm message selection event ("YES" of 1016), the PMP device 200 modifies the alarm message such that the alarm message describes a next one of the active alarms (1018). The PMP device 200 then waits for another event (1002).

The PMP device 200 can receive an alarm silence event when an alarm is currently active, the PMP device 200 is emitting an alarm sound, and a clinician selects a control to suspend the alarm sound. If the PMP device 200 receives an alarm silence event ("YES" of 1020), the PMP device 200 suspends the alarm sound (1022). In addition, the PMP device 200 modifies the alarm message to indicate that the alarm has been silenced (1024). The PMP device 200 then waits for another event (1002).

The PMP device 200 can receive a representation selection event when a clinician selects a representation of a physiological parameter. If the PMP device 200 receives a representation selection event ("YES" of 1026), the PMP device 200 modifies a parameter reporting area associated with the physiological parameter such that the parameter reporting area contains a different representation of the physiological parameter (1028). The PMP device 200 then waits for another event (1002).

The PMP device 200 can receive a save selection event when a clinician selects a save button (e.g., save button 316g) on the workflow home screen. If the PMP device 200 receives a save selection event ("YES" of 1030), the PMP device 200 saves the home screen data (1032). The PMP device 200 then waits for another event (1002).

Figure 18:
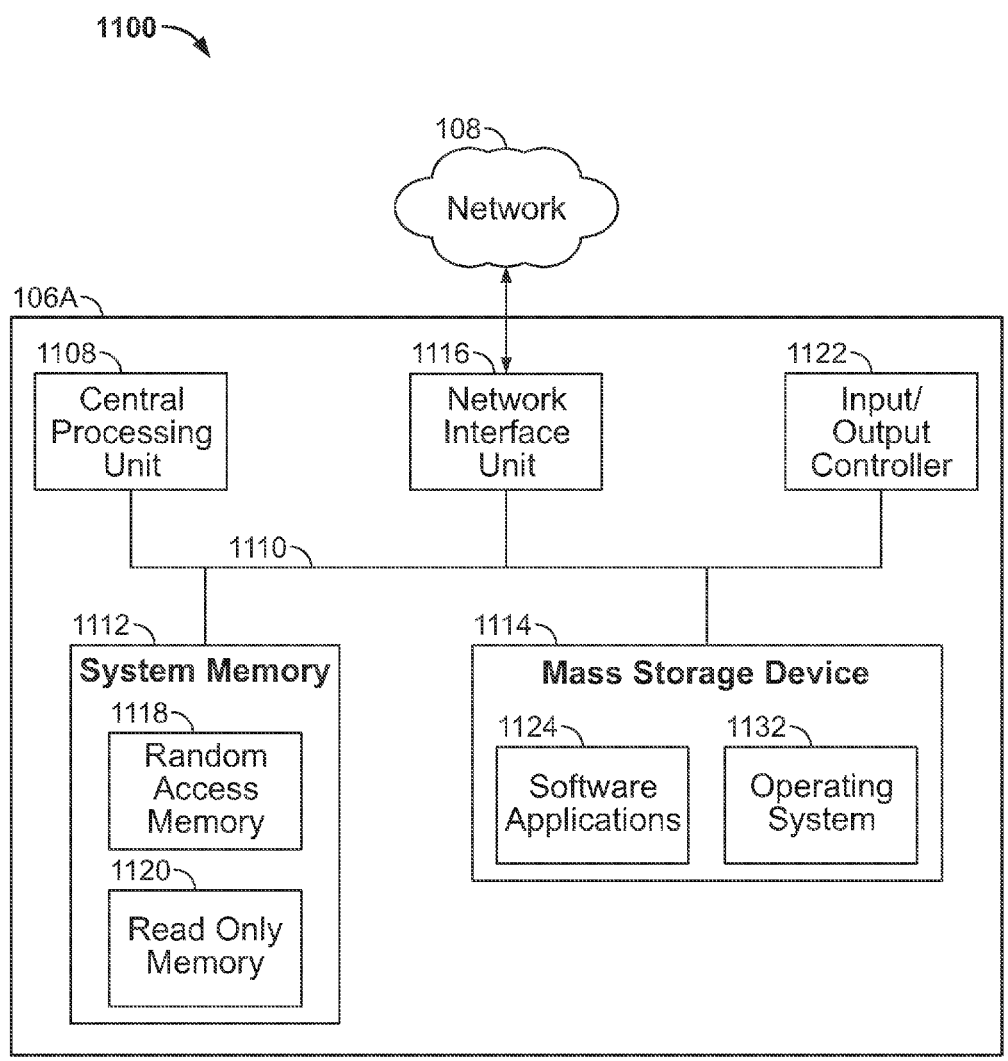
FIG. 18 illustrates example physical components of the PMP device.

FIG. 18 illustrates example physical components of the PMP device 200. As illustrated in the example of FIG. 18, the PMP device 200 include at least one central processing unit ("CPU") 1108, a system memory 1112, and a system bus 1110 that couples the system memory 1112 to the CPU 1108. The system memory 1112 includes a random access memory ("RAM") 1118 and a read-only memory ("ROM") 1120. A basic input/output system containing the basic routines that help to transfer information between elements within the PMP device 200, such as during startup, is stored in the ROM 1120. The PMP device 200 further includes a mass storage device 1114. The mass storage device 1114 is able to store software instructions and data.

The mass storage device 1114 is connected to the CPU 1108 through a mass storage controller (not shown) connected to the bus 1110. The mass storage device 1114 and its associated computer-readable data storage media provide non-volatile, non-transitory storage for the PMP device 200. Although the description of computer-readable data storage media contained herein refers to a mass storage device, such as a hard disk or CD-ROM drive, it should be appreciated by those skilled in the art that computer-readable data storage media can be any available non-transitory, physical device or article of manufacture from which the PMP device 200 can read data and/or instructions.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the PMP device 200.

According to various embodiments of the disclosure, the PMP device 200 may operate in a networked environment using logical connections to remote network devices through the network 108, such as a local network, the Internet, or another type of network. The PMP device 200 connects to the network 108 through a network interface unit 1116 connected to the bus 1110. It should be appreciated that the network interface unit 1116 may also be utilized to connect to other types of networks and remote computing systems. The PMP device 200 also includes an input/output controller 1122 for receiving and processing input from a number of other devices, including a keyboard, a mouse, a touch user interface display screen, or another type of input device. Similarly, the input/output controller 1122 may provide output to a touch user interface display screen, a printer, or other type of output device.

As mentioned briefly above, the mass storage device 1114 and the RAM 1118 of the PMP device 200 can store software instructions and data. The software instructions include an operating system 1132 suitable for controlling the operation of the PMP device 200. The mass storage device 1114 and/or the RAM 1118 also store software instructions, that when executed by the CPU 1108, cause the PMP device 200 to provide the functionality of the PMP device 200 discussed in this document. For example, the mass storage device 1114 and/or the RAM 1118 can store software instructions that, when executed by the CPU 1108, cause the PMP device to display the monitoring workflow home screen 300 and other screens.

It should be appreciated that various embodiments can be implemented (1) as a sequence of computer implemented acts or program modules running on a computing system and/or (2) as interconnected machine logic circuits or circuit modules within the computing system. The implementation is a matter of choice dependent on the performance requirements of the computing system implementing the disclosure. Accordingly, logical operations including related algorithms can be referred to variously as operations, structural devices, acts or modules. It will be recognized by one skilled in the art that these operations, structural devices, acts and modules may be implemented in software, firmware, special purpose digital logic, and any combination thereof without deviating from the spirit and scope of the present disclosure as recited within the claims set forth herein.

Although the disclosure has been described in connection with various embodiments, those of ordinary skill in the art will understand that many modifications may be made thereto within the scope of the claims that follow. For example, it should be appreciated that the screens illustrated in this document are merely examples and that in other embodiments equivalent screens can have different contents and appearances. Accordingly, it is not intended that the scope of the disclosure in any way be limited by the above description, but instead be determined entirely by reference to the claims that follow.

What is claimed is:

1. A physiological measuring platform (PMP) device comprising:
   a central processing unit (CPU) that is configured to control operation of the PMP device;
   a display screen;
   at least one physiological sensor; and
   a set of one or more computer readable data storage media storing software instructions that, when executed by the CPU, cause the PMP device to:
   display, on the display screen, a settings screen enabling a user to select a workflow within which the PMP device is to operate from a plurality of workflows that operate exclusively of each other, including at least an intervals monitoring workflow, a non-monitoring workflow, and a continuous workflow, wherein the workflow selection determines a functionality provided by the PMP device;
   obtain a continuous measurement of a physiological parameter of a monitored patient with the at least one physiological sensor when the PMP device is operating within the continuous workflow; and
   display, on the display screen, a continuous workflow home screen when the PMP device is operating within the continuous workflow, the continuous workflow home screen containing a first representation of the physiological parameter of the monitored patient, the first representation based on the continuous measurement of the physiological parameter of the monitored patient.

2. The PMP device of claim 1, wherein the software instructions, when executed by the CPU, cause the PMP device to:
   obtain a series of measurements taken at intervals of a physiological parameter of a monitored patient with the at least one physiological sensor when the PMP device is operating within the intervals monitoring workflow;
   display, on the display screen, an intervals monitoring workflow home screen when the PMP device is operating within the intervals monitoring workflow, the intervals monitoring workflow home screen containing a second representation of the physiological parameter of the monitored patient, the second representation based on a measurement in the series of measurements;
   obtain a measurement of the physiological parameter of each patient in a series of patients with the at least one physiological sensor when the PMP device is operating within the non-monitoring workflow; and
   display, on the display screen, a non-monitoring workflow home screen when the PMP device is operating within the non-monitoring workflow, the non-monitoring workflow home screen containing a third representation of the physiological parameter of a given patient in the series of patients, the third representation based on the measurement of the physiological parameter of the given patient in the series of patients,
   wherein the intervals monitoring workflow home screen, the non-monitoring workflow home screen, and the continuous workflow home screen are each different; and
   wherein the intervals monitoring workflow home screen, the non-monitoring workflow home screen, and the continuous workflow home screen operate exclusively of each other.

3. The PMP device of claim 1, wherein the continuous workflow home screen includes an SpO2 frame, the SpO2 frame displaying an oxygen saturation percentage and a pulse amplitude blip bar indicating a pulse beat relative pulse amplitude.

4. The PMP device of claim 1, wherein the continuous workflow home screen includes an etCO2 frame, the etCO2 frame displaying a numeric value representing etCO2 and a Capnogram waveform.

5. The PMP device of claim 1, wherein the continuous workflow home screen includes an RR frame, the RR frame displaying a numeric value representing respirations per minute, and a respiration rate indicator graph with a plurality of bars, such that, as a detected respiration becomes stronger, more of the bars light up.

6. The PMP device of claim 1, wherein the continuous workflow home screen displays both continuous data and episodic data.

7. The PMP device of claim 6, wherein an aging of the episodic data is shown on the continuous workflow home screen.

8. The PMP device of claim 7, wherein the aging is shown by changing a display color of the episodic data when an age of the data reaches a threshold.

9. A physiological measuring platform (PMP) device comprising:
   a central processing unit (CPU) that is configured to control operation of the PMP device;
   a display screen;
   at least one physiological sensor; and
   a set of one or more computer readable data storage media storing software instructions that, when executed by the CPU, cause the PMP device to:
   display a settings screen on a display screen, the settings screen enabling a user to select a workflow within which the PMP device is to operate from a plurality of workflows that operate exclusively of each other, including at least an intervals monitoring workflow, a non-monitoring workflow, and a continuous workflow, wherein the workflow selection determines a functionality provided by the PMP device; and
   when the PMP device is operating within the continuous workflow:
   obtain continuous measurements of a continuous physiological parameter of the monitored patient with the at least one physiological sensor; and
   display a continuous workflow home screen on the display screen, the continuous workflow home screen containing:
   a first representation of the continuous physiological parameter of the monitored patient, the first representation based on a continuous measurement in the continuous measurements;
a device status area containing data regarding a status of the PMP device;
a content area, the content area including a parameter reporting area and a patient attribute area, the parameter reporting area containing a plurality of parameter reporting frames that are each directed to reporting a value of a different physiological parameter; and
a navigation area, the navigation area including screen tabs associated with different screens.

10. The PMP device of claim 9, wherein the software instructions, when executed by the CPU, cause the PMP device to:
when the PMP device is operating within the intervals monitoring workflow:
obtain a series of measurements of a physiological parameter of a monitored patient with the at least one physiological sensor; and
display an intervals monitoring workflow home screen on the display screen, the intervals monitoring workflow home screen containing a second representation of the physiological parameter of the monitored patient, the second representation based on a measurement in the series of measurements;
when the PMP device is operating within the non-monitoring workflow:
obtain a measurement of the physiological parameter of each patient in a series of patients with the at least one physiological sensor; and
display a non-monitoring workflow home screen on the display screen, the non-monitoring workflow home screen containing a third representation of the physiological parameter of a given patient in the series of patients, the third representation based on the measurement of the physiological parameter of the given patient in the series of patients,
wherein the intervals monitoring workflow home screen and the non-monitoring workflow home screen each comprise:
a device status area containing data regarding a status of the PMP device;
a content area, the content area including a parameter reporting area and a patient attribute area, the parameter reporting area containing a plurality of parameter reporting frames that are each directed to reporting a value of a different physiological parameter; and
a navigation area, the navigation area including screen tabs associated with different screens.

11. The PMP device of claim 9, wherein the physiological parameter displayed on the continuous workflow home screen includes one of SpO2, SpHb, etCO2, IPI, and RR.

12. The PMP device of claim 9, wherein the continuous workflow home screen includes an SpO2 frame, the SpO2 frame displaying an oxygen saturation percentage and a pulse amplitude blip bar indicating a pulse beat relative pulse amplitude.

13. The PMP device of claim 12, wherein the continuous workflow home screen includes an etCO2 frame, the etCO2 frame displaying a numeric value representing etCO2 and a Capnogram waveform.

14. The PMP device of claim 9, wherein the continuous workflow home screen includes an etCO2 frame, the etCO2 frame displaying a numeric value representing etCO2 and a Capnogram waveform.

15. The PMP device of claim 9, wherein the continuous workflow home screen includes an RR frame, the RR frame displaying a numeric value representing respirations per minute, and a respiration rate indicator graph with a plurality of bars, such that, as a detected respiration becomes stronger, more of the bars light up with each breath.

16. The PMP device of claim 9, wherein the continuous workflow home screen displays both continuous and episodic data.

17. The PMP device of claim 16, further comprising showing an aging of the episodic data on the continuous workflow home screen.

18. The PMP device of claim 17, further comprising changing a display color of the episodic data when an age of the data reaches a threshold.

19. A non-transitory, computer-readable storage medium comprising software instructions that, when executed, cause a physiological measurement platform (PMP) device to:
display, on the display screen, a settings screen enabling a user to select a workflow within which the PMP device is to operate from a plurality of workflows that operate exclusively of each other, including at least an intervals monitoring workflow, a non-monitoring workflow, and a continuous workflow, wherein the workflow selection determines a functionality provided by the PMP device;
obtain a series of measurements of a physiological parameter of a monitored patient when the PMP device is operating within the intervals monitoring workflow;
display, on the display screen, one of a plurality of workflow home screens, each of the workflow home screens being configured to address a different type of workflow;
when a continuous workflow home screen is selected:
obtain a continuous measurement of the physiological parameter of the monitored patient when the PMP device is operating within the continuous workflow; and
display, on the display screen, the continuous workflow home screen when the PMP device is operating within the continuous workflow, the continuous workflow home screen containing a representation of the physiological parameter of the monitored patient, the representation based on the measurement of the physiological parameter of the monitored patient, the continuous workflow home screen including:
an SpO2 frame displaying an oxygen saturation percentage and a pulse amplitude blip bar indicating a pulse beat relative pulse amplitude;
an etCO2 frame displaying a numeric value representing etCO2 and a Capnogram waveform;
an RR frame displaying a numeric value representing respirations per minute; and
episodic data, wherein the aging is shown by changing a display color of the episodic data when an age of the data reaches a threshold.

* * * * *